United States Patent
Prince

(10) Patent No.: US 8,510,059 B2
(45) Date of Patent: Aug. 13, 2013

(54) METHOD AND SYSTEM FOR MEASURING EMISSION AND QUANTIFYING EMISSION SOURCE

(75) Inventor: Dennis Scott Prince, Edmonton (CA)

(73) Assignee: Airdar Inc., Edmonton (CA)

( * ) Notice: Subject to any disclaimer, the term of this patent is extended or adjusted under 35 U.S.C. 154(b) by 503 days.

(21) Appl. No.: 12/759,857

(22) Filed: Apr. 14, 2010

(65) Prior Publication Data

US 2010/0268480 A1 Oct. 21, 2010

Related U.S. Application Data

(60) Provisional application No. 61/168,965, filed on Apr. 14, 2009.

(51) Int. Cl.
*G01W 1/00* (2006.01)
*G01P 5/00* (2006.01)

(52) U.S. Cl.
USPC .................................. 702/24; 702/3; 702/142

(58) Field of Classification Search
USPC ................................................ 702/3, 24, 142
See application file for complete search history.

(56) References Cited

U.S. PATENT DOCUMENTS

| | | | |
|---|---|---|---|
| 4,127,780 A | 11/1978 | Kimbell |
| 4,135,092 A | 1/1979 | Milly |
| 4,204,121 A | 5/1980 | Milly |
| 5,099,437 A | 3/1992 | Weber |
| 5,106,756 A | 4/1992 | Zaromb |
| 5,347,285 A | 9/1994 | MacDoran et al. |
| 5,386,373 A | 1/1995 | Keeler et al. |
| 5,604,299 A | 2/1997 | Cobb |
| 5,719,396 A | 2/1998 | Jack et al. |
| 5,726,450 A | 3/1998 | Peterson et al. |
| 5,832,411 A | 11/1998 | Schatzmann et al. |
| 5,879,943 A | 3/1999 | Ando et al. |
| 5,918,257 A | 6/1999 | Mifsud et al. |
| 6,734,824 B2 | 5/2004 | Herman |
| 6,895,335 B2 | 5/2005 | Archibald et al. |
| 7,523,638 B2 | 4/2009 | Prince |
| 2002/0169557 A1 | 11/2002 | Gilbert et al. |

(Continued)

FOREIGN PATENT DOCUMENTS

| | | |
|---|---|---|
| EP | 448360 A1 | 9/1991 |
| JP | 11118701 A | 4/1999 |
| WO | WO 2004/010398 | 1/2004 |
| WO | WO 2008/086606 | 7/2008 |

OTHER PUBLICATIONS

The Alberta Oil Sands Community Exposure and Health Effects Assessment Program: Technical Report (Dr. Petros Koutrakis et al.), Aug. 2000, pp. 206-217.

(Continued)

*Primary Examiner* — Janet Suglo
(74) *Attorney, Agent, or Firm* — Bennett Jones LLP

(57) ABSTRACT

A system and method for quantifying an emission source is provided. The system and method obtain a plurality of emission concentration measurements at one or more sampling points and wind data over the time the emission concentrations are measured. For each sampling point, a virtual sampling arc can be constructed using the emission concentration measurements taken at the sampling point, the wind data for when the emission concentration measurement were taken and an approximate distance to the emission source. The virtual sampling arcs can then be used to construct one or more virtual sampling grids and the amount of emissions emanating from the emissions source approximated from the virtual sampling grids.

22 Claims, 61 Drawing Sheets

(56) References Cited

U.S. PATENT DOCUMENTS

| | | |
|---|---|---|
| 2004/0204885 A1 | 10/2004 | Wang et al. |
| 2005/0039515 A1 | 2/2005 | Prince |
| 2007/0061114 A1 | 3/2007 | Kalayeh |
| 2008/0195329 A1 | 8/2008 | Prince et al. |
| 2009/0133465 A1 | 5/2009 | Prince |
| 2009/0139299 A1 | 6/2009 | Prince |
| 2010/0094565 A1 | 4/2010 | Prince et al. |

OTHER PUBLICATIONS

Remote Detection and Quantification of Fugitive Emission Sources Using Ambient Measurements, Paper 2010-A155-AWMA, Sikora et al.

| Inlet number | Position of Center (m) | Element Height | 229 | 230 | 231 | 232 | 233 | 234 | 235 | 236 | 237 | 238 | 239 | 240 | 241 | 242 |
|---|---|---|---|---|---|---|---|---|---|---|---|---|---|---|---|---|
| Horizontal Position (deg) | | | -22.0 | -20.9 | -19.9 | -18.9 | -17.8 | -16.8 | -15.7 | -14.7 | -13.6 | -12.6 | -11.5 | -10.5 | -9.4 | -8.4 |
| Horizontal Position (m) | | | 1.05 | 1.05 | 1.05 | 1.05 | 1.05 | 1.05 | 1.05 | 1.05 | 1.05 | 1.05 | 1.05 | 1.05 | 1.05 | 1.05 |
| Element width (m) | | | 1.05 | | | | | | | | | | | | | |
| 1 | 0.3 | 0.5 | 1.23 | 0.43 | 0.61 | 0.78 | 0.55 | 0.89 | 1.00 | 1.45 | 1.87 | 2.41 | 3.99 | 3.94 | 4.85 | 6.93 |
| 2 | 0.8 | 0.6 | | 0.38 | 0.39 | 0.54 | 0.72 | 0.90 | 0.39 | 1.92 | 2.25 | 2.75 | 1.62 | 2.80 | 5.37 | 6.44 |
| 3 | 1.5 | 1.1 | 0.21 | 0.21 | 0.15 | 0.35 | 0.95 | 1.33 | 1.86 | 2.05 | 2.24 | 2.64 | 3.19 | 3.96 | 4.67 | 5.06 |
| 4 | 3.0 | 1.5 | 0.47 | 0.72 | 0.64 | 1.20 | 1.28 | 1.37 | 1.09 | 1.14 | 1.64 | 2.03 | 2.43 | 3.19 | 3.58 | 4.63 |
| 5 | 4.6 | 1.5 | 0.74 | 0.86 | 0.88 | 0.96 | 0.75 | 0.69 | 0.54 | 1.15 | 1.50 | 1.74 | 1.99 | 2.71 | 2.84 | 3.13 |
| 6 | 6.1 | 1.5 | 0.04 | 0.12 | 0.23 | 0.37 | 0.49 | 0.87 | 0.79 | 0.86 | 0.97 | 1.20 | 1.19 | 1.49 | 1.69 | 2.25 |
| 7 | 7.6 | 1.5 | 0.69 | 0.50 | 0.28 | 0.04 | 0.16 | 0.18 | 0.26 | 0.39 | 0.75 | 0.91 | 1.17 | 1.14 | 1.26 | 1.16 |
| 8 | 9.1 | 2.3 | 0.43 | 0.47 | 0.45 | 0.32 | 0.35 | 0.39 | 0.42 | 0.45 | 0.77 | 0.90 | 0.97 | 0.83 | 0.99 | 0.85 |
| 9 | 12.2 | 3.0 | 0.05 | 0.30 | 0.17 | 0.09 | | 0.17 | 0.40 | 0.85 | 0.95 | 0.92 | 0.41 | 0.30 | 0.30 | 0.37 |
| 10 | 15.2 | 3.0 | 0.21 | 0.40 | 0.33 | 0.42 | 0.13 | 0.34 | 0.29 | 0.35 | 0.34 | 0.48 | 0.51 | 0.25 | 0.23 | 0.27 |

FIG. 17A

| Horizontal Position (deg) | 243 | 244 | 245 | 246 | 247 | 248 | 249 | 250 | 251 | 252 | 253 | 254 | 255 | 256 | 257 |
|---|---|---|---|---|---|---|---|---|---|---|---|---|---|---|---|
| Horizontal Position (m) | -7.3 | -6.3 | -5.2 | -4.2 | -3.1 | -2.1 | -1.0 | 0.0 | 1.0 | 2.1 | 3.1 | 4.2 | 5.2 | 6.3 | 7.3 |
| Element width (m) | 1.05 | 1.05 | 1.05 | 1.05 | 1.05 | 1.05 | 1.05 | 1.05 | 1.05 | 1.05 | 1.05 | 1.05 | 1.05 | 1.05 | 1.05 |
| | 8.37 | 10.6 | 12.3 | 15.4 | 16.3 | 16.1 | 15.7 | 15.6 | 15.8 | 14.8 | 14.2 | 12.6 | 10.4 | 7.04 | 6.05 |
| | 8.62 | 9.89 | 10.9 | 12.3 | 15.0 | 17.3 | 18.2 | 16.2 | 14.4 | 12.2 | 11.5 | 10.5 | 10.3 | 8.44 | 8.02 |
| | 6.30 | 6.96 | 9.22 | 10.2 | 12.1 | 12.4 | 13.6 | 13.3 | 13.3 | 11.7 | 11.1 | 9.82 | 8.55 | 6.89 | 5.84 |
| | 5.74 | 6.95 | 7.90 | 8.67 | 8.96 | 9.69 | 10.1 | 9.84 | 9.00 | 8.21 | 8.05 | 7.42 | 6.84 | 5.47 | 4.23 |
| | 3.44 | 4.37 | 4.58 | 5.06 | 5.23 | 5.62 | 5.61 | 5.70 | 5.63 | 5.42 | 5.24 | 4.69 | 4.35 | 2.55 | 2.00 |
| | 2.38 | 2.69 | 2.82 | 3.18 | 3.66 | 3.76 | 3.83 | 3.66 | 3.79 | 3.67 | 3.26 | 3.00 | 2.85 | 2.89 | 2.17 |
| | 1.12 | 1.41 | 1.62 | 2.05 | 2.09 | 2.28 | 2.07 | 2.18 | 2.29 | 2.44 | 2.20 | 1.90 | 1.76 | 1.74 | 1.46 |
| | 0.87 | 0.83 | 1.07 | 1.07 | 1.19 | 1.35 | 1.60 | 1.51 | 1.33 | 1.27 | 1.40 | 1.39 | 1.10 | 1.19 | 1.19 |
| | 0.50 | 0.65 | 0.50 | 0.40 | 0.24 | 0.36 | 0.44 | 0.65 | 0.57 | 0.52 | 0.47 | 0.74 | 0.80 | 0.57 | 0.44 |
| | 0.39 | 0.27 | 0.29 | 0.29 | 0.29 | 0.27 | 0.24 | 0.16 | 0.08 | 0.17 | 0.28 | 0.29 | 0.18 | 0.07 | |

| Inlet number | Position of Center (m) | Element Height |
|---|---|---|
| 1 | 0.3 | 0.5 |
| 2 | 0.8 | 0.6 |
| 3 | 1.5 | 1.1 |
| 4 | 3.0 | 1.5 |
| 5 | 4.6 | 1.5 |
| 6 | 6.1 | 1.5 |
| 7 | 7.6 | 1.5 |
| 8 | 9.1 | 2.3 |
| 9 | 12.2 | 3.0 |
| 10 | 15.2 | 3.0 |

FIG. 17B

| Horizontal Position (deg) | 258 | 259 | 260 | 261 | 262 | 263 | 264 | 265 | 266 | 267 | 268 | 269 | 270 | 271 |
|---|---|---|---|---|---|---|---|---|---|---|---|---|---|---|
| Horizontal Position (m) | 8.4 | 9.4 | 10.5 | 11.5 | 12.6 | 13.6 | 14.7 | 15.7 | 16.8 | 17.8 | 18.9 | 19.9 | 20.9 | 22.0 |
| Element width (m) | 1.05 | 1.05 | 1.05 | 1.05 | 1.05 | 1.05 | 1.05 | 1.05 | 1.05 | 1.05 | 1.05 | 1.05 | 1.05 | 1.05 |
| | 3.70 | 2.27 | 2.54 | 2.73 | 2.30 | 1.15 | 0.57 | 0.70 | 0.09 | 0.05 | | 0.98 | 0.60 | 0.51 |
| | 5.42 | 4.59 | 3.94 | 2.45 | 1.04 | 0.72 | 1.03 | 0.96 | 0.54 | 0.19 | 0.26 | 0.64 | 0.19 | 0.19 |
| | 4.98 | 4.12 | 2.83 | 2.71 | 1.67 | 1.27 | 0.83 | 0.59 | 0.67 | 0.82 | 0.76 | 0.79 | 0.67 | 0.38 |
| | 3.08 | 2.87 | 2.37 | 1.32 | 1.00 | 0.71 | 0.65 | 0.36 | 0.34 | 0.41 | 0.42 | 0.61 | 0.57 | 0.67 |
| | 1.71 | 2.09 | 1.78 | 1.25 | 0.92 | 0.73 | 0.42 | 0.47 | 0.73 | 0.77 | 0.63 | 0.29 | 0.33 | 0.32 |
| | 1.69 | 1.38 | 1.24 | 1.06 | 0.45 | 0.16 | | 0.01 | 0.17 | 0.21 | 0.26 | 0.12 | | |
| | 1.05 | 0.84 | 0.71 | 0.54 | 0.37 | 0.26 | 0.35 | 0.34 | | | | 0.16 | 0.19 | 0.04 |
| | 1.16 | 0.94 | 0.71 | 0.50 | 0.49 | 0.55 | 0.48 | 0.36 | 0.31 | 0.27 | 0.31 | 0.35 | 0.60 | 0.71 |
| | 0.50 | 0.76 | 0.58 | 0.65 | 0.40 | 0.42 | 0.11 | 0.15 | 0.25 | 0.48 | 0.50 | 0.38 | 0.38 | 0.35 |
| | | | 0.23 | 0.29 | 0.30 | 0.23 | 0.42 | 0.51 | 0.51 | 0.38 | 0.30 | 0.23 | 0.38 | 0.54 |

| Inlet number | Position of Center (m) | Element Height |
|---|---|---|
| 1 | 0.3 | 0.5 |
| 2 | 0.8 | 0.6 |
| 3 | 1.5 | 1.1 |
| 4 | 3.0 | 1.5 |
| 5 | 4.6 | 1.5 |
| 6 | 6.1 | 1.5 |
| 7 | 7.6 | 1.5 |
| 8 | 9.1 | 2.3 |
| 9 | 12.2 | 3.0 |
| 10 | 15.2 | 3.0 |

FIG. 17C

METHOD AND SYSTEM FOR MEASURING EMISSION AND QUANTIFYING EMISSION SOURCE

CROSS REFERENCE TO RELATED APPLICATIONS

The present application claims priority under 35 U.S.C. §119(e) to U.S. provisional patent application No. 61/168,965 filed Apr. 14, 2009.

FIELD OF THE INVENTION

The present invention relates to air monitoring and more specifically to a method and system for quantifying an emission source.

BACKGROUND OF THE INVENTION

The reduction of contaminant emission into the air is important to decreasing our environmental impact on the environment. Air quality monitoring can be an inexact science. Air contaminants are often visually imperceptible and even when they may be visible, they are often hard to discern and/or quantify by visualizations alone. Often, the methods used to monitor the rate of emission into the air, such as contaminants, are simple and often inaccurate or alternatively, very complex, requiring skilled experienced professionals and often error prone. Even in cases where the methods are successfully performed, the resulting observations may be too vague or inaccurate to provide a meaningful quantification of the emissions.

SUMMARY OF THE INVENTION

In one aspect, a method for quantifying an emission source is provided. The method comprises: obtaining a plurality of emission concentrations measurements at a plurality of sampling points; obtaining wind speed measurements and wind direction measurements when the plurality of emission concentration measurements are taken; for each sampling point, constructing a virtual sampling arc made up of a plurality of points, each point based on: an emission concentration measurement taken at the sampling point; a wind direction when the emission concentration measurement was taken; and an approximate distance to the emission source, wherein all of the emission concentration measurements used to construct one of the virtual sampling arcs were taken at substantially the same wind speed; grouping virtual sampling arcs made of emission concentrations measurements at substantially the same wind speed into a virtual sampling grid; and approximating the amount of emissions passing through the virtual sampling grid.

In another aspect, a method for quantifying an emission source is provided. The method comprises obtaining a plurality of emission concentrations measurements at a single sampling point; obtaining wind speed measurements and wind direction measurements when the plurality of emission concentration measurements are taken; constructing a virtual sampling arc made up of a plurality of points, each point based on: an emission concentration measurement taken at the single sampling point; a wind direction when the emission concentration measurement was taken; and an approximate distance to the emission source, wherein all of the emission concentration measurements used to construct the virtual sampling arcs were taken at substantially the same wind speed; estimating an emissions plume shape with the virtual sampling arc passing through it; extrapolating points in the emission plume shape using points from the virtual sampling arc; and approximating the amount of emissions passing through the emission plume shape.

In another aspect, a system for quantifying an emission source is provided. The system comprises: a plurality of sampling points operative to obtain emission concentration measurements; at least one emission monitor operative take emission concentration measurements at the plurality of sampling points; a data processing device operatively connected to the at least one emission monitor to obtain emission concentration measurements from the at least one monitor, the data processing device operative to: obtain a plurality of emission concentrations measurements from the at least one emission monitor; obtain wind speed measurements and wind direction measurements when the plurality of emission concentration measurements were taken; for each sampling point, construct a virtual sampling arc made up of a plurality of points, each point based on: an emission concentration measurement taken at the sampling point; a wind direction measurement when the emission concentration measurement was taken; and an approximate distance to the emission source, wherein all of the emission concentration measurements used to construct one of the virtual sampling arcs were taken at substantially the same wind speed; group virtual sampling arcs made of emission concentrations measurements at substantially the same wind speed into a virtual sampling grid; and approximate the amount of emissions passing through the virtual sampling grid.

In another aspect, a method for quantifying an area emission source is provided. The method comprises: obtaining a plurality of emission concentrations measurements at a plurality of sampling points; obtaining wind speed measurements and wind direction measurements when the plurality of emission concentration measurements are taken; for each sampling point, constructing a virtual sampling array made up of a plurality of points, each point based on: an emission concentration measurement taken at the sampling point; a wind direction measurement when the emission concentration measurement was taken; and a representative distance to a representative center of a catchment area of the area emission source being measured by the emission concentration measurement, wherein all of the emission concentration measurements used to construct one of the virtual sampling arrays were taken at substantially the same wind speed; grouping virtual sampling arrays made of emission concentrations measurements taken at substantially the same wind speed into a virtual sampling grid; and approximating the amount of emissions passing through the virtual sampling grid.

BRIEF DESCRIPTION OF THE DRAWINGS

Referring to the drawings wherein like reference numerals indicate similar parts throughout the several views, several aspects of the present invention are illustrated by way of example, and not by way of limitation, in detail in the figures, wherein:

FIG. 17 is a table of obtained data across a virtual sampling grid;

DESCRIPTION OF VARIOUS EMBODIMENTS

The detailed description set forth below in connection with the appended drawings is intended as a description of various embodiments of the present invention and is not intended to represent the only embodiments contemplated by the inventor. The detailed description includes specific details for the purpose of providing a comprehensive understanding of the present invention. However, it will be apparent to those skilled in the art that the present invention may be practiced without these specific details.

Figure 1:
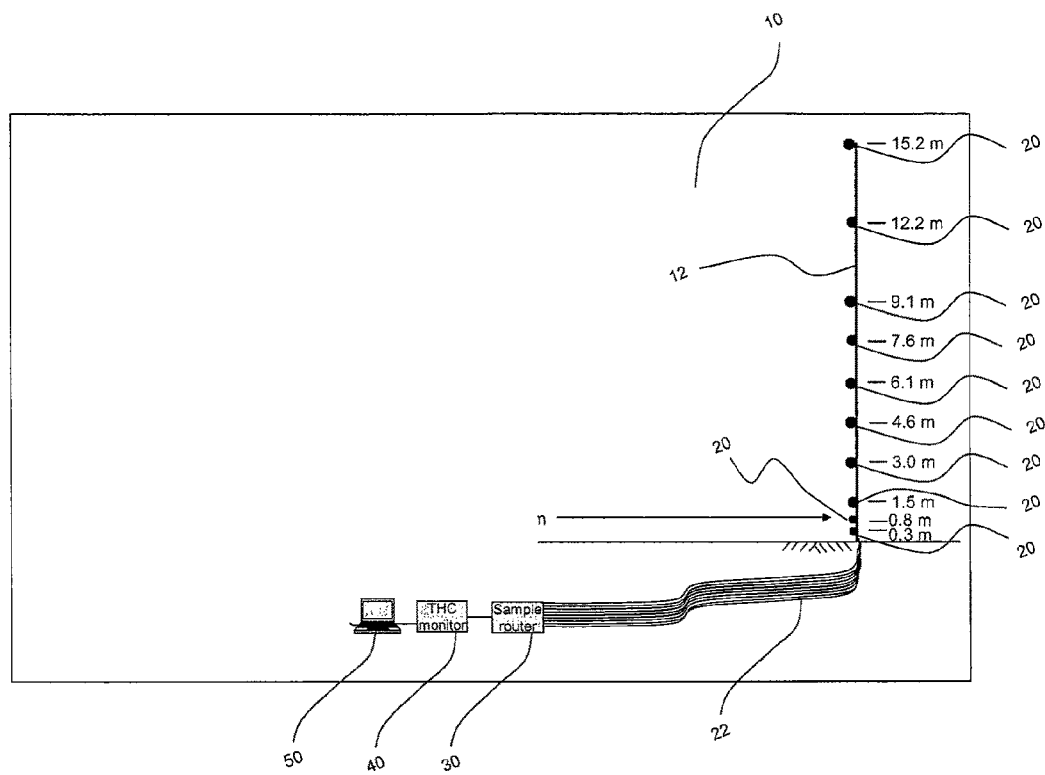
FIG. 1 is a schematic illustration of a sampling system.

FIG. 1 illustrates a sampling system 10 for obtaining air samples, measure emission concentrations in the air and quantifying an emission source. The sampling system 10 can have a tower 12 containing a number of sampling points 20. Each sampling point 20 can be at a different vertical height and in one aspect, all of the sampling points 20 are vertically aligned on the tower 12. Each sampling point 20 can have a sampling tube with an inlet of the sampling tube1 at the sampling point 20. The sampling tubes 22 can be routed to a sample router device 30 that selectively supplies the air samples taken at the sample points 20 to an emission monitor 40, such as a THC monitor, for measuring a concentration of one or more emission in the air, such as an air contaminant, etc. The emission monitor 40 can be operatively connected to a data processing system 50, such as a personal computer, to receive information collected/recorded by the emission monitor 40 from the sampling points 20 on the tower 12. Although FIG. 1 illustrates the sampling points 20 being vertically aligned, in some aspects the sampling points 20 may vary in horizontal positioning so that they are not necessarily vertically aligned.

In operation, the sampling system 10 can be installed with the tower 12 and the sampling points 20 positioned at a desired location for a period of time. During this period of time air can be drawn in through the sampling points 20 routed through the sampling tubes 22 and directed to the emission monitor 40 by the sampler router device 30. The measurement of the emission in the sample can then be taken by the emission monitor 40 and provided to the data processing system 50 where the emission reader can be logged and associated with the sampling point 20 it was taken from and the time it was taken. In one aspect, the travel time of the air as it is routed through the tubing 22 can be taken into account to determine the time the air was taken at the sampling point 20. In a further aspect, the distance to the source and the approximate travel time of the air from the source to the sampling point 20 can also be taken into account. Over the period of time, numerous data can be collected indicating concentration levels of emission at the various sampling points 20 at various times.

In another aspect, open-path gas detectors could be provided at each of the sampling points 20 to obtain emission concentration measurements at the sampling points 20. Open-path gas detectors typically use a laser source to direct a laser beam through a path to a receptor (in some cases they may use a mirror to reflect the laser back to the receptor). Based on the absorption of the laser by gas in the path of the laser, the open-path gas detector can be used to detect the presence of and the concentration of specific emissions.

In some cases, the gap the open-path gas detector is monitoring may be 6 feet or greater resulting in the sampling point where the emission concentration measurements being measured to be a relatively large sampling point.

Figure 2:
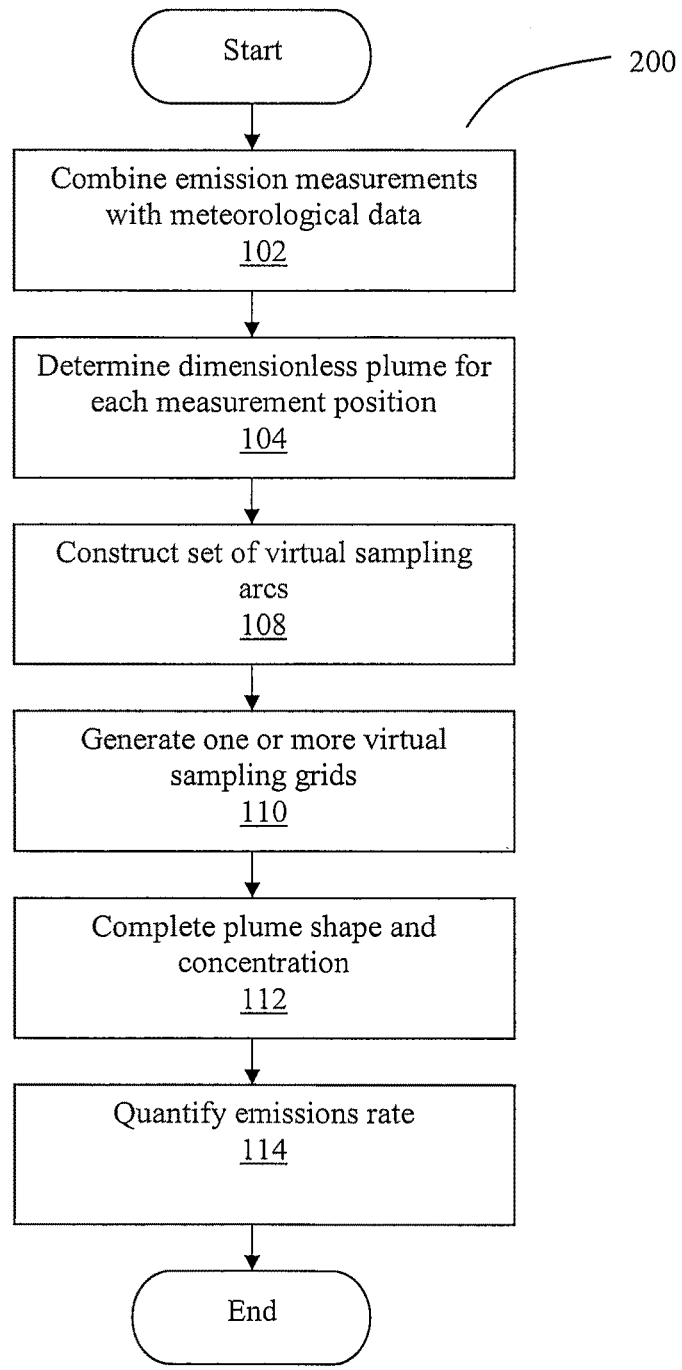
FIG. 2 is a flowchart illustrating a method for quantifying an emission source.

FIG. 2 illustrates is a flowchart illustrating a method for quantifying an emission source using samples obtained of the emission in the air, such as by using the sampling system 10 shown in FIG. 1. The method 100 starts and at step 102 emission concentration data regarding emissions in the air is obtained by the sampling system 100 and is combined with wind speed and direction data related to the emission concentration data. The combined data is used to approximate dimensionless plume data for each sample points 20 on the tower 12 in the sampling system 10 at step 104. Each sampling point 20 on the tower 15 can be converted to a virtual sampling arc at step 108. Typically, a virtual sampling arc is determined for each sampling point 20 for a specific wind speed or relatively narrow range of wind speeds. At step 110, the virtual sampling arcs determined for the different sampling points 20 can be grouped into a number of virtual sampling grids. Typically, each virtual sampling grid will be associated with a specific wind speed or relatively narrow range of wind speeds. Using the virtual sampling grids, at step 112, the overall plume shape can be completed. At step 114, a source emission rate for the emission source can be determined.

After the method 100 starts, measured emission concentrations in the air are combined with representative wind speed and direction data in a mathematical manipulation at steps 102 and 104 that produces dimensionless plumes viewed from the perspective of each measurement position. In the context of the present description, an emission plume means or refers to a column or aggregation of the emitted material which moves through the air. Plume may also refer more generally to a column of a fluid moving through another fluid. Several effects control the motion of the fluid, including momentum, buoyancy, density difference, etc. A log of wind speeds and directions are kept, from which a previous wind speed measurement and a corresponding wind direction measurement may be selected based on the air sample propagation time delay down a corresponding sampling tube 22, sampler routing device 30, and possibly the emission monitor 40. The emission concentration measurements can be averaged during an interval of sampling time to reduce signal noise and possibly analog to digital conversion errors. For example, measurements can be made at a frequency of 500 readings per second collected and averaged over the 10 second period. Emission concentration can be measured in parts-per-million (ppm).

In tracking emission sources an accurate characterization may be needed of air movement (wind driven) driving emission plumes from emitting sources to the sample points 20. In accordance with an embodiment of the invention, wind speed and wind direction are not necessarily assumed to be constant. Wind speed and wind direction can be measured at each air sample inlet 20, a reduced number of locations or even at a single representative location. Following the measurement of wind velocity characteristics such as, but not limited to, wind speed and wind direction, the wind characteristics can be correlated with the corresponding emission concentration measurements performed by the emission monitor 40 and provided to the data processing system 50. Correlating wind characteristics can take into account air sample travel time along the sampling tubes 22 from the sample points 20, and time of travel over the area of interest.

The wind speed and direction is not stable over time and can vary second to second moving a volume of air along a nonlinear path from the emission source to the sample tower 12. Obstructions such as land topography and buildings can cause wind to be non-linear, and knowledge of the geometry of such obstructions can improve the tracking of the trajectory of the air. Accordingly, wind speed and wind direction estimates are related to individual readings from the emission monitor 40.

A higher level process may be used to account for the wind variability by back tracking the nonlinear path of a volume of air from the sampling points 20 back to the emission source, by stepping backward in time and outward in space away from the sampling point 20 adjusting the path and concentration with each step for the changing wind conditions (note concentrations would be adjusted to reflect the dispersion that occurs as the plume travels down wind). Each emission concentration measured by the emission monitor 40 can take into account the degree to which changes in wind velocity have affected the air sample traversing a path outward and up-wind from the sampling point 20.

Alternatively, a representative wind velocity can be used wherein the non-linear path of air from an emission source to the sampling tower 12 can be replaced with a linear vector which estimates the average wind (velocity) speed and wind direction during the time of travel of the air from the emission source to the sampling point 20 measuring the emission concentration in the air. A measure of the standard deviation of wind speed and wind direction can also be calculated to provide an estimate of the accuracy of the assumption of linearity of the non-linear flow path. The linearity assumption can have more error at low wind speed because of longer averaging times and possibly due to a more unstable direction of flow of the wind (i.e. low speed wind may be subject to more radical changes in direction than high speed wind. In addition the travel time, which is calculated as the distance over wind speed, increases dramatically as a function of reciprocal wind speed and at low speeds (i.e. air moving at low speed takes much longer to get to the sampling point 20 and results in a longer averaging time substantially equal to the traveling time). The result of standard deviation calculation is used to filter out readings of the analysis that occur when the wind direction shifts too much for an accurate prediction of the flow path. This technique identifies wind data that accurately predicts wind effects and eliminates data that does not. Accurate low wind data may be very valuable in locating emission sources at great distances if the wind direction is stable. With knowledge of the geometry of the topography, buildings and other obstacles, the trajectory of the emission plume can be assumed linear and corrected for movement around obstacles.

An adjustment can be made for the time of travel of the air sample from the sampling point 20 down the corresponding sampling tube 22 through sample router 30 and to the emission monitor 40.

The measured emission concentrations at each sampling point 20 can be combined with the determined representative wind speed and wind direction associated with when that measurement of the emission concentration was taken. In one aspect, there is preferably a number of measured emission concentrations for a representative wind speed and wind direction and these measured emission concentrations can be averaged (or a median taken) to determine an emission concentration associated with the representative wind speed and wind direction. By grouping these emission concentrations with their associated representative wind speed and wind direction a dimensionless plume can be constructed.

At step 108 of the method 100, the data obtained from each sampling points 20 can be converted into one or more virtual sampling arcs using the distance of the sampling points 20 to the emission source. Typically, each generated virtual sampling arc will be for a specific wind speed or a relatively narrow range of wind speeds.

Figure 3:
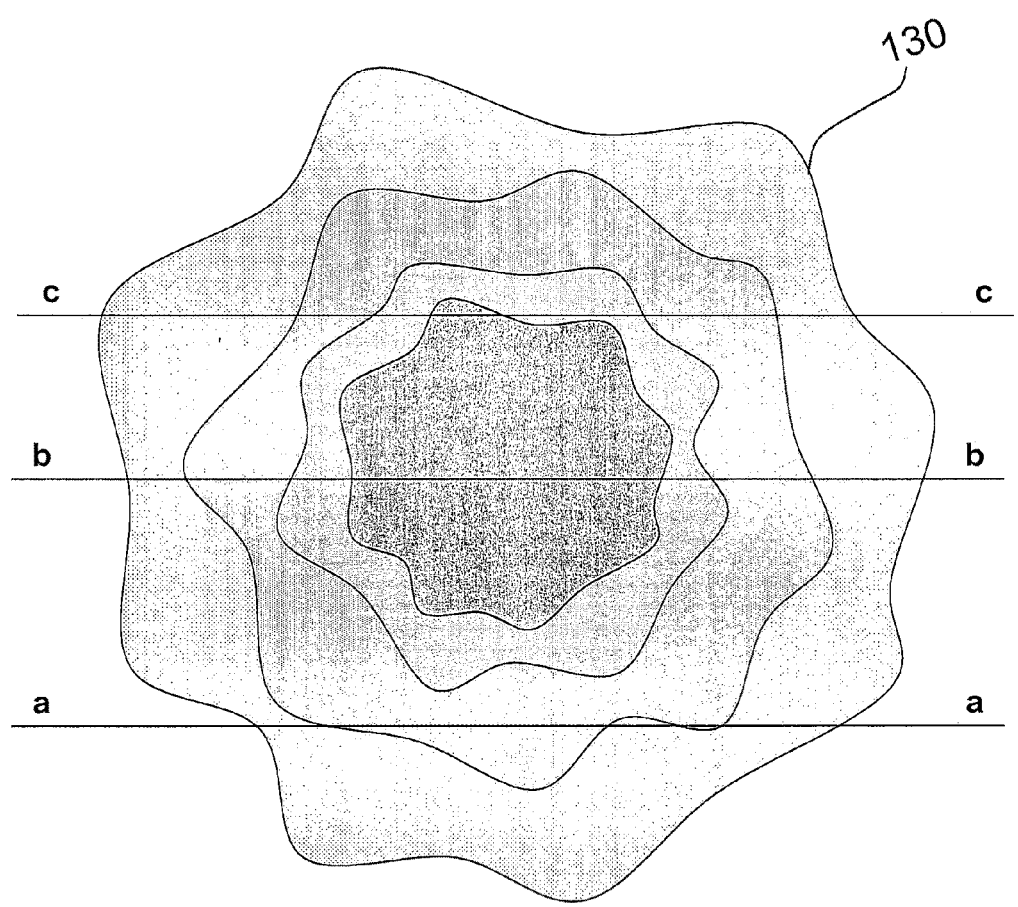
FIG. 3 is a schematic illustration of an emission plume.

A single sampling point 20 on the tower 15 of the sampling system 10 can be represented as a virtual arc of measurement positions that will provide concentration measures at a constant elevation. The emission concentration measurement obtained at a virtual measurement position can be an average of the emission concentration measurements taken at that virtual measurement position. This virtual arc will intercept a plume in a horizontal line for a given wind speed. This line can be at a different location on the plume if the plume elevation changes as a result of different wind speeds (due to buoyancy or momentum. etc.). FIG. 3 illustrates an emission plume 130 with three horizontal lines A, B and C. passing through different portions of the emission plume 130. Each line A, B, C represents a virtual arc taken from a single sampling point 20 at a specific vertical position on the tower 15 of the sampling system 10. Each line A, B, C was taken at a different wind speed; line A represents a virtual arc taken by the sampling point 20 at a first wind speed, line B represents a virtual arc taken by the same sampling point 20 at a second wind speed and line C represents a virtual arc taken by the same sampling point 20 at a third wind speed. As can be seen in FIG. 3, the portion of the emission plume 130 that is measured by a sampling point 20 can vary depending on the wind speed.

Figure 4:
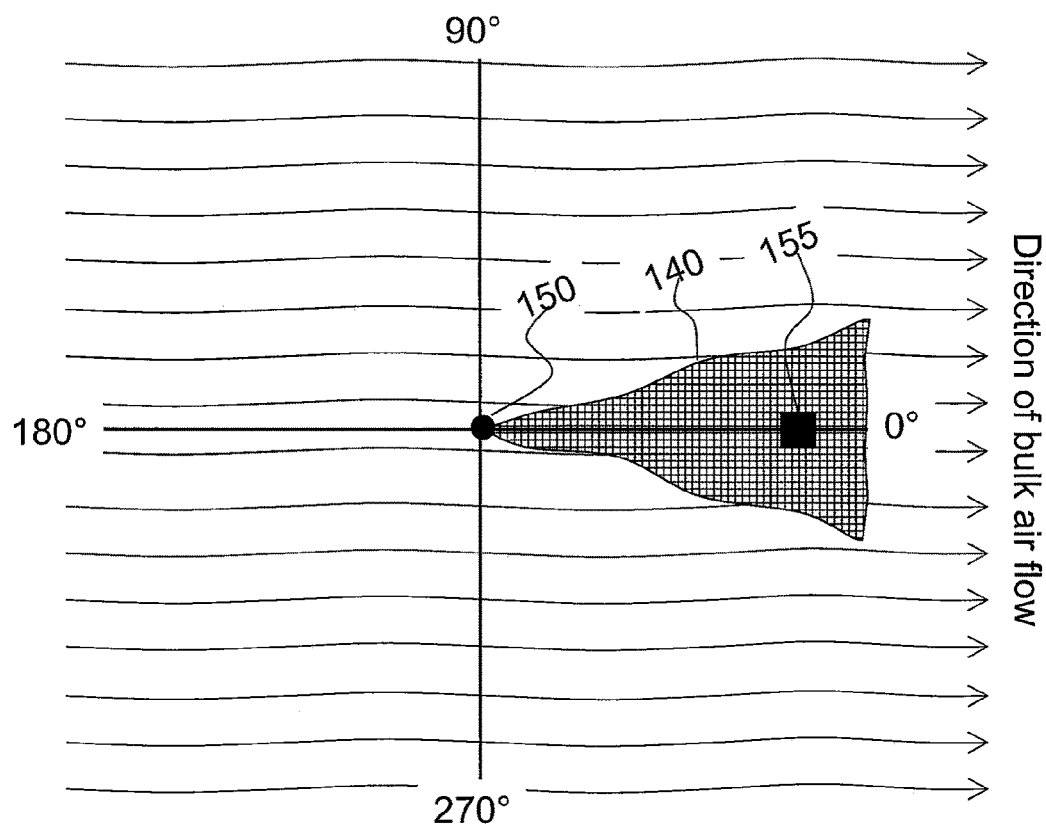
FIG. 4 is a schematic illustration of an emission source and a measuring point plotted on a polar coordinate system.

FIG. 4 illustrates an emission source 150 in relation to a measurement position 155 with an emission plume 140 originating from the emission source 150. The emission plume 140 is carried along with the bulk airflow (i.e. the wind). The measurement position 155 can be the tower 15 of the sampling system 10 shown in FIG. 1. A polar coordinate axis (θ, r) in plan view can be used with the origin at the emission source 150 and the zero (0) degree axis aligned with a direction of the bulk air flow (i.e. the wind), which is also pointed directly at the measurement position 155. The measurement position 155 is shown positioned in the emission plume 140 originating from the emission source 150 because the emission plume 140 will be carried along by the bulk airflow.

Figure 5:
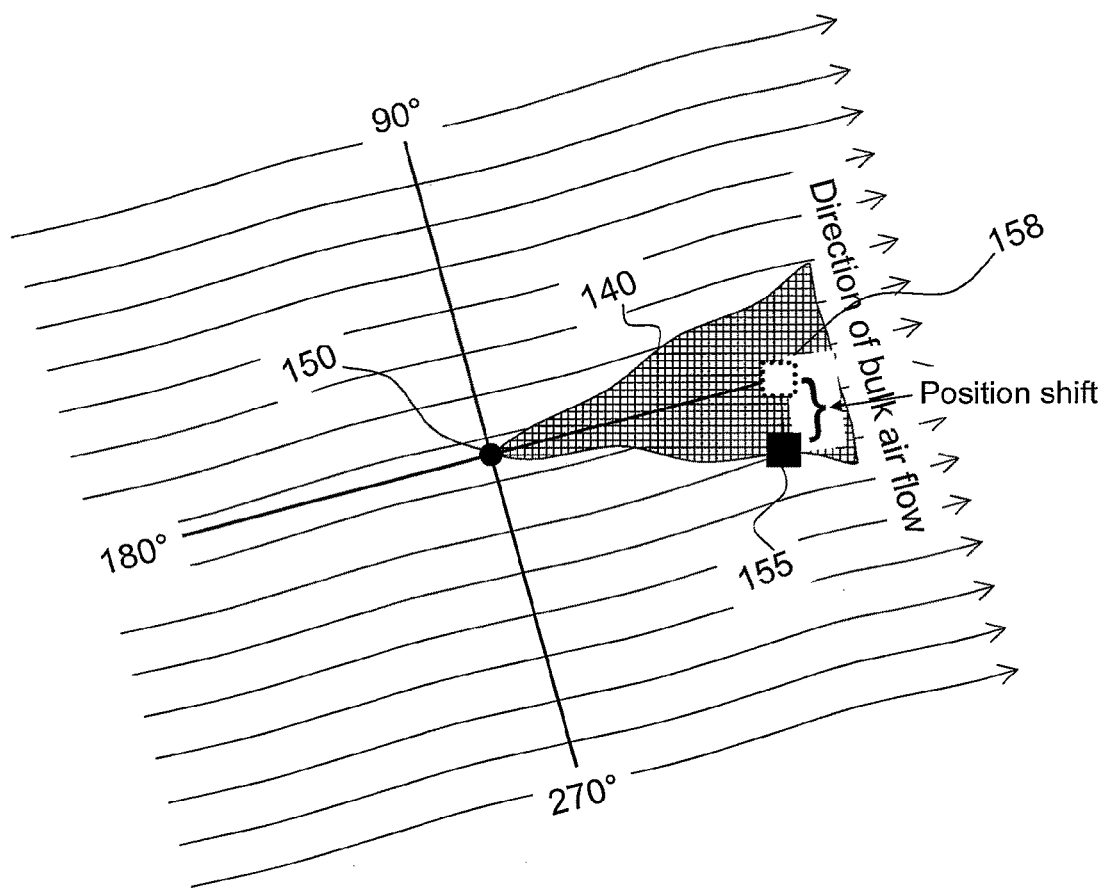
FIG. 5 is a schematic illustration of the emission source and the measuring point of FIG. 4 with a different direction of bulk air flow.

FIG. 5 illustrates the emission source 150 and the measurement position 155 when the direction of the bulk air flow has shifted (i.e. the wind has changed direction). By keeping the zero (0) degree axis aligned with the direction of the bulk air flow in FIG. 5, the relative position of the measurement position 155 of air concentrations sifts relative to the upwind emission source 150. FIG. 5 shows the measurement position 155 being at a slight negative angle relative to the zero (0) axis line. While neither the emission source 150 nor the measurement position 155 have physically moved, their positions have changed relative to the bulk air flow (which carries the emission plume 140). The magnitude of the relative position shift is directly related to the angle of the bulk airflow (i.e. the wind) direction shift and the distance between the emission source 150 and measurement positions 155. The virtual measurement position 158 indicates where the measurement position 155 was relative to the bulk airflow in FIG. 4. The measurement position 155 is now measuring the concentration of emission in the emission plume 140 at a different point in the emission plume 140.

Figure 6:
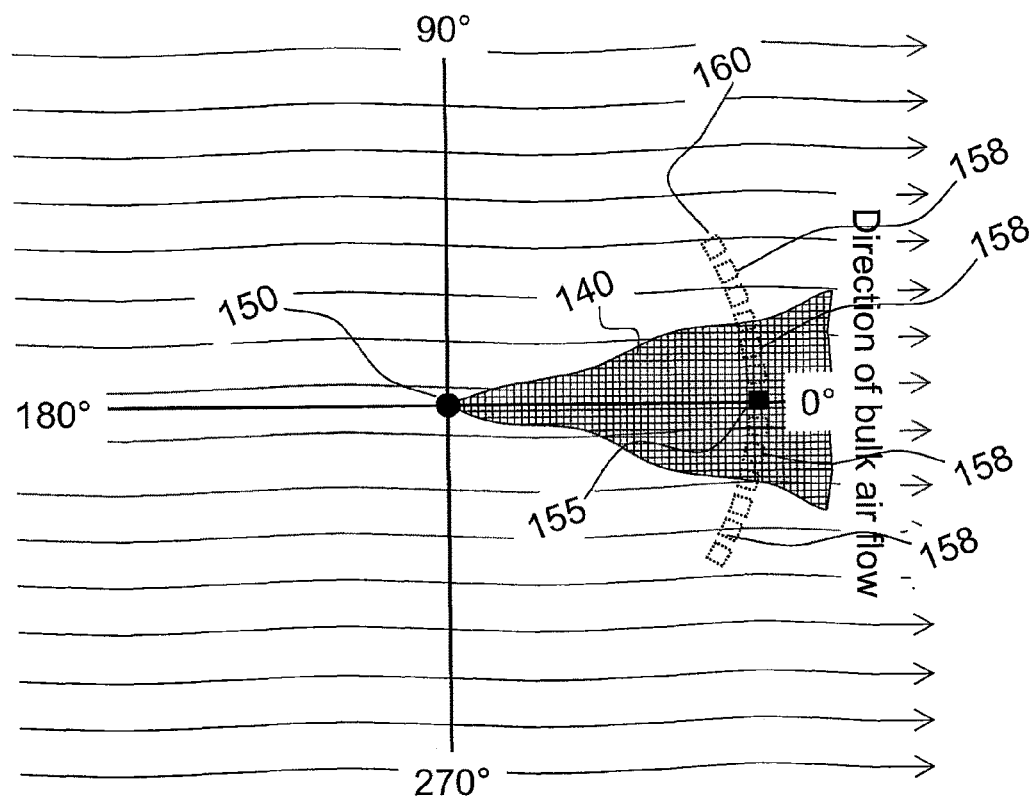
FIG. 6 is a schematic illustration of the emission source and the measuring point of FIG. 4 with a number of virtual measuring points indicated.

With continued changes in the direction of the bulk airflow, a single measurement position 155 can be used as a series of virtual measurement positions 158 through the emission plume 140 in a radial arc with the center of the arc at the emission source 150, as shown in FIG. 6. With enough changes in wind direction and measurements of emission concentrations at the measurement point 155 a virtual sampling arc 160 can be determined. This virtual sampling arc 160 can have measured emission concentrations of the emission plume 140 along the virtual sampling arc 160 for a specific wind speed or relatively narrow range of wind speeds. In one aspect, the measured emission concentrations along the virtual sampling arc 160 can be an average of measured emission concentrations at each virtual measurement positions 158.

The positions of the virtual measurement positions 158 in the virtual sampling arc 160 can be determined using the angular shift in the direction of the bulk airflow. The conversion of an angular shift in the direction of bulk airflow to a scalar length along the arc between virtual measurement positions 158 is the arc length along a curve of a circle centered at the emission source 150 for a point emission source:

$$\text{Length}_{LARC} = \frac{AngularWidth}{360°} \times cirumference \quad [1]$$
$$= \frac{AngularWidth}{360°} \times 2 \times \pi \times r$$

wherein $\text{Length}_{LARC}$ is the scalar length along the arc, the angular width is the change in the angle of the direction of the wind and r is the distance between the emission source 150 and the measurement position 158.

In this manner, a virtual sampling arc 160 can be determined where an emission concentration has been measured for each of the virtual measurement positions 158 (or points) making up the virtual sampling arc 160.

Referring again to FIG. 1, one or more virtual sampling arcs 160 can be determined for each of the sampling points 20 on the tower 15 in this manner. Typically, each virtual sampling arc 160 is associated with a specific wind speed or relatively narrow range of wind speeds.

Figure 7:
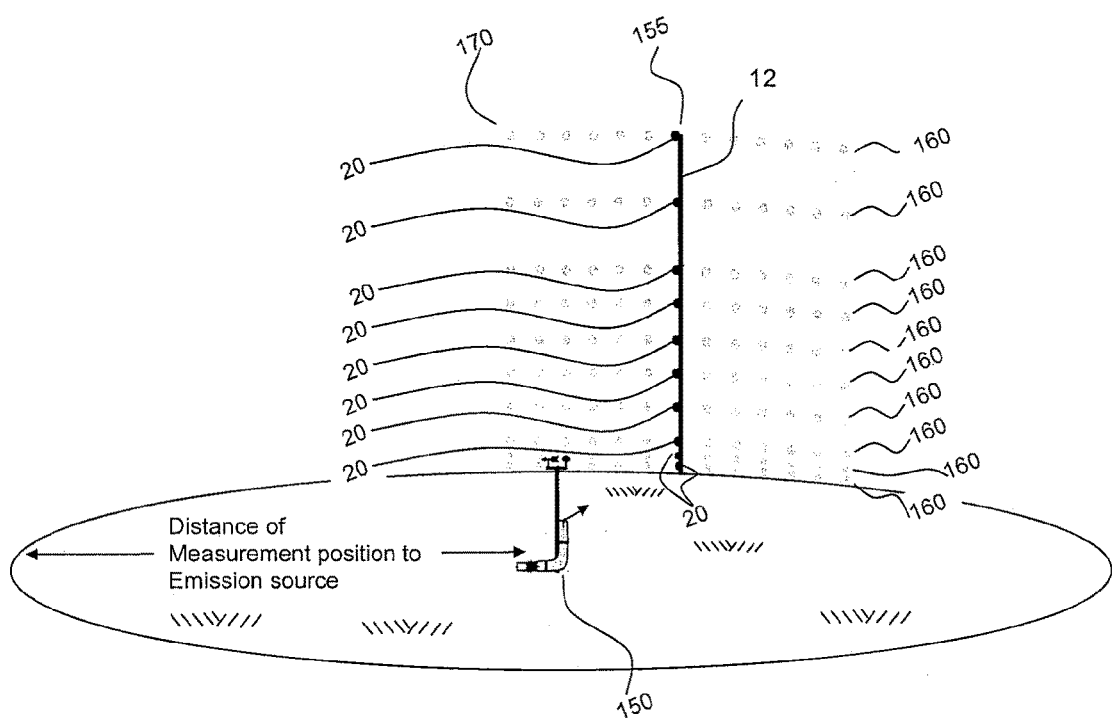
FIG. 7 is a schematic illustration of a virtual sampling grid.

Referring again to FIG. 2, once the virtual sampling arcs have been generated at step 108, the method 100 can move on to step 110 and the generated virtual sampling arcs determined at step 108 can be grouped together to form one or more virtual sampling grids. FIG. 7 illustrates a virtual sampling grid 170. Typically, each virtual sampling grid 170 will be made up of measured emission concentrations at a specific wind speed or relatively narrow range of wind speed. The multiple sampling points 20 of the sampling system 100 shown in FIG. 1 can be used to form the virtual sampling grid 170 of emission concentration measurements using the measurement position 155. The virtual sampling grid 170 can follow an arc that is centered on the emission source 150 location.

The virtual sampling grid 170 can be determined using the virtual sampling arcs 160 determined for each sampling point 20 for a specific wind speed or range of wind speeds at step 108 of method 100 shown in FIG. 2. Each virtual sampling arc 160 is associated with its corresponding sampling point 20 on the tower 15 and can be placed in the virtual sampling grid 170 at the vertical level of the sampling point 20. By applying the determined virtual sampling arc 160 for each sampling point 20 at a specific wind speed or range of wind speeds, the virtual sampling grid 170 for the specific wind speed or range of wind speeds, can be created, with each point on the virtual sampling grid 170 having an emission concentration that has been measured at that position.

Referring again to FIG. 2, in this manner, set of virtual sampling grids 170 can be constructed at step 110, with each virtual sampling grid 170 associated with a wind speed or range of wind speeds and each point in the virtual sampling grid 170 has an emission concentrations associated with it that has been measured at that point.

Optionally, at step 112 the overall emission plume shape and the concentration profile of the emission plumes can be approximated by combining information from different sampling points 20 and virtual measurement positions 158 for the same emission plume. If the different sampling points 20 do not provide enough desired points on the virtual sampling grid 170 as shown in FIG. 7, emission concentrations measurements for point on the quasi radial virtual sampling grid 170 can be used to extrapolate and/or interpolate to approximate emissions concentrations at the desired points where there are no emission concentrations measurement or insufficient emission concentration measurements. In one embodiment, the emission plume shape and concentration profile can be interpolated and/or extrapolated from locations having measured emissions concentrations during the sampling period. Emission concentrations can be approximated for locations in the virtual sampling grid 170 where no emission concentration measurements were taken or not enough emissions concentrations were taking to provide a useful average. By interpolation/extrapolation using adjacent virtual measurement positions 158 having measured emission concentrations, emission concentrations for other points in the virtual sampling grid 170 can be approximated. For example, if there is measurement positions at two different elevations then the shape of the plume can be interpolated between the measurement positions. Additionally, if the highest or lowest sampling points 20 do reach the top/bottom of the emission plume, points above or below the sampling points 20 could be extrapolated from adjacent sampling points 20 using the measured emission concentrations at the adjacent sampling point 20.

In one embodiment, the emission plume shape and concentration profile can be extrapolated from a single sampling point 20 (and its associated virtual sampling arc 160). The emission plume can be broken down to concentric circle rings or some other assumed shape and the area or each ring calculated and the flux across each piece determined in order to integrate them to the total number.

Assuming a circular shape to the plume is just a method to extrapolate the measured concentration profile across one line of the emission plume to other areas of the plume and any known and appropriate shape can be assumed. This method can be effective even if the ground impinges on the lower part of the emission plume so that it cannot develop the actual circular shape. Basically, characterizing the top portion of an emission plume and assuming the bottom portion is the same can provide effective estimates of emission rate.

Referring again to FIG. 2, at step 114, the emission rate of the emission source can be quantified. The emission plume as measured by the sampling points 20 can be broken down to smaller manageable pieces and the flux per unit emission plume area analyzed across the pieces. An evaluation to determine which pieces belong to the overall plume or sub plumes can be done to total the overall emission rate of an emission source and the emission rate of sub sources within the overall plume.

Figure 8:
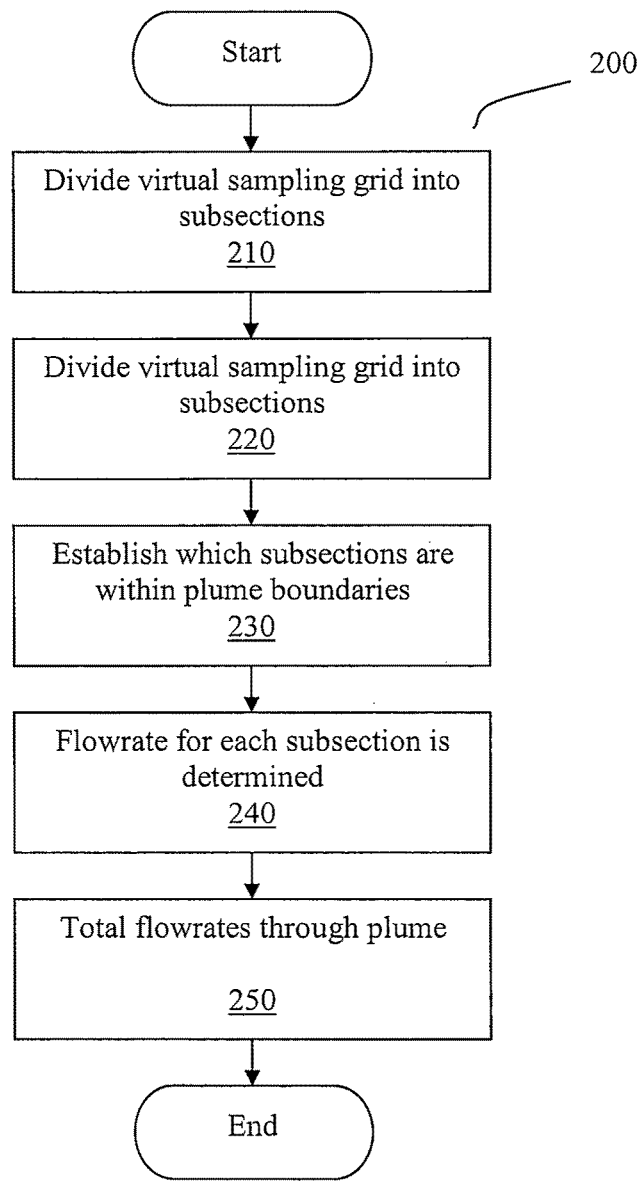
FIG. 8 is a flowchart illustrating a method of quantifying an emission source using one or more virtual sampling grids.

FIG. 8 is a flow chart illustrating a method 200 of quantifying an emission source in one aspect and can be used to perform step 114 of method 100 in FIG. 2. The method 200 starts and at step 210 a virtual sampling grid, determined at step 112 of the method 100 shown in FIG. 2, is divided into subsections. At step 220, the flux rate of the increased compound concentrations through each of the subsections is determined for different wind speeds. The increased compound concentration is the measured concentration less the concentration of that compound that normally occurs in that location. Using the flux rates determined for the subsections at step 220, the subsections that are within the emission plume boundaries are determined for the different wind speeds at step 230. At step 240, for each subsection, the flux rates determined for the subsection at step 220 are multiplied by the area of the subsections to determine a flow rate. At step 245, the flow rates determined for each of the subsections at step 240 are totaled to approximate the source emission rate. In this manner, the quantification of the emission rate can be approximated by calculating the flux of increased emission crossing the virtual sampling grid after dividing the virtual sampling grid into subsections. Because the measured emission concentrations in each virtual sampling grid which will vary depending on the wind speed, the method 200 can be performed for each virtual sampling grid that has be determined and is associated with a wind speed or range of wind speeds, allowing a separate quantification of a flow rate to be determined for each of the virtual sampling grids that were determined for a specific wind speed or relatively narrow range of wind speeds.

At step 210 the virtual sampling grids can be divided into subsections. If the sampling system 10 shown in FIG. 1 was used to sample the air and measure the emission concentrations, the vertical spacing of the subsections can be set by the vertical spacing of the sampling points 20 on the tower 15. The horizontal spacing of the subsections is set by the size of increments of wind direction on which the data is aggregated. The increments need to be small enough to accurately characterize the emission plume. The boarders of each subsection can be defined by half the distance to the adjacent subsection center. If there are no adjacent subsection, such as along the bottom of the virtual sampling grid, then the ground can be used as the border (or something just above the ground to take into account that there is little air flow along the ground). The top boundary of the subsections along the top of the virtual sampling grid positions is assumed as the same distance to the center of the subsections as the bottom boundary (this upper boundary can also be assumed based on an extrapolated emission plume concentration profile if the plume boundary extends above the virtual radial sampling grid).

The area of the each subsection can be calculated by height*width if the elements are rectangular as follows:

$$\text{Area}_{subsection} = \text{HEIGHT} \times \text{WIDTH} \quad [2]$$

At step 220, a flux value can be approximated for each of the subsections. The flux value can be approximated by multiplying the increased emission concentration (i.e. if the emission being measured is THC, the THC concentration less the background level of THC could be used for the increased emission concentration) by the wind speed as follows:

$$\text{FluxValue} = \text{IncreasedEmissionConcentration} \times \text{windspeed} \quad [3]$$

The units of this flux value is the amount of compound that is passing a unit area of the grid of virtual measurement positions during a unit of time, for example $$\frac{L}{(\min \times m^2)},$$

or $$\frac{L}{(hr \times m^2)}.$$

The area ($m^2$) in these formulas refers to the radial cross-sectional area of the emission plume.

At step 230, the boundary of the emission plume can be approximated. The boundary of the emission plume can be taken to be the point where the modeled flux breaks below some minimum flux level on either side of the emission plume peak. This allows the emission plume boundaries that exist within the background noise to be accurately predicted. A model is not fitted and the emission plume is considered not definable when the plume shape is not dominant above the background flux values.

After the boundaries of the emission plume are determined at step 230, the flow rate through each of the subsections can be approximated at step 240. The flow rate through each subsection can be determined by multiplying the flux value determined for the subsection at step 220 by the area of the subsection determined at step 210, as follows:

$$\text{FlowRate} = \text{FluxValue}_{SUBSECTION} \times \text{Area}_{SUBSECTION} \quad [4]$$

At the completion of step 230, the flow rates of the emission through each of the subsections should be approximated.

At step 245, the flow rates approximated for each of the subsections at step 240 can be totaled to determine the source emission rate. Using the emission plume boundary determined at step 330, the approximated flow rates through each of the subsections can be totaled across the emission plume boundary. The total flow rate through the emission plume boundary can provide an approximation of the emission rate for the emission source.

Referring again to FIG. 2, after step 114, with the emission source having been quantified, the method 100 ends.

Testing was conducted with a sampling device to quantify a known emission source with sampling positions at different heights used to construct a virtual sampling grid of virtual measurement positions. Natural gas was released at controlled flow rates and the resulting emission plume was characterized and the emission rate determined using the system and method outlined above.

Figure 9:
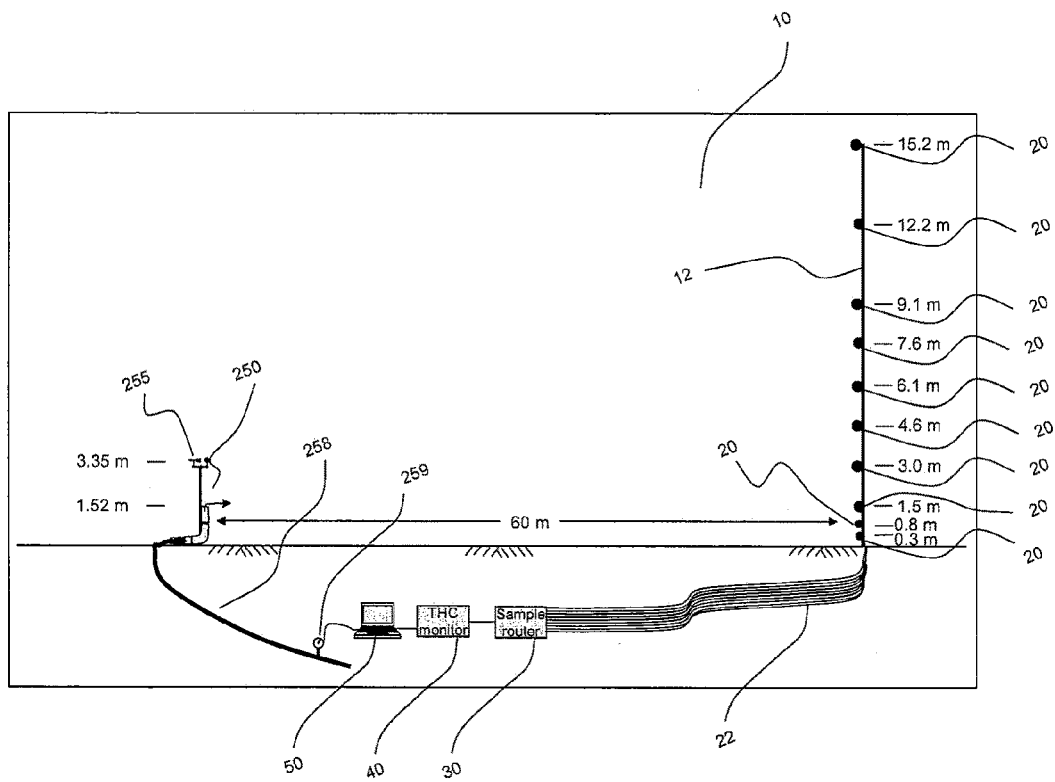
FIG. 9 is a schematic illustration of a testing apparatus for conducting exemplary testing of a known emission source.
Figure 10:
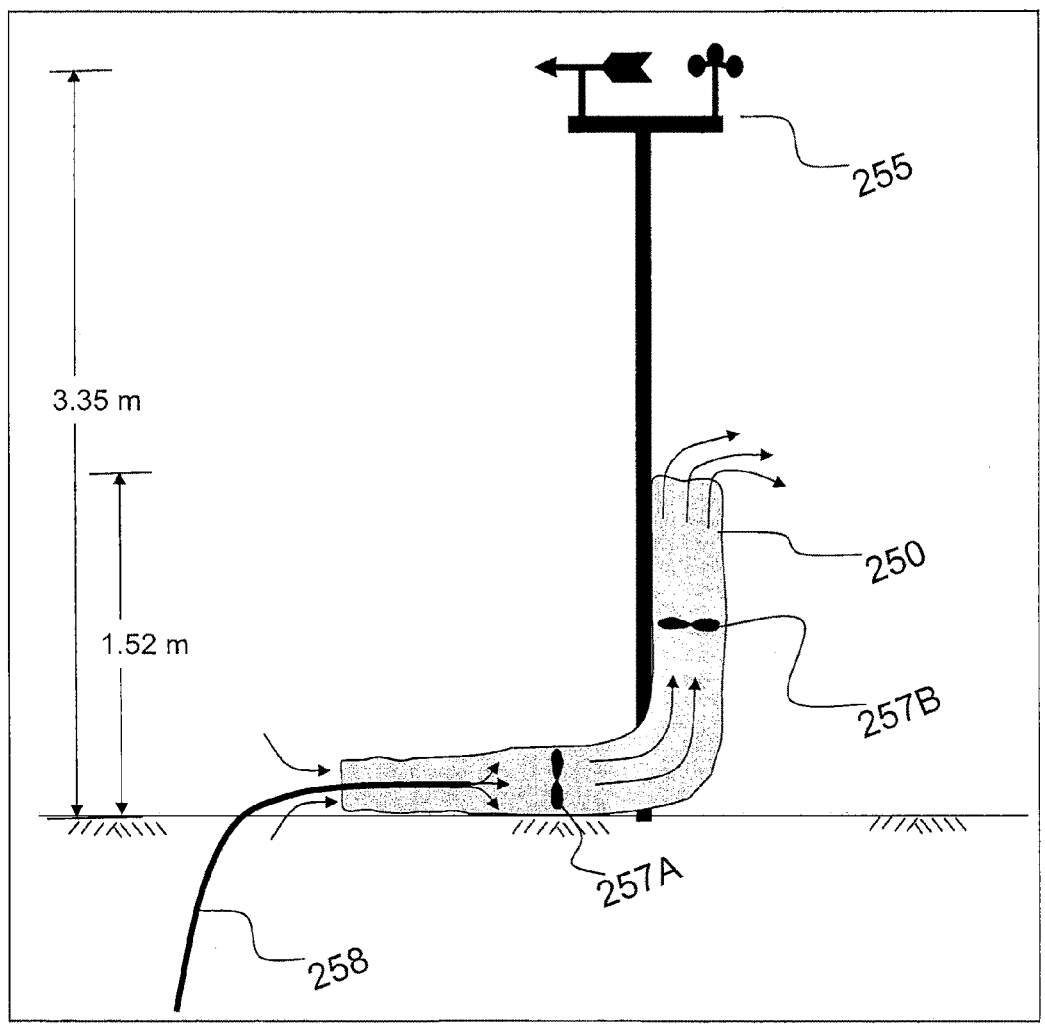
FIG. 10 is a schematic illustration of an emission source used for the testing apparatus of FIG. 9.

In a ten acre hay field an emission source 250, a wind monitor 255, and a sampling tower 12 were erected as shown in FIGS. 9 and 10. This study was set in southwestern Alberta which has predominant wind from the southwest. The sampling tower 12 was 15.2 m high with sampling points 20 positioned at the ten different heights shown. The sampling tower 12 was positioned 60 m away in the predominant downwind direction from the emission source 250 and the wind monitor 255. The emission source 250 is shown in more detail in FIG. 10 and consisted of a 2.5 in aluminum heating duct that was 150 mm in diameter with the end pointing upward at a height of 1.52 m off the ground. Two duct fans 257A, 257B were used to maintain a constant flow upward and entrain the natural gas released from a line 258 running from a gas supply (not shown) that is metered with a flow sensor 259 that has been calibrated with a bubble flow meter made by Gillian. This setup allowed the controlled emission plume to have a roughly constant exit velocity for different natural gas emission rates. Small diameter (¼ inch OD) polyethylene sample lines 22 connected the sample points 20 on the sampling tower 15 to a sample router 30 (200 m away) that constantly draws a sample from all of the sample points 20 and selectively channels one of the samples to an emission detector 40, in this case a flame ionization detector (Photovac microFID) providing a measure of total hydrocarbons (THC). In this way, one instrument was used to provide concentration measures from multiple locations. The data processing system 50 shown in FIG. 9 was used to control the sample router 30 and store data at a one second frequency from the emission detector 40, the wind monitor 255, and the flow meter 259 connected to the line 258.

Figure 11:
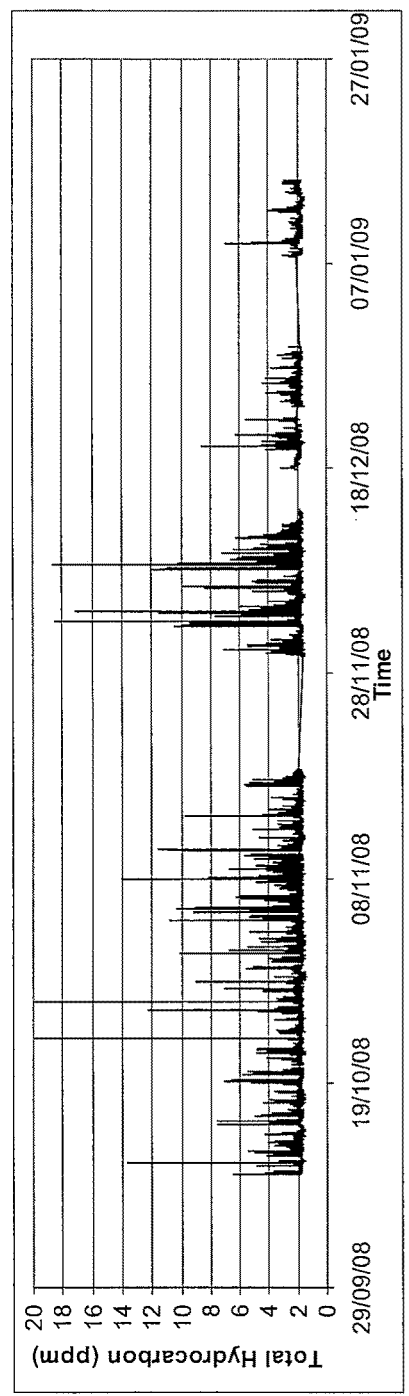
FIG. 11 is a plot of emission concentrations measured over time.
Figure 12:
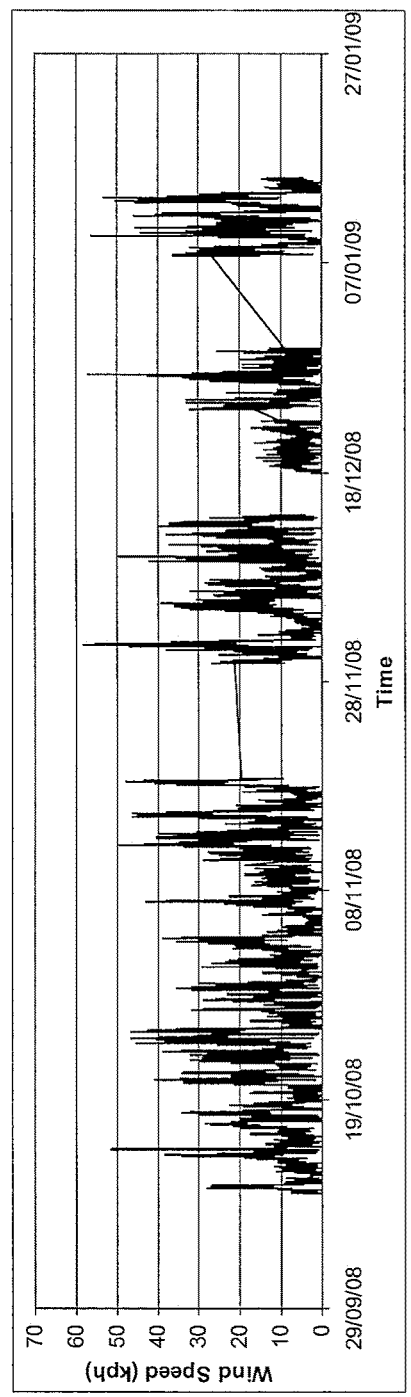
FIG. 12 is a plot of wind speed data collected over the same time period shown in FIG. 11.
Figure 13:
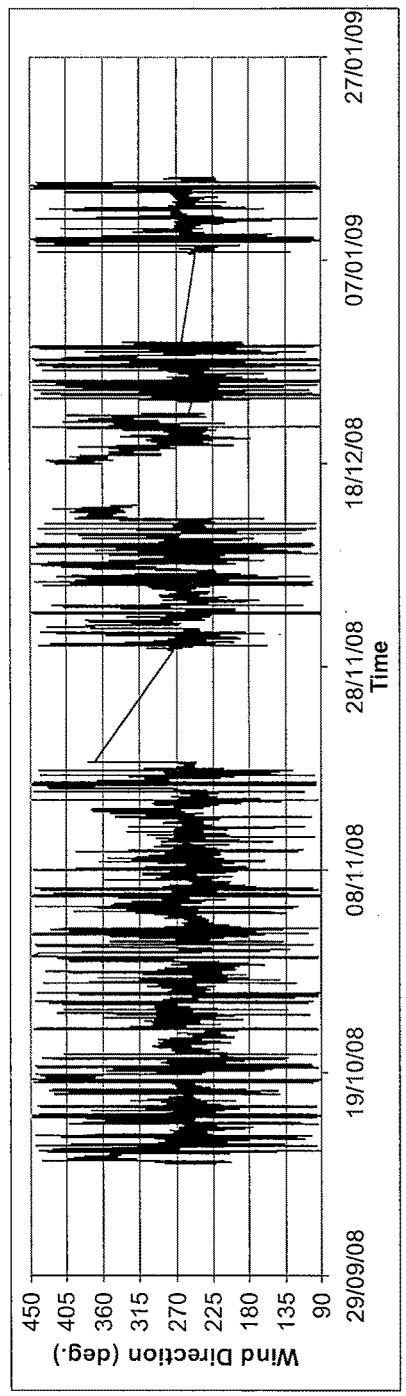
FIG. 13 is a plot of wind direction collected over the same time period shown in FIG. 11.
Figure 14:
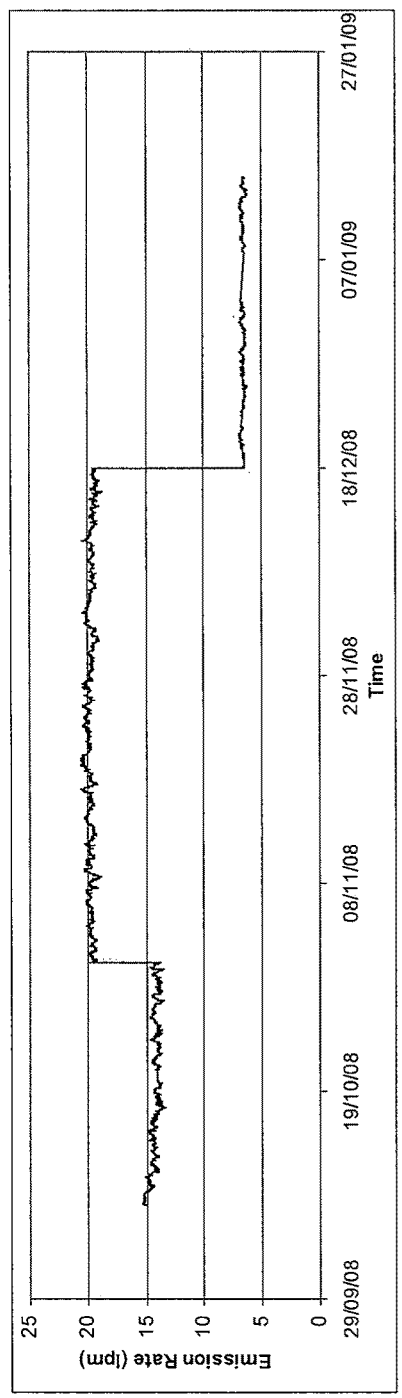
FIG. 14 is a plot of flow rate of emission from an emission source over the same time period shown in FIG. 11.

FIGS. 11 through 14 shows plots of the data collected during the study rolled up to a ten second average. There are periods of time when data was not available due to equipment malfunction. FIG. 11 shows the THC levels measured by the emission detector 40 through the study. FIGS. 12 and 13 show wind speed and direction measurements taken during the study. FIG. 14 shows a plot of output from the flow meter 259 measuring the flow rate of the controlled emission source 250 of natural gas released.

Figure 15:
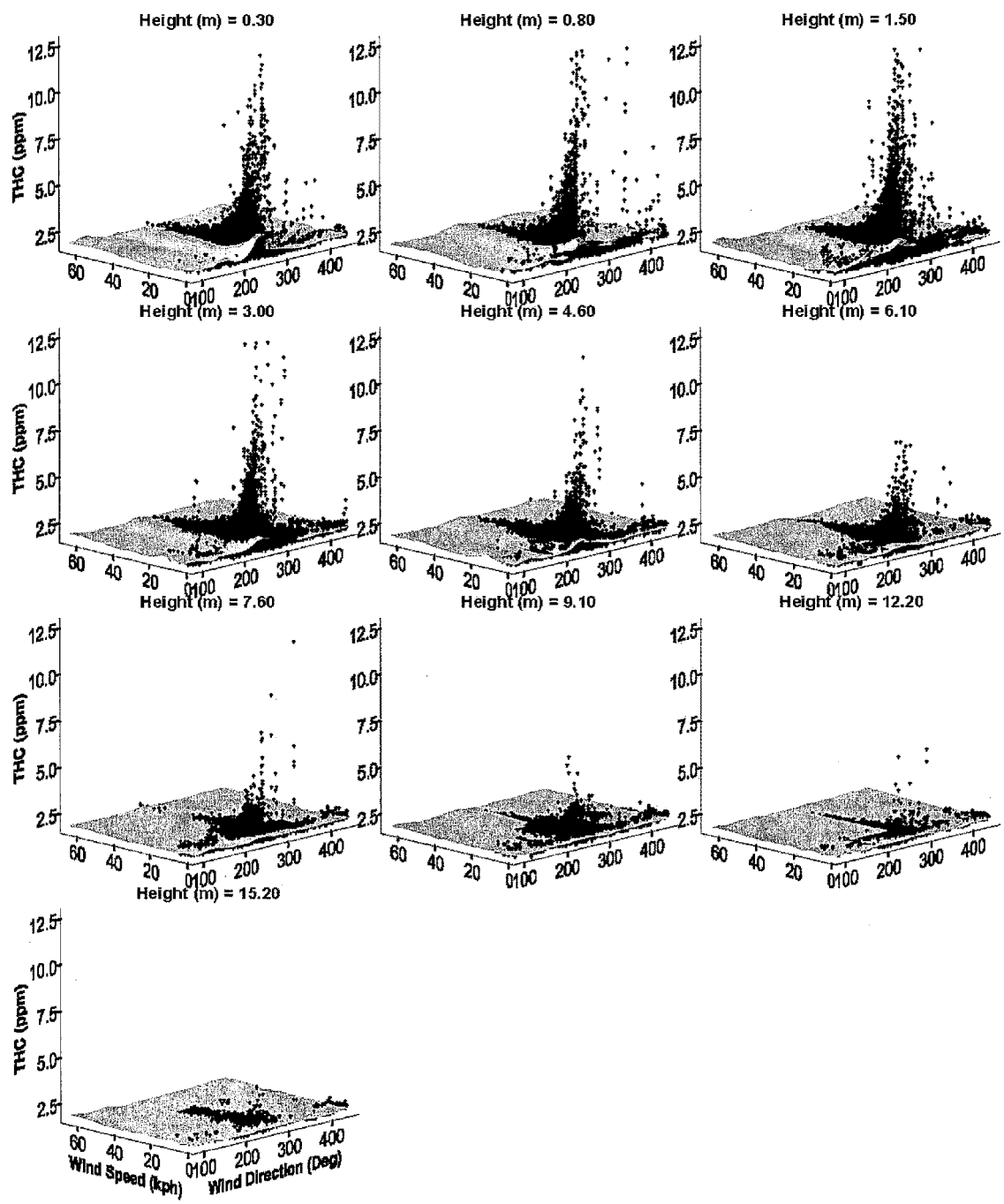
FIG. 15 is a set of plots of emission concentrations in relation to wind speed and wind direction.
Figure 16:
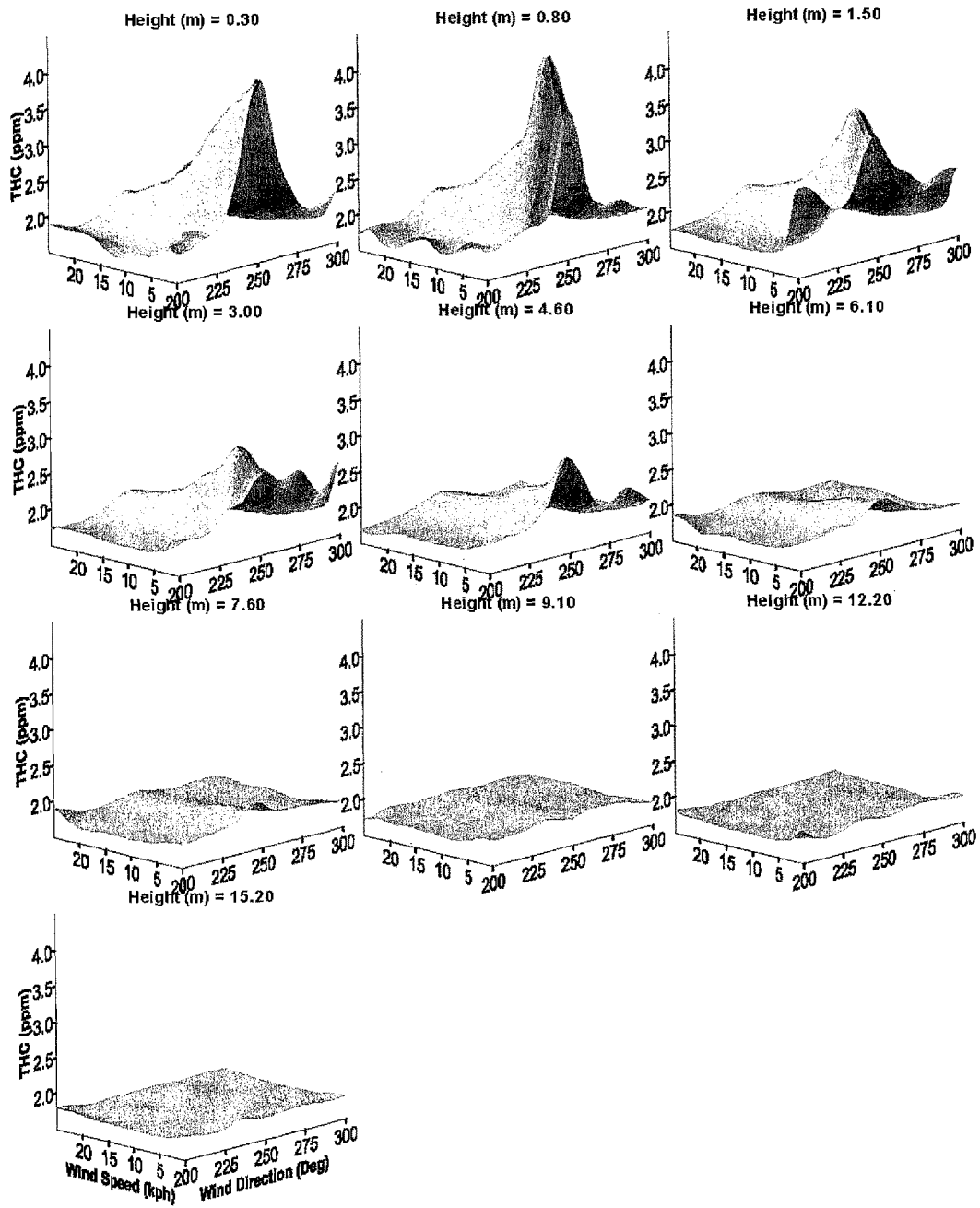
FIG. 16 is a set of plots of average emission concentrations in relation to wind speed and wind direction.
Figure 18A:
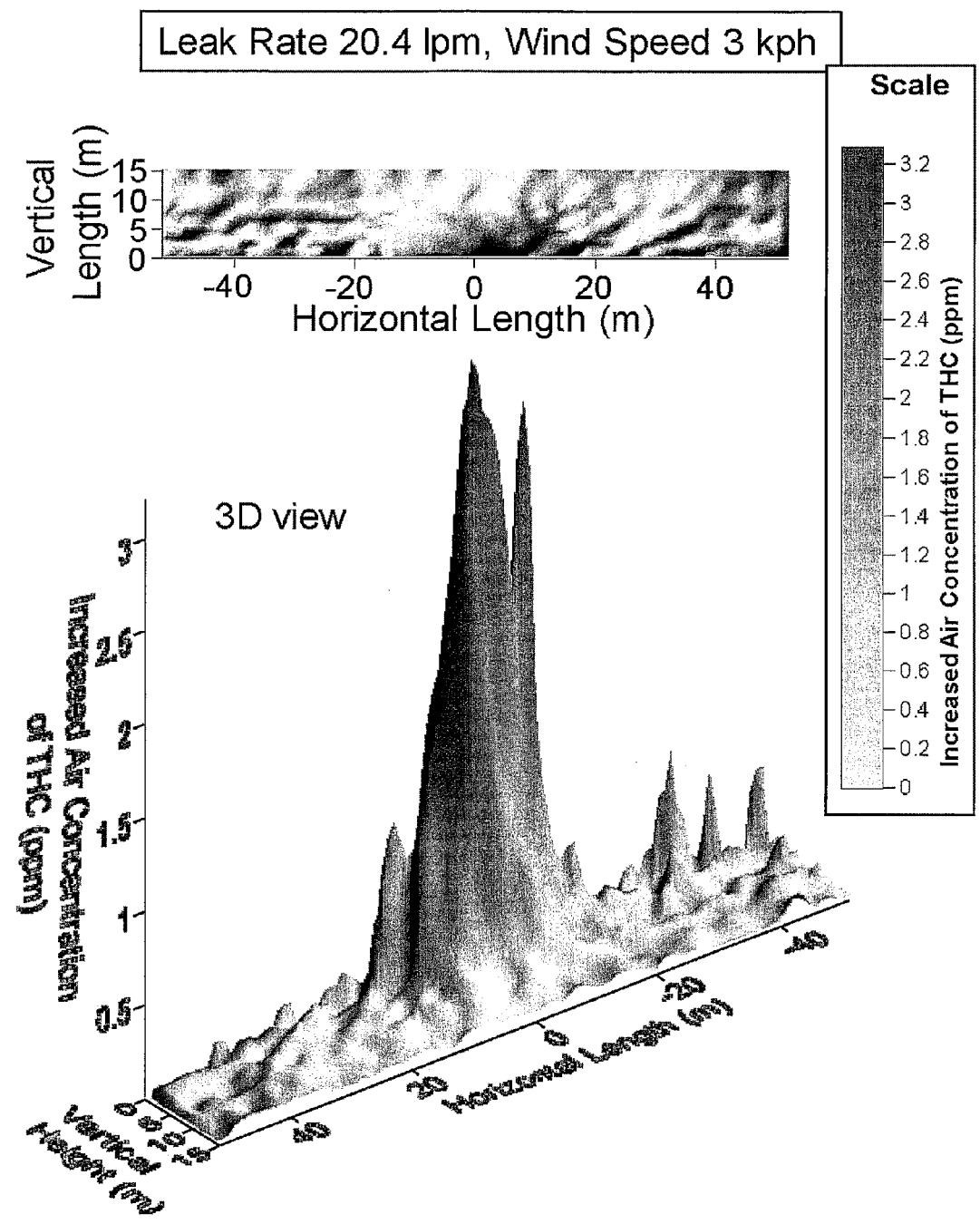
FIGS. 18, 19 and 20 are sets of plots of increased emission concentrations plotted against vertical and horizontal distances for different emission rates.
Figure 18B:
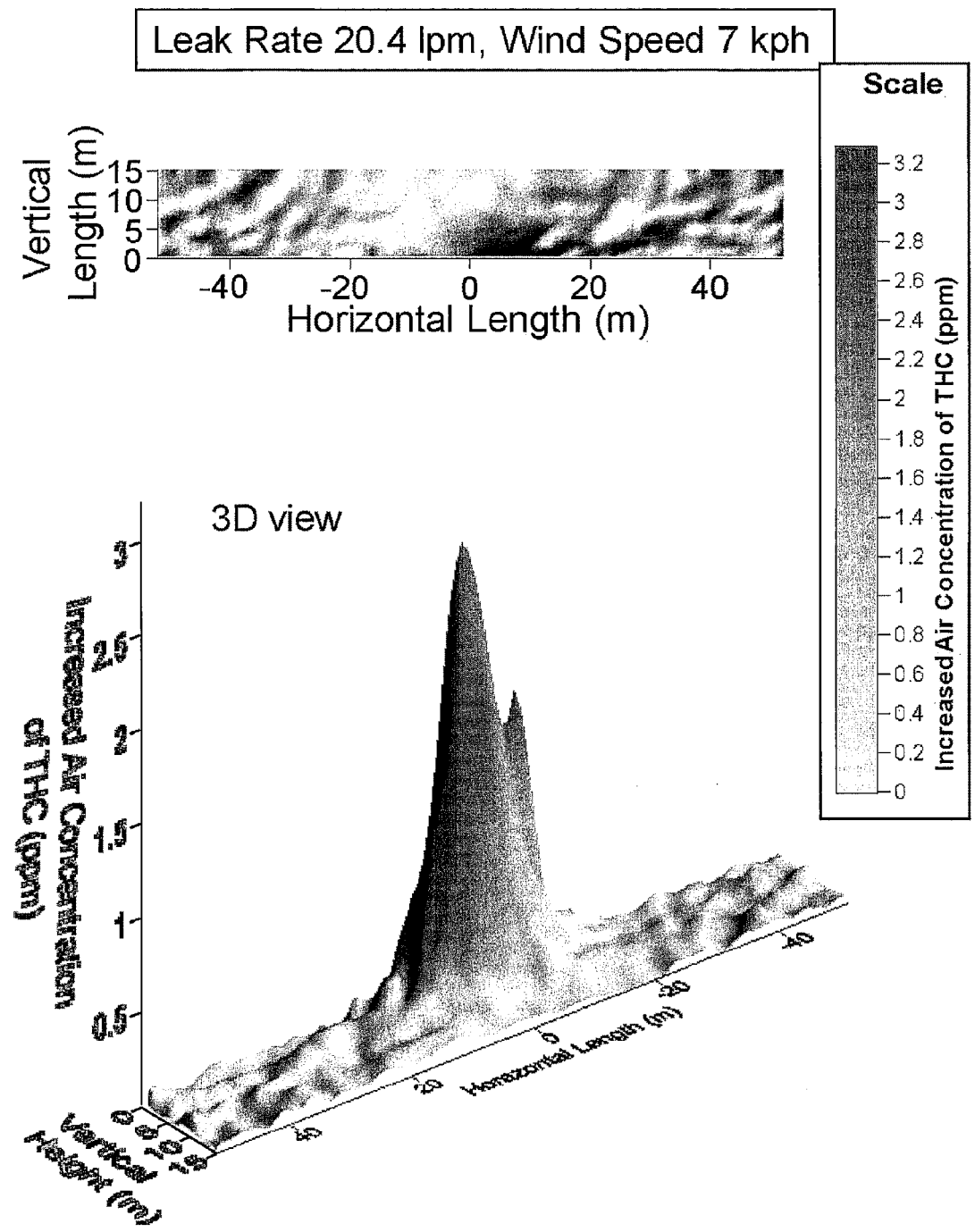
Figure 18C:
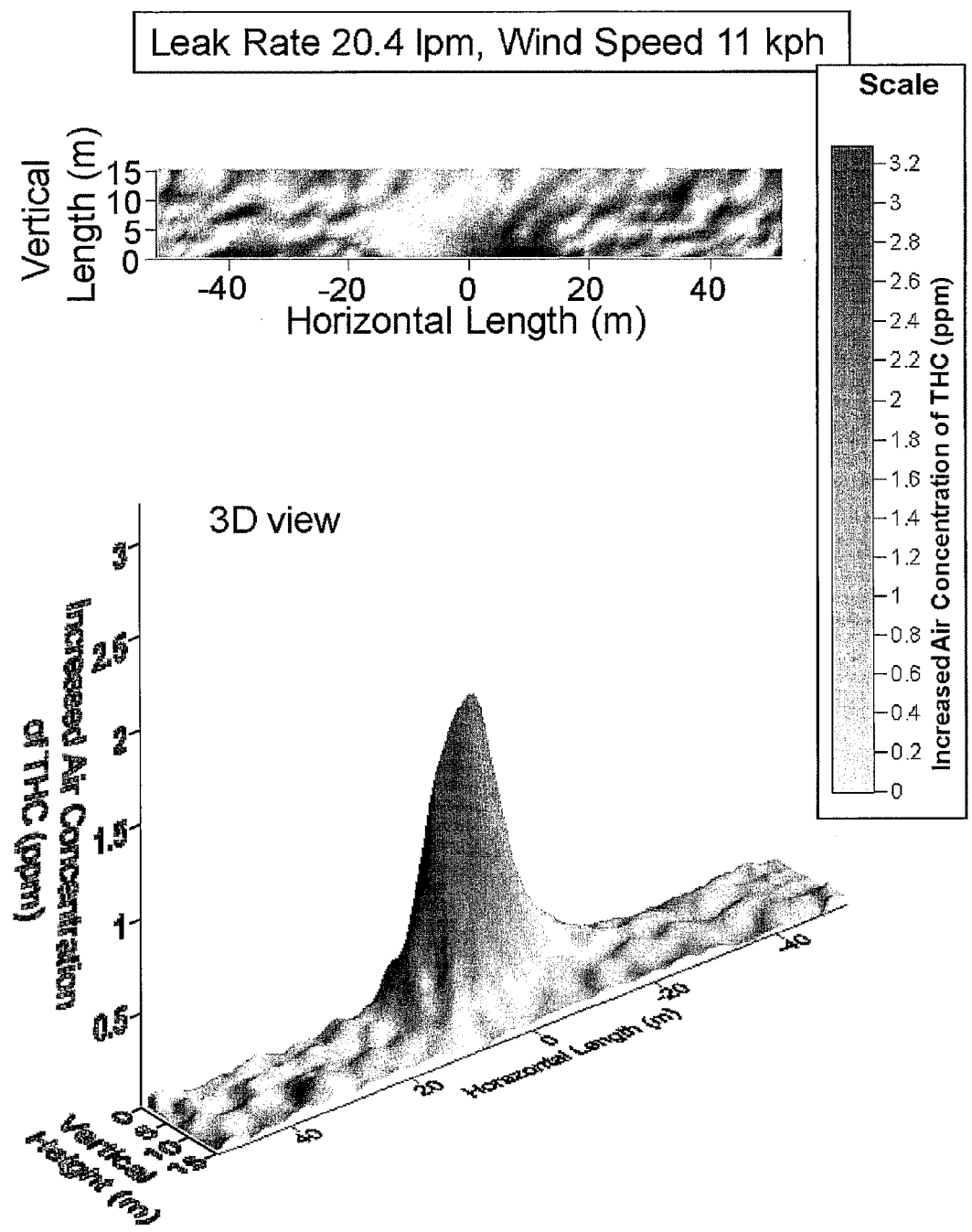
Figure 18D:
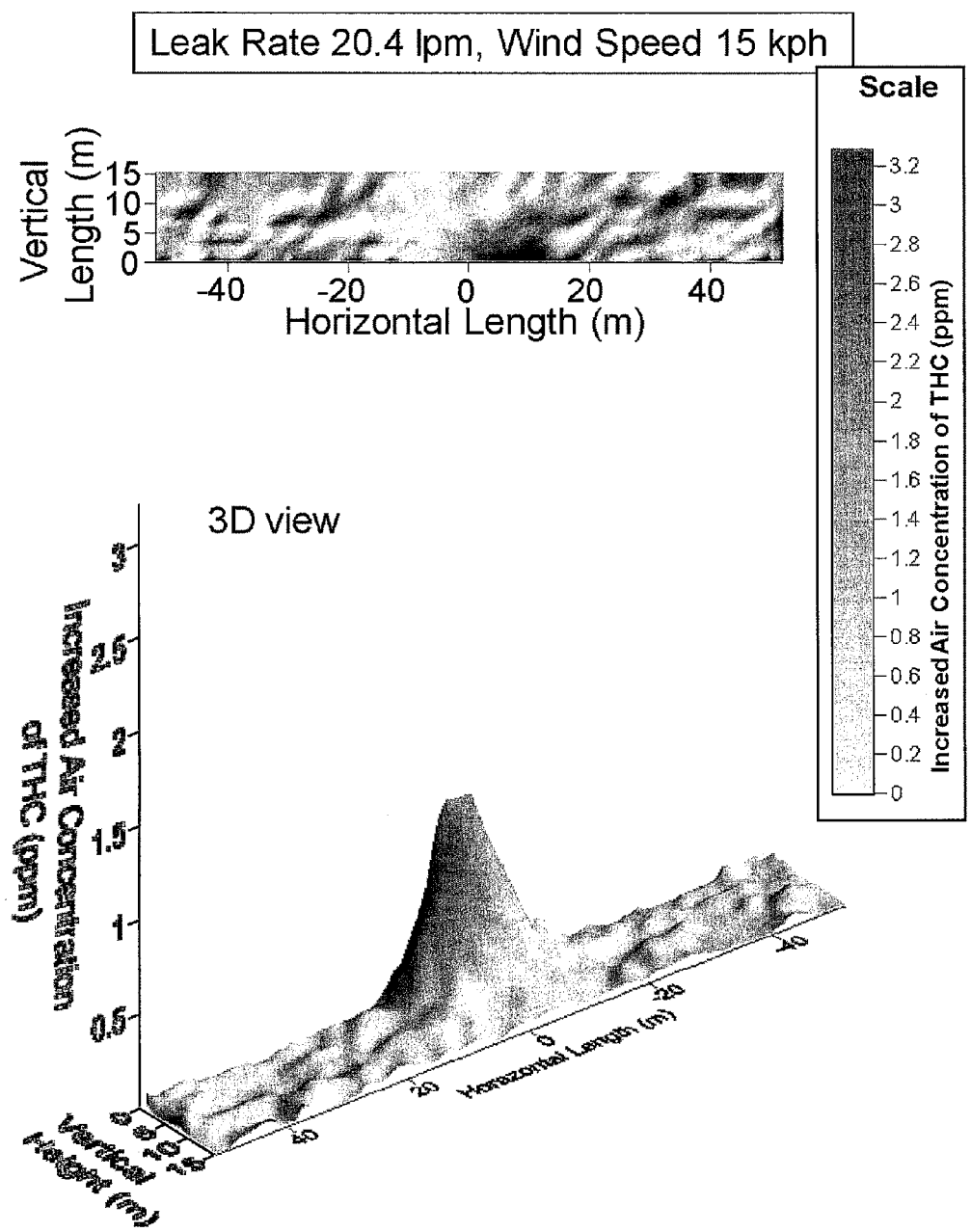
Figure 18E:
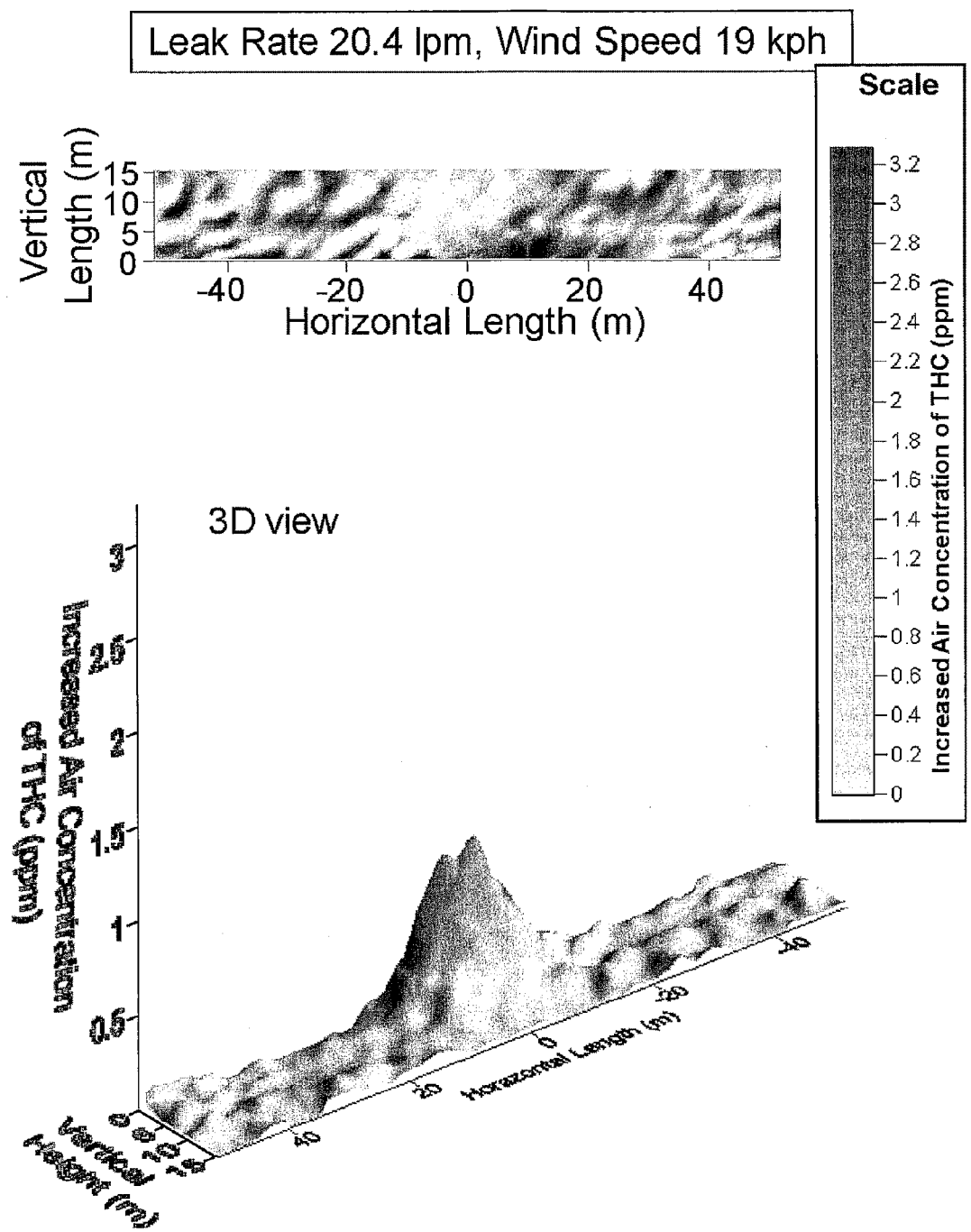
Figure 19A:
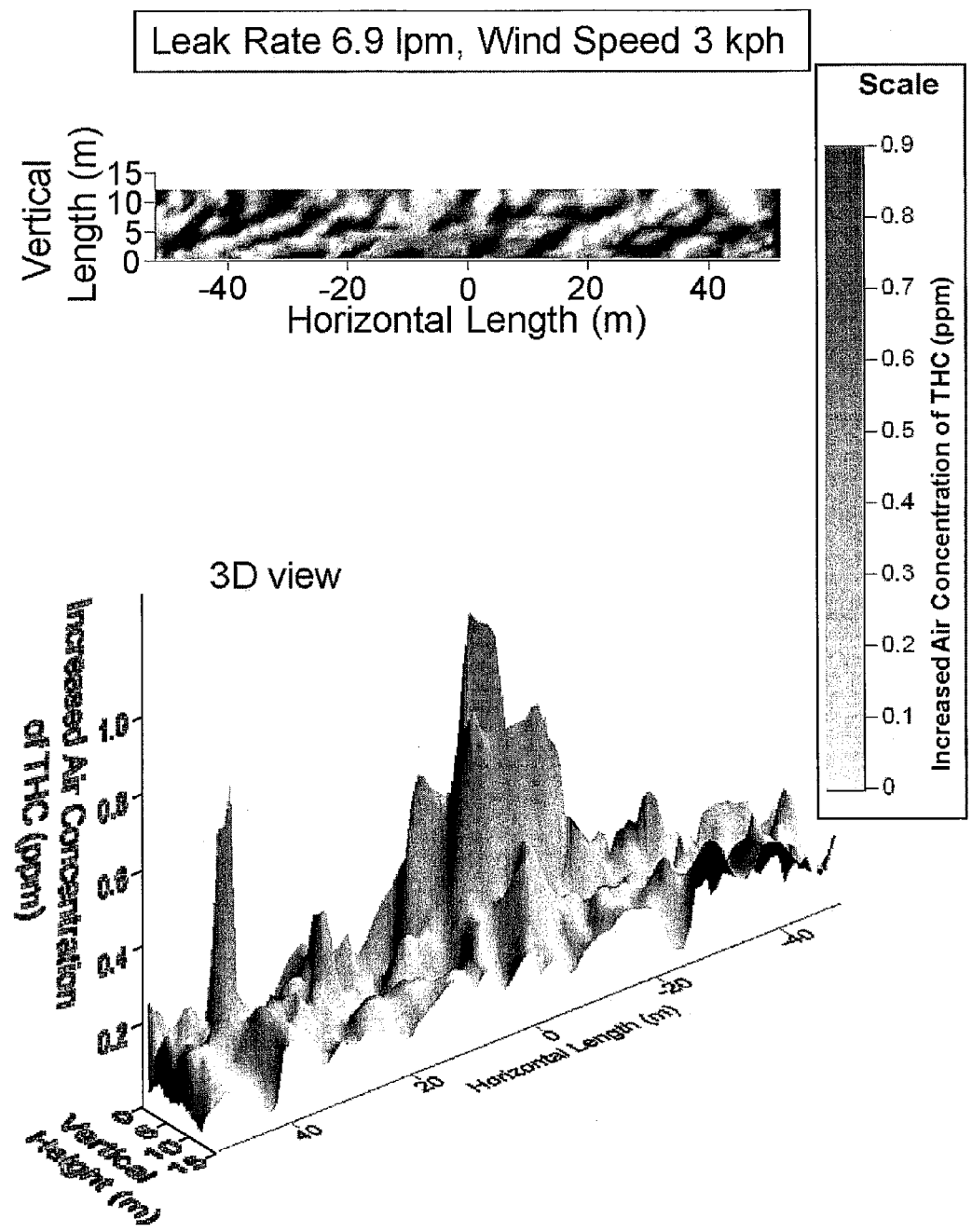
Figure 19B:
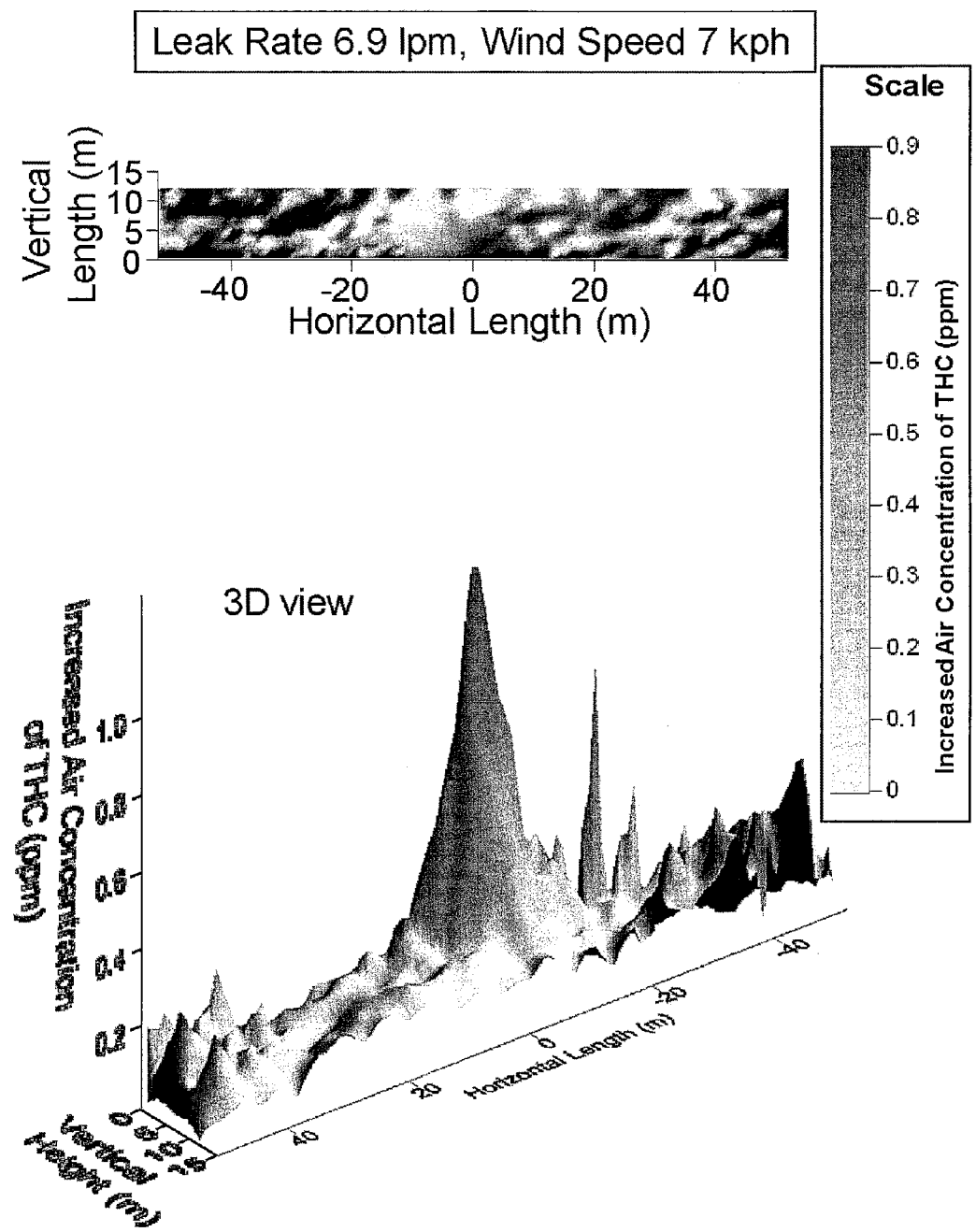
Figure 19C:
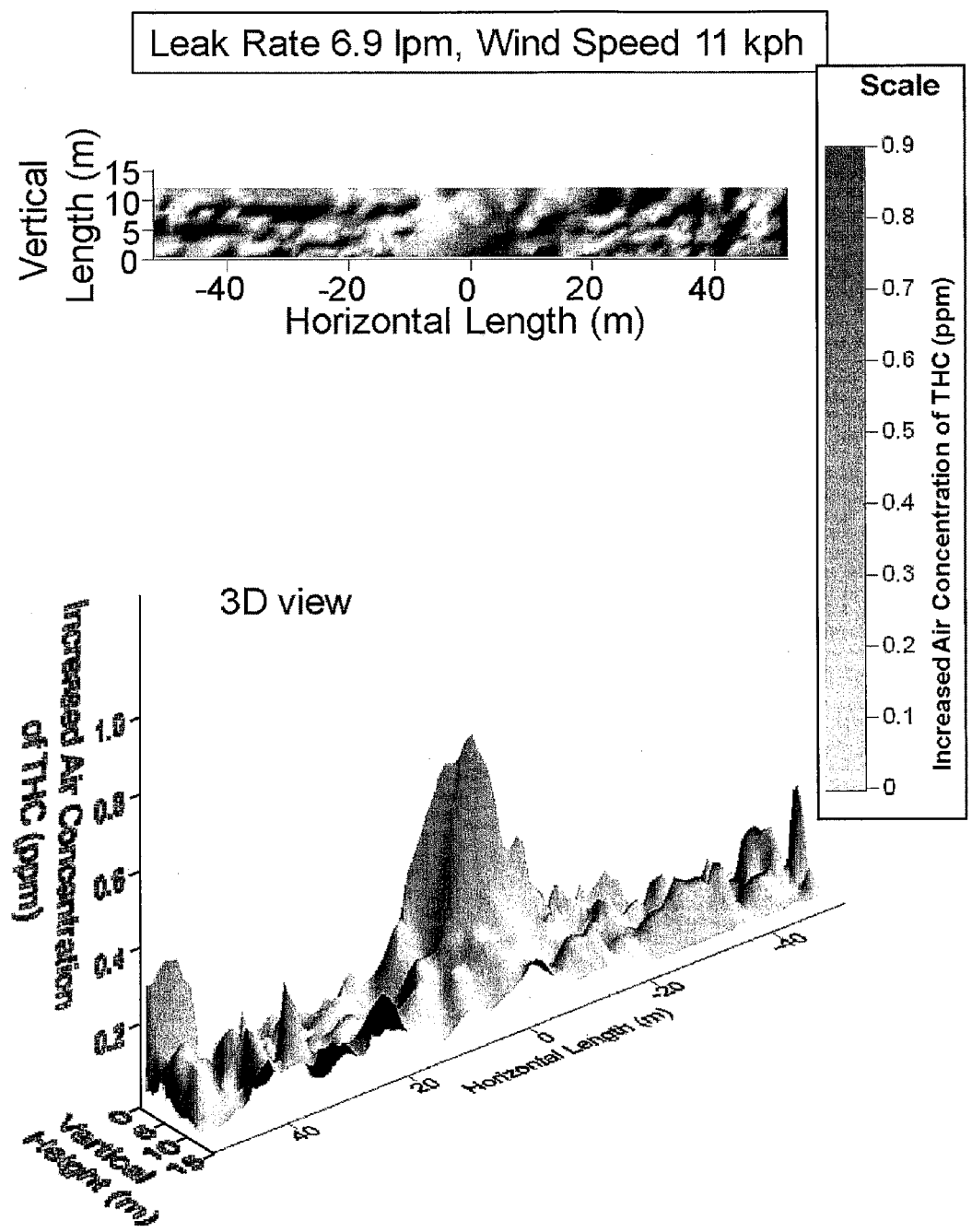
Figure 19D:
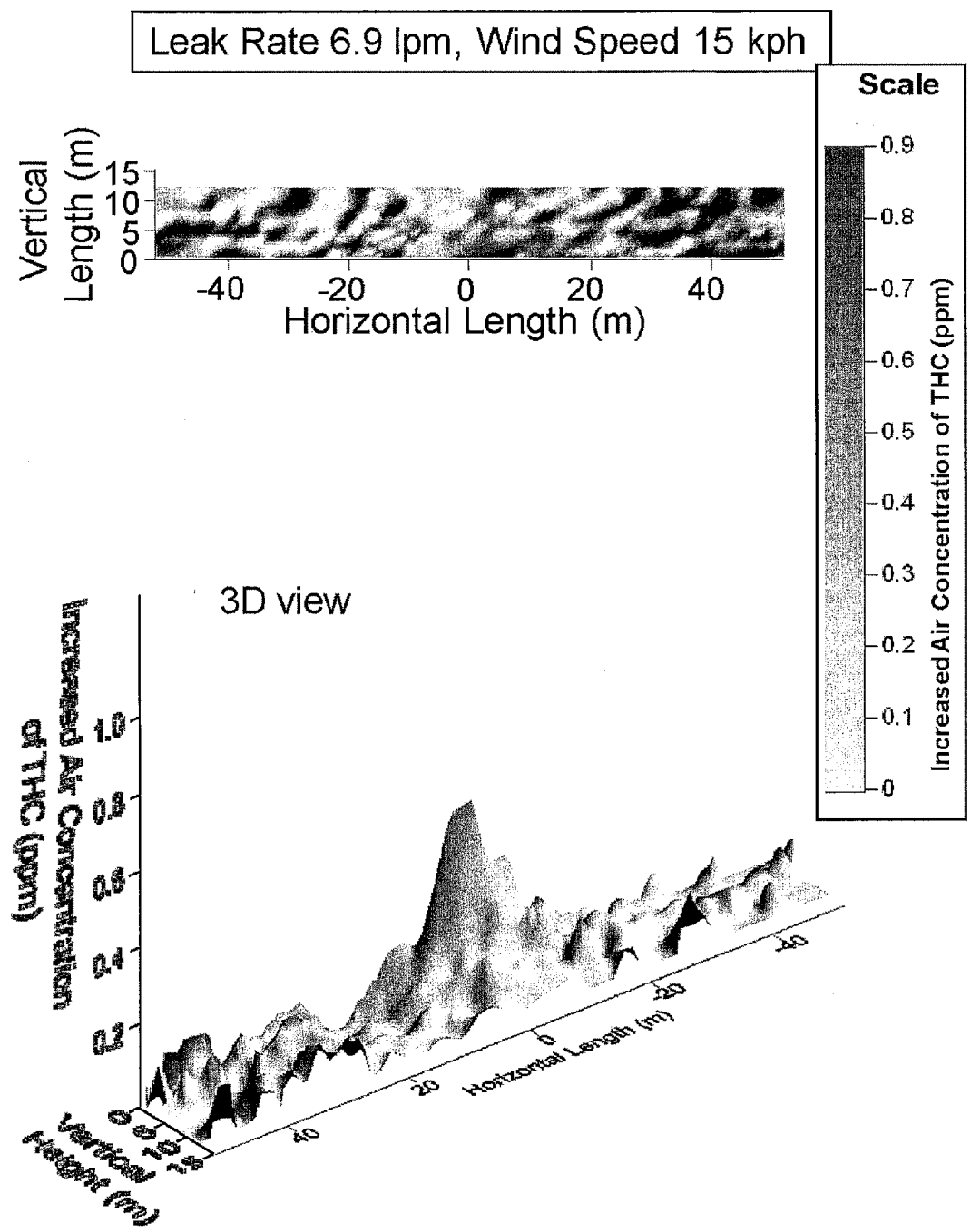
Figure 19E:
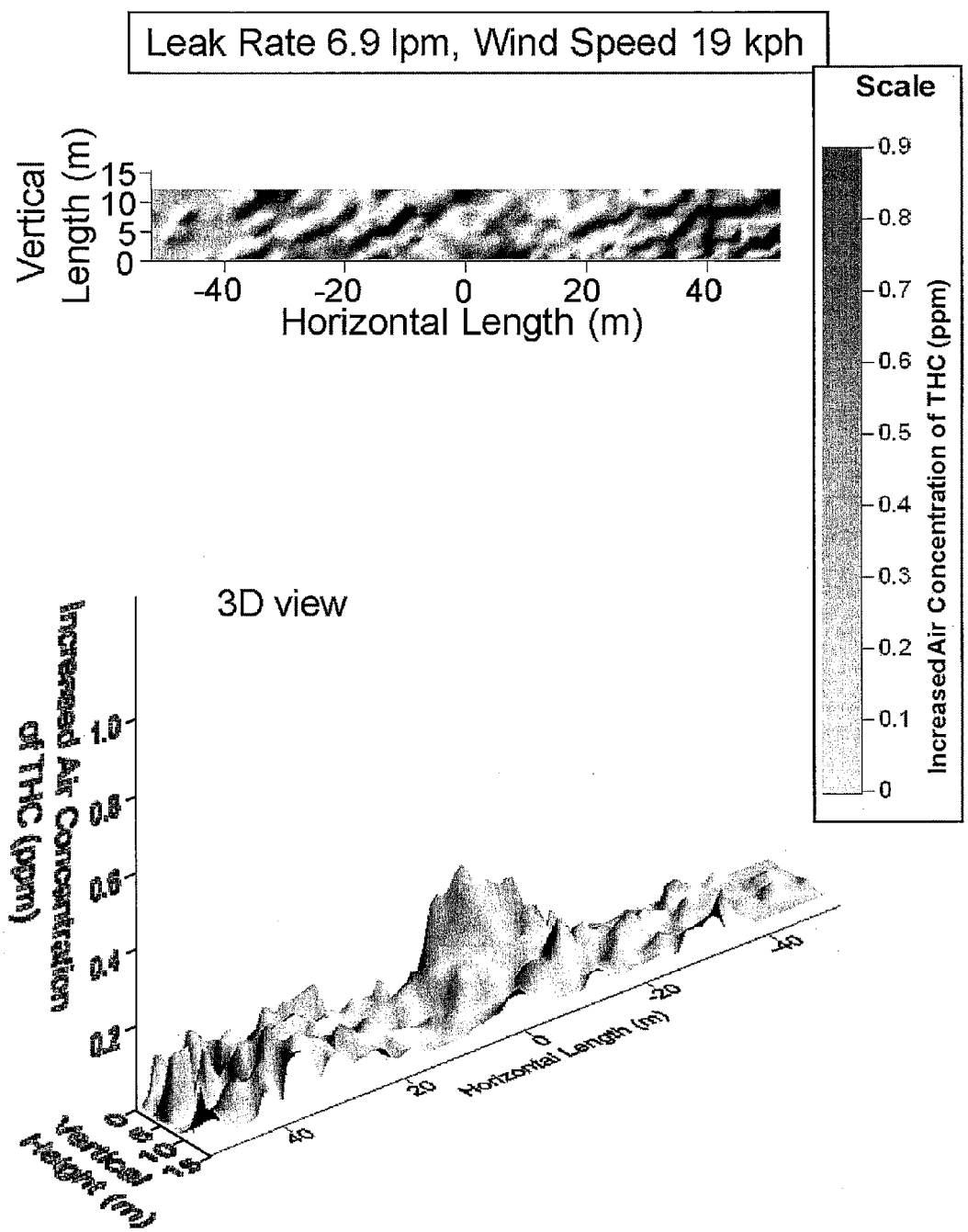
Figure 20A:
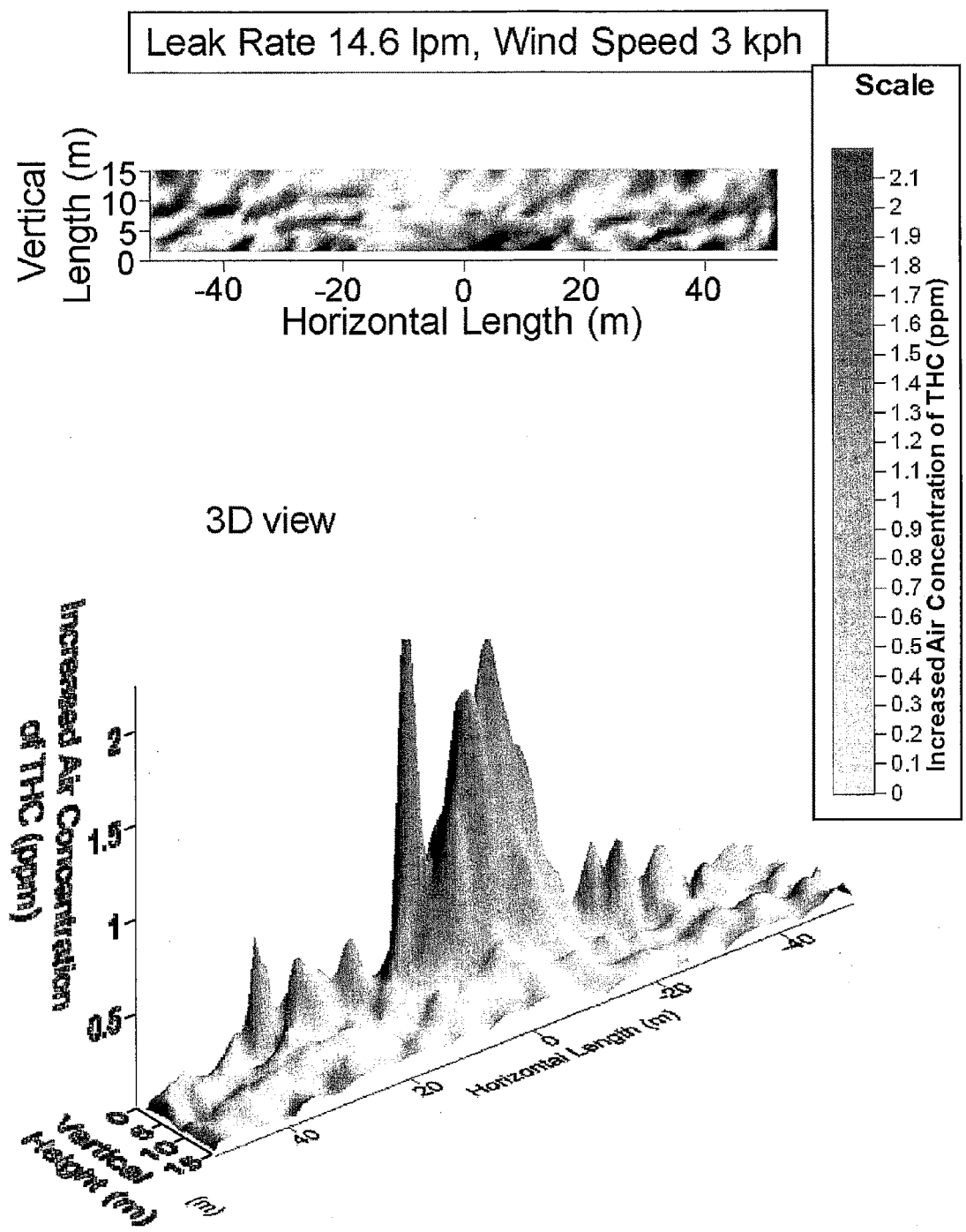
Figure 20B:
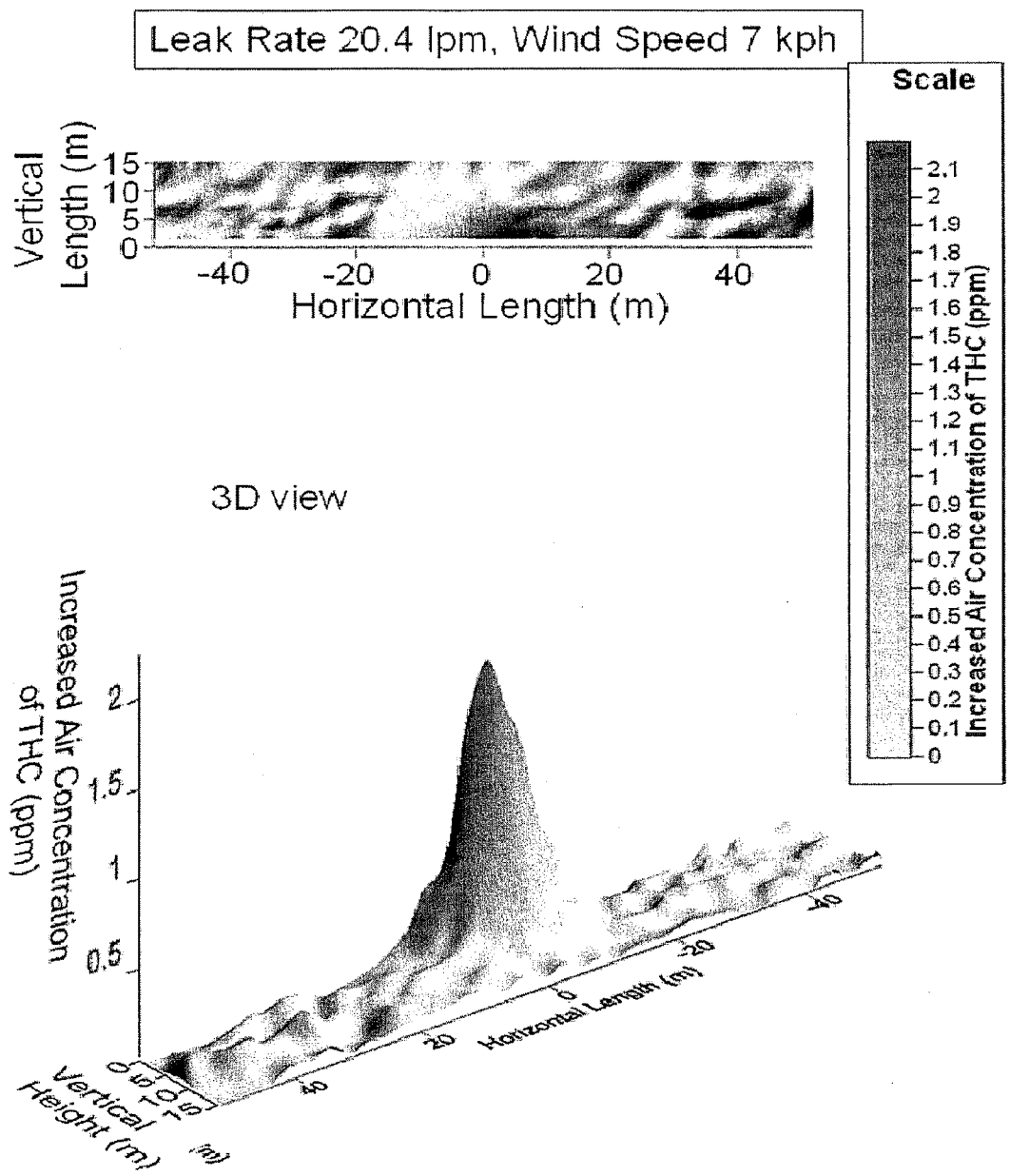
Figure 20C:
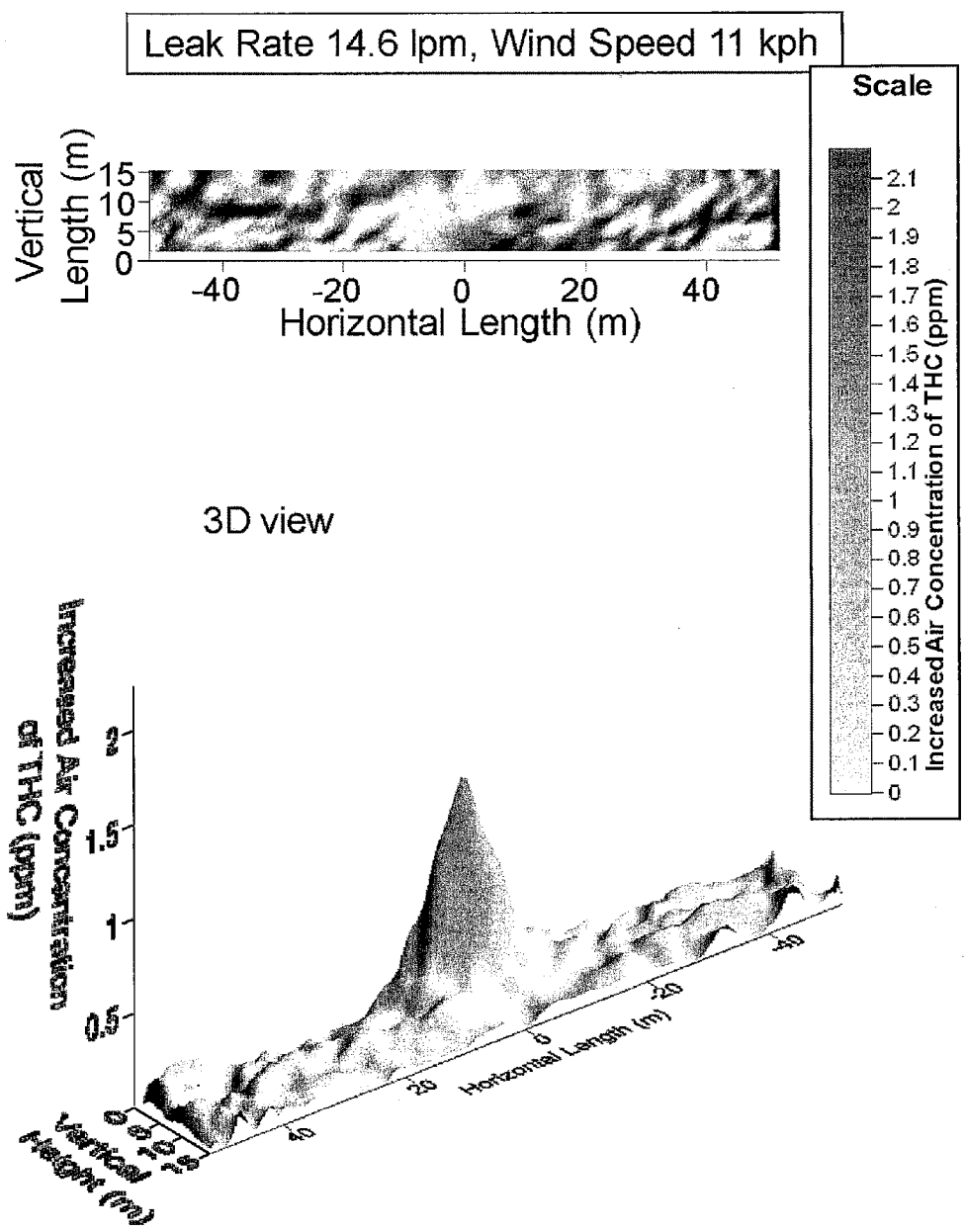
Figure 20D:
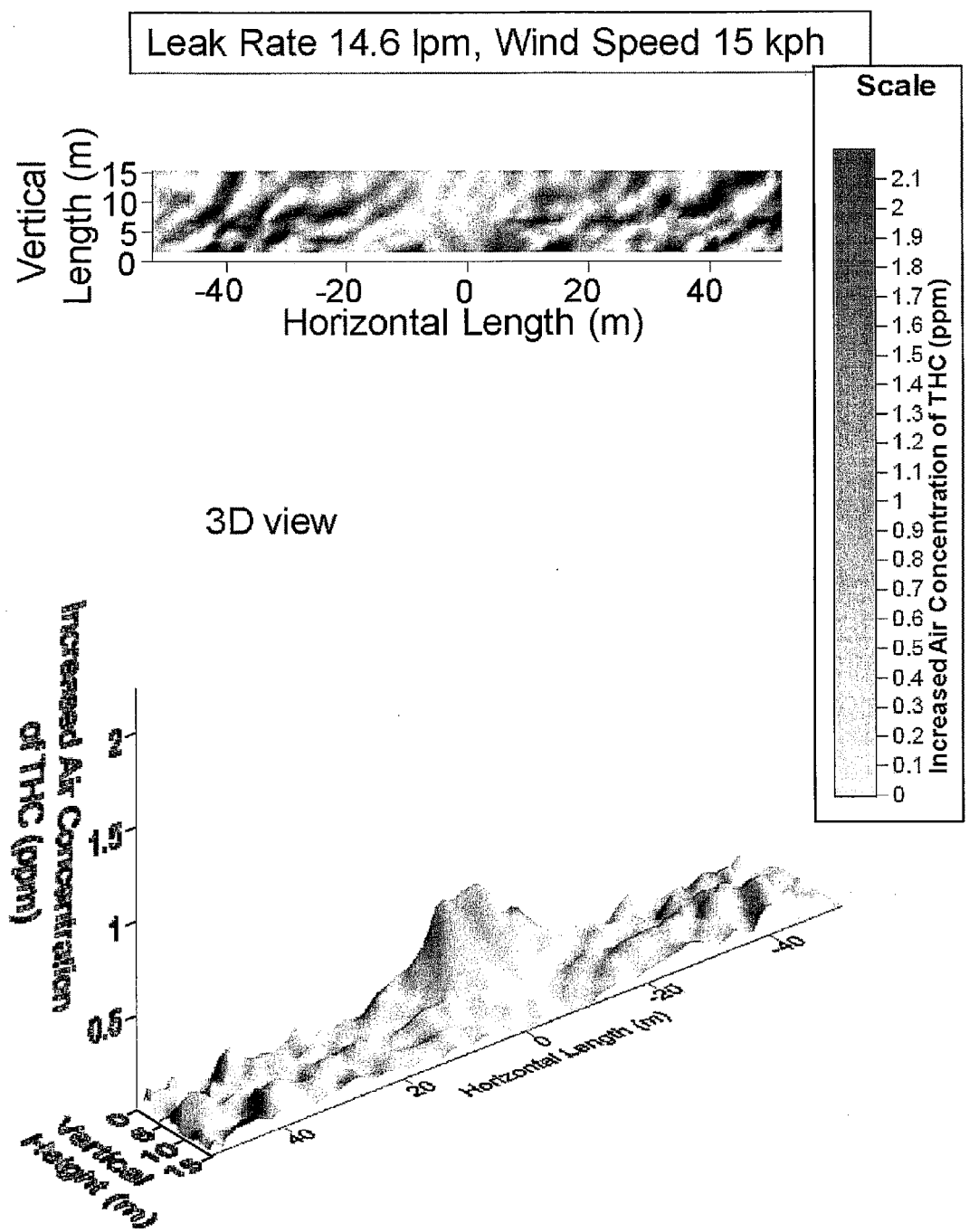
Figure 20E:
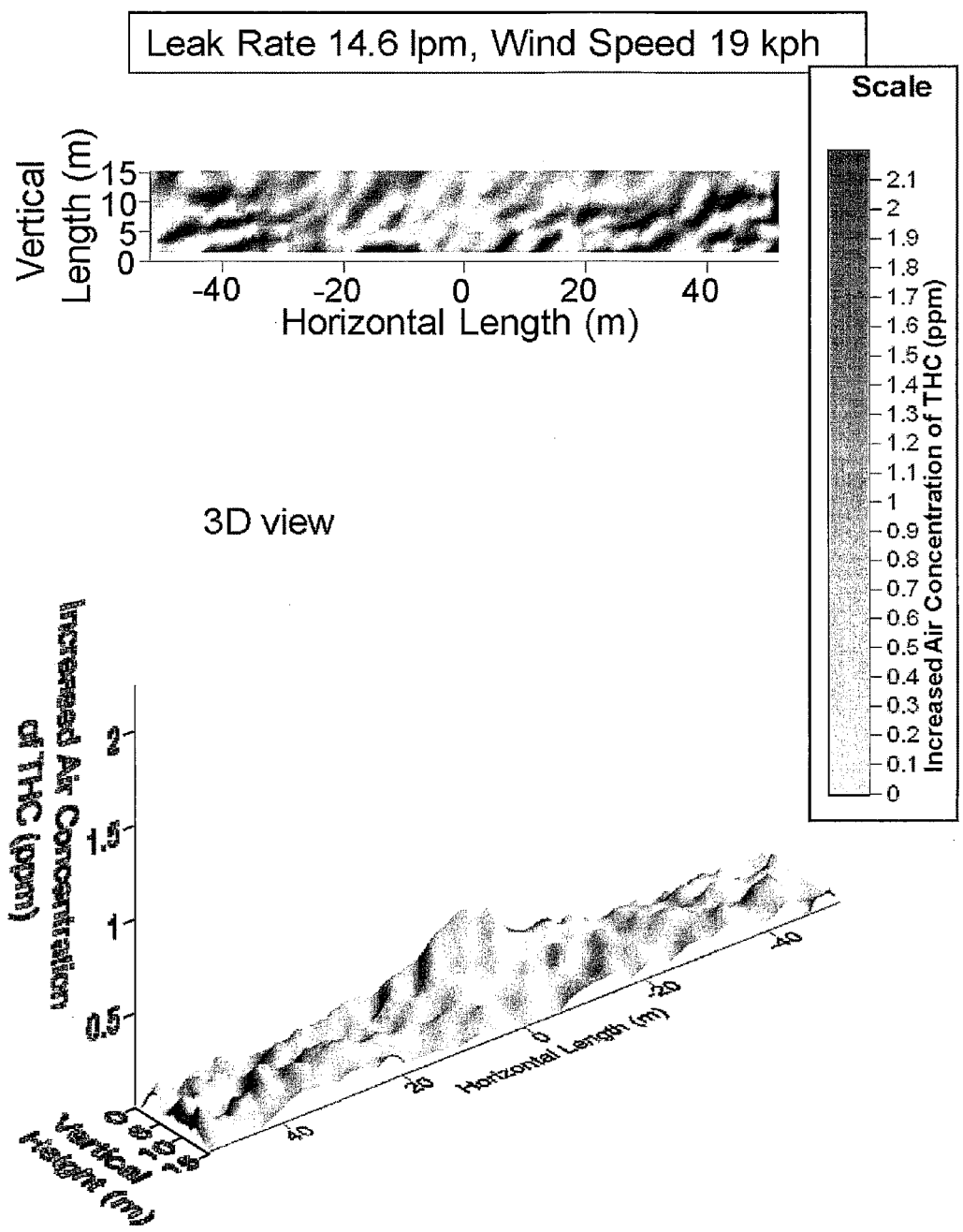

Referring again to FIG. 2, with the data shown in FIGS. 11 through 14 steps 102 and 104 of the method 100 were performed to obtain dimensionless emission plumes for each of the measurement positions. Drawing samples from different elevations results in a different Plume THC concentration profile at different levels. FIG. 15 shows the THC concentrations plotted against wind speed and wind direction at the different heights for the period of November 1 to December 17 when the controlled emission rate was 20.4 lpm. As the figures show, the predominant wind direction during the study was from southwest. The surfaces in FIG. 15 shows the average THC concentration over that period compared to wind speed and direction. FIG. 16 shows the same surfaces without the data points focused in on wind directions from 200 to 300 degrees and wind speeds of 0 to 25 kph. FIGS. 15 and 16 illustrate results obtained after the completion of steps 102 and 104 of the method 100 in FIG. 2. FIGS. 15 and 16 show evidence of the emission plume in a dimension of wind speed and direction at the different heights (i.e. dimensionless). On there own, the plots in FIGS. 15 and 16 do not indicate the physical size of the emission plume in measures of meters but indicate the emission plume characteristics in terms of wind angles and speeds. As expected, the plots show the highest concentrations occur when the wind direction aligns with the emission source 250 and the sampling tower 15 at low wind speeds.

Changes in wind direction results in a shift in the sample points 20 along a arc of a circle centered at the emission source 250 with the radius of the arc equaling the distance between the emission source 250 and the sampling tower 15. The magnitude of the shift is equal the number of degrees of wind change divided by 360 times the circumference (2*PI*r). For a one degree shift in wind direction this would results in a 1.047 m shift in the sample inlet 20 position along the arc of the circle.

Referring again to FIG. 2, step 108 was performed and a set of virtual sampling arcs were constructed using the obtained data. Digitizing the surface in FIG. 16 into one degree increments of wind direction and one kph of wind speed allows the emulation of an array of virtual sample inlets that are 1.047 m apart forming a virtual sampling arc at the height of the sample inlet 20 as discussed earlier (note smoothing was used here by averaging the adjacent readings with equal weight). There is a similar virtual sampling arc for each sample inlet 20 at the different heights.

With the virtual sampling arcs constructed, step 110 was performed and the constructed virtual sampling arcs were combined into virtual sampling grids. Combining the virtual sampling arcs for each of the sample inlets 20 resulted in the creation of a virtual sampling grid of virtual measurement positions emulated by the sampling inlets 20 at the different heights located 60 meters away from the emission source 250 similar to earlier FIG. 7 except the horizontal space will be much closer. The numbers populating the table in FIG. 17 reflect the actual THC measurements taken across this virtual sampling grid less the background level of 1.75 ppm (i.e. these are the THC levels above background levels) over the time period November 1 and December 17 (20.4 lpm emission rate) for the wind speed of 11 kph. Additional tables (not shown) could also be generated for other wind speeds. The numbers in FIG. 17 show the increased THC level resulting from the emission plume. These numbers change at different wind speeds for which another similar table could be calculated.

The emission plume shape and concentration profile were then determined based on the data. The resulting emission plume boundaries and concentration contours are shown graphically for the data in FIG. 18 and the other wind speeds of 3, 7, 15, and 19 kph as well when the emission rate from the emission source 250 was 20.4 lpm. The numbers on the short axis represent the vertical height in meters and the numbers on the long axis represent the horizontal length along the grid of virtual measurement positions (note zero represents the center of the emission plume). It is important to realize that the surface in FIG. 18 is not flat as represented but curves along the arc of the virtual sampling grid. The contour images and 3D surfaces in the figures were generated in mapping software call Surfer™ which converts the values measured on the virtual sampling grid of virtual measurement positions into the images using a kriging interpolation method. Similarly, FIGS. 19 and 20 show emission plume images for the time periods of December 18 to January 17 (6.9 lpm emission rate) and October 10 to 30 (14.8 lpm emission rate).

The emission plumes images in FIGS. 18 to 20 represent the average shape of the emission plume over the sampling period. The uneven levels outside the plume reflect the "background noise" in the method. The higher noise evident at low wind speeds in FIGS. 18 to 20 likely reflects errors at predicting the direction of the bulk flow of air as it moves from the emission source 250 and the sample points 20 based on a single measure of wind direction located at the emission source 250. At higher wind speeds, the time of travel from the emission source 250 to the sample points 20 is less and likely reduces the error of predicting the direction of the direction of the bulk flow of air. Some of the noise in FIGS. 18 to 20 is also due to errors in the THC measurement. In spite of the background noise, the emission plumes are easily distinguishable.

Referring again to FIG. 2, once the emission plume shape and concentration profile was completed at step 112 of the method 100, the emission rate from the emission source 250 was quantified using step 114. Referring to FIG. 8, the method 200 was performed to approximate emission rates for the emission source 250. The quantification of the emission rate was accomplished by calculating the flux of increased THC compounds crossing the virtual sampling grid after dividing the virtual sampling grid into subsections.

Step 210 of the method was performed and the obtained virtual sampling grid is divided into subsections. The vertical spacing of the subsections is set by the vertical spacing of the sample inlets 20 on the tower 12. The horizontal spacing of the subsections can be set by the size of increments of wind direction on which the data is aggregated. The increments can be small enough to accurately characterize the emission plume (1 degrees was used in the test). In FIG. 17 one degree was used to aggregate the data which is associated with 1.047 m separation along the virtual sampling arc. The boarders of each subsection are defined by half the distance to the adjacent subsection center. If there is no adjacent subsection as along the bottom of the virtual sampling grid then the border is the ground (or something just above to reflect there is little air flow along the ground). The top boundary of the subsections along the top of the virtual sampling grid is assumed as the same distance to the center of the subsection as the bottom boundary (this upper boundary can also be assume base on an extrapolated emission plume concentration profile if the emission plume boundary extends above the virtual radial sampling grid). The area of the subsections are calculated by height*width if the elements are rectangular. FIG. 17 shows the virtual sampling grid with the heights and widths the subsections for a one degree wind direction aggregation.

With the virtual sampling grid separated into subsections, step 220 of the method 200 shown in FIG. 8 was performed and a flux value across each subsection was determined. The flux values were obtained by multiplying the increased THC concentration (i.e. the THC concentration less the background level of 1.75 ppm) by the wind speed.

Figure 21:
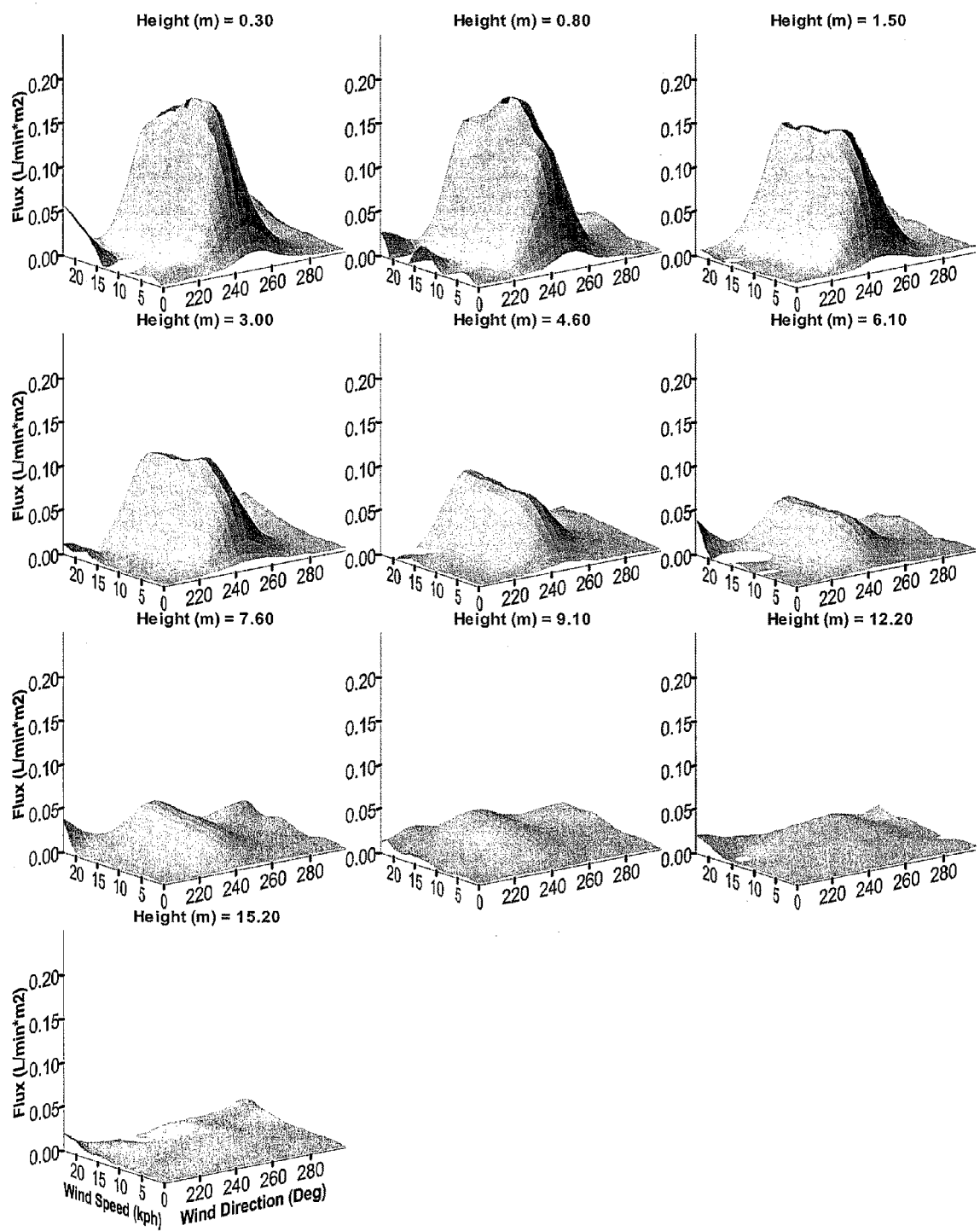
FIG. 21 is a set of plots representing the average flux of the emission in relation to wind speed and direction at different sample inlets.
Figure 22A:
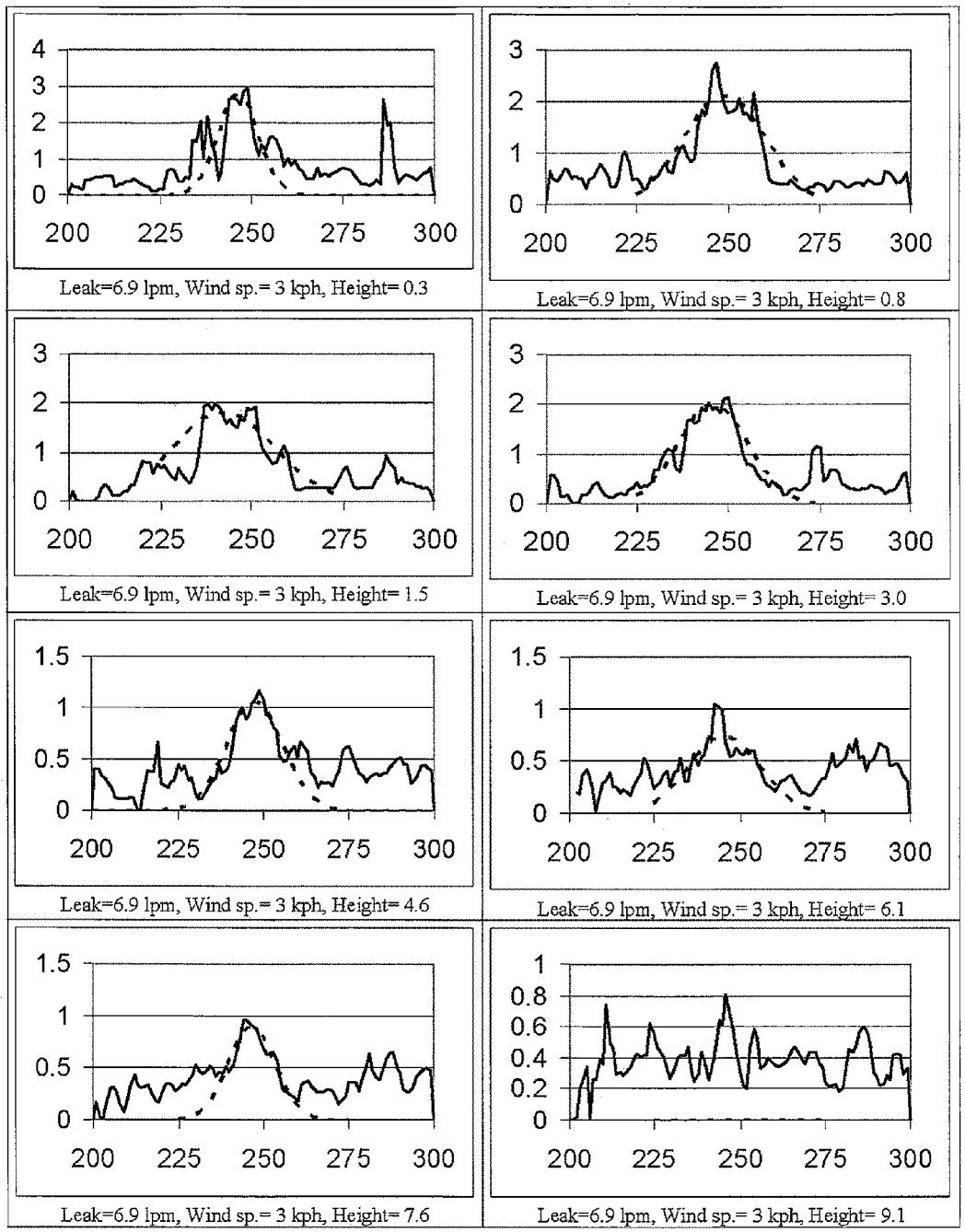
FIGS. 22, 23 and 24 are sets of plots representing plume flux distributions at different wind speeds and observation heights for different emission rates.
Figure 22B:
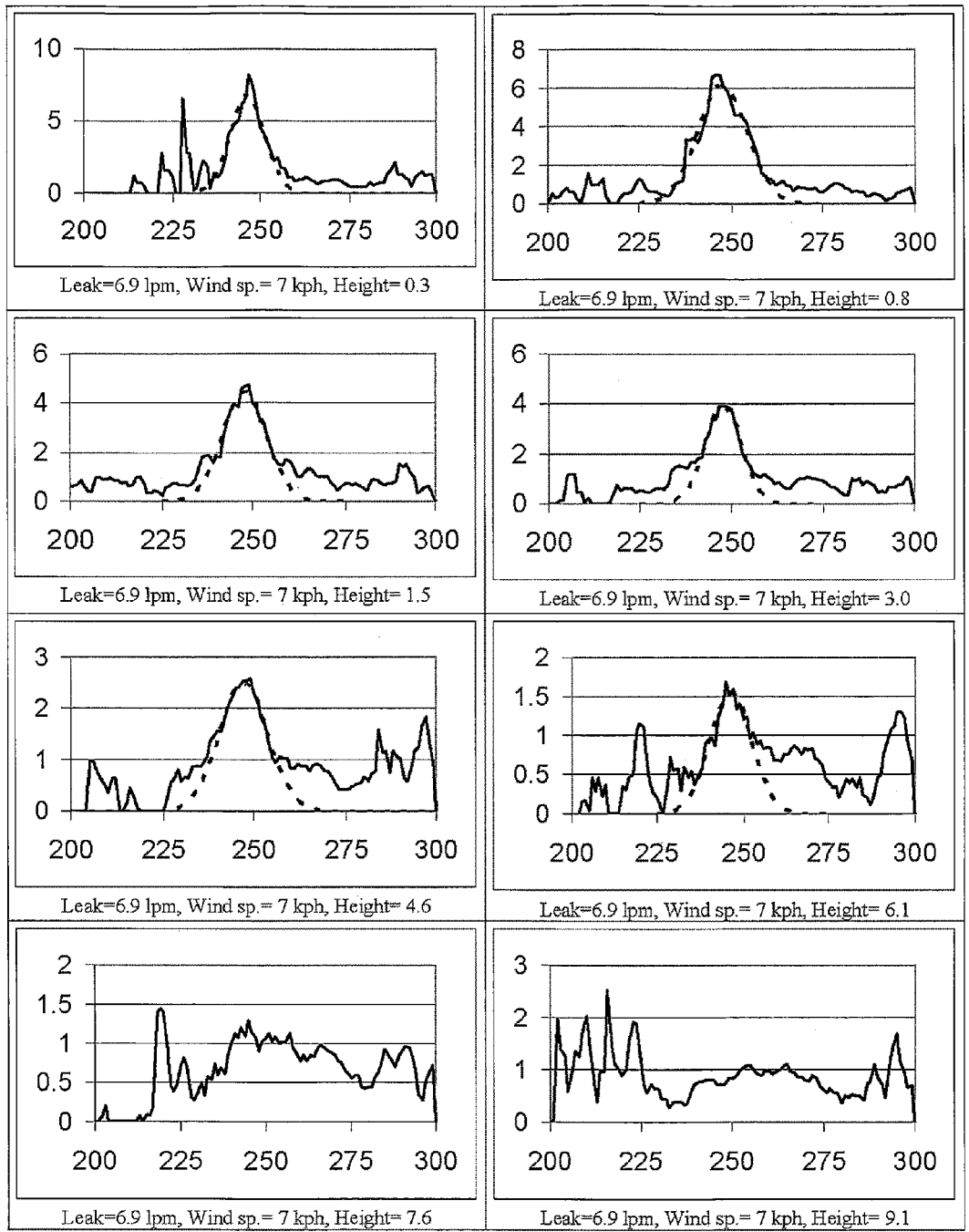
Figure 22C:
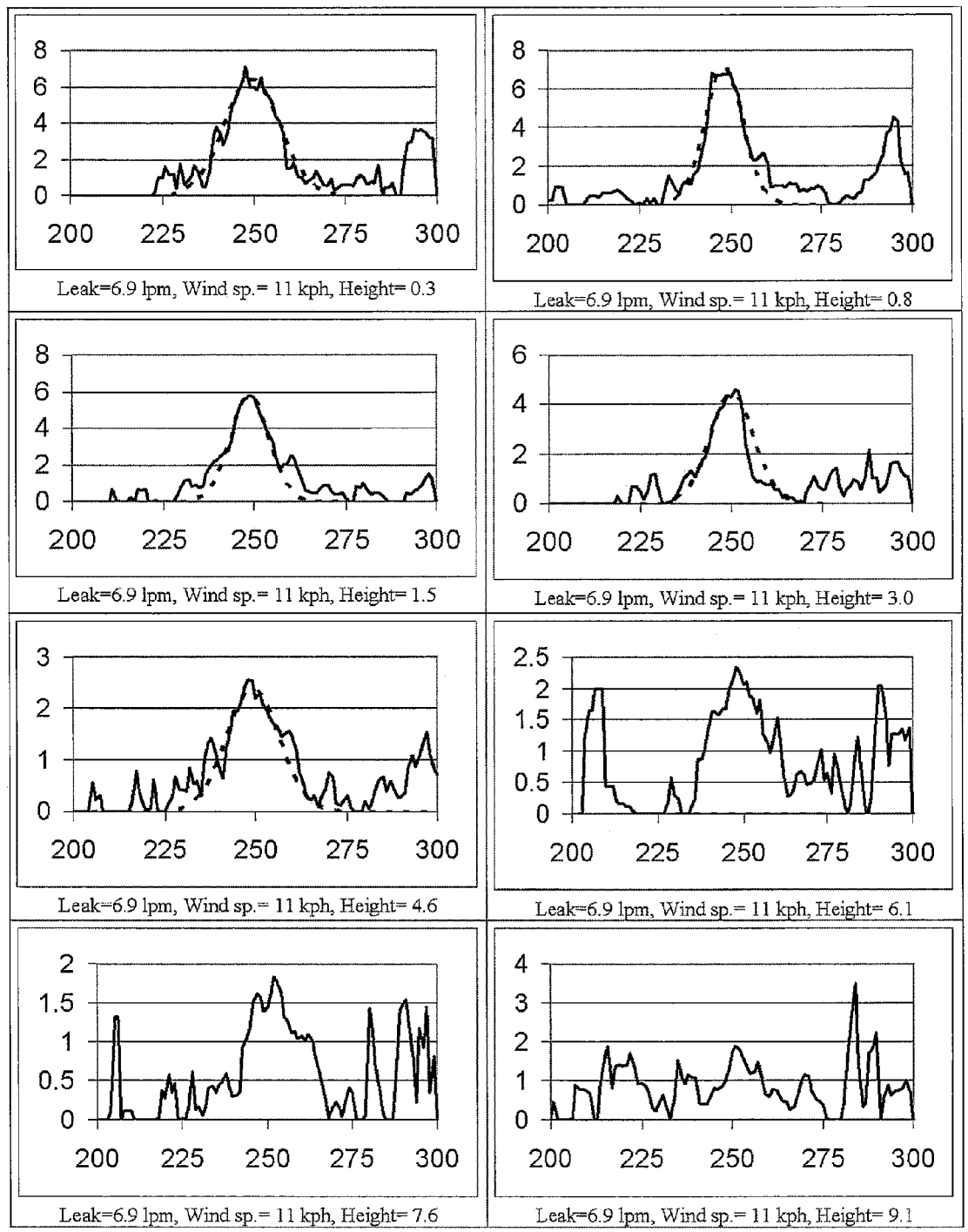
Figure 22D:
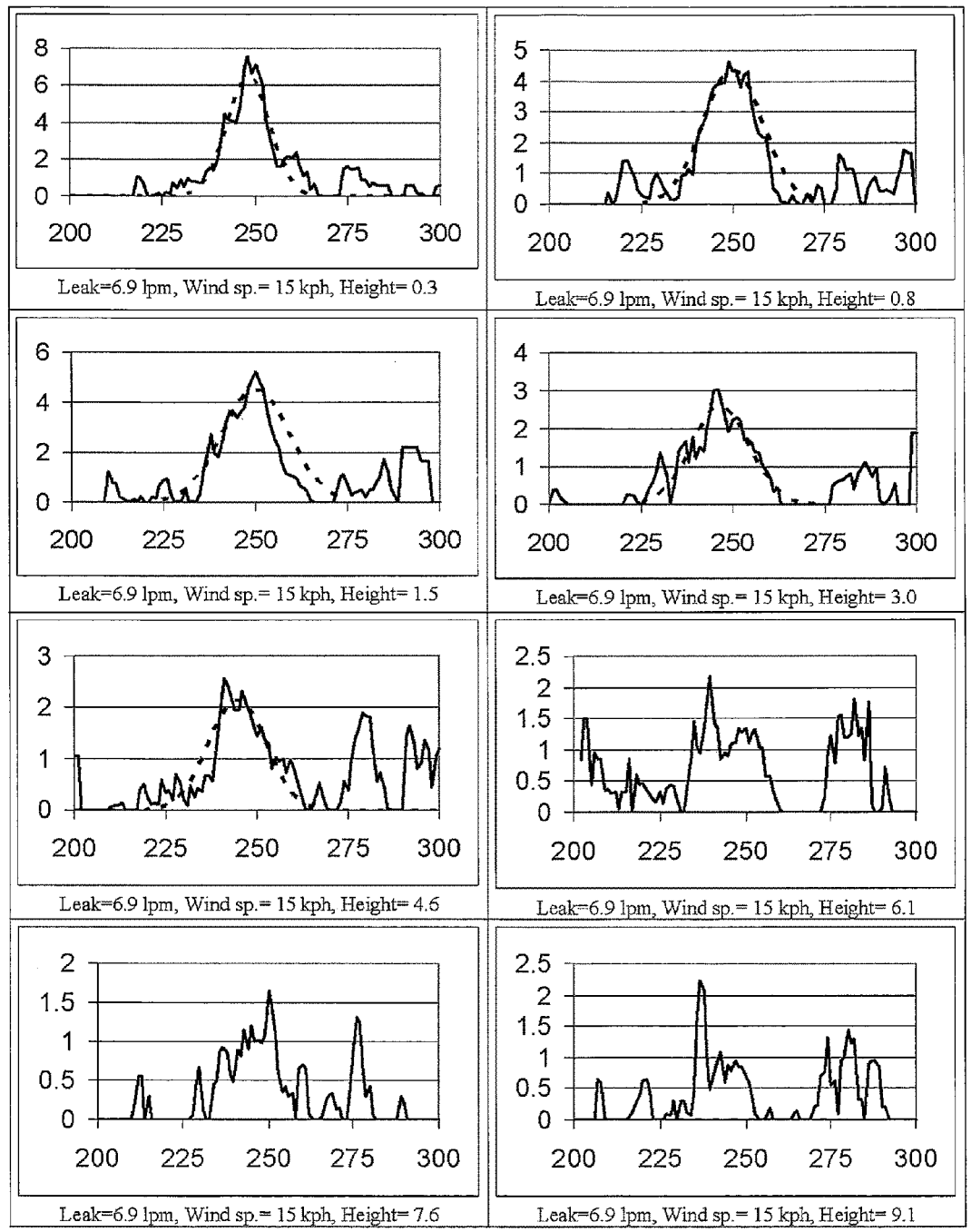
Figure 22E:
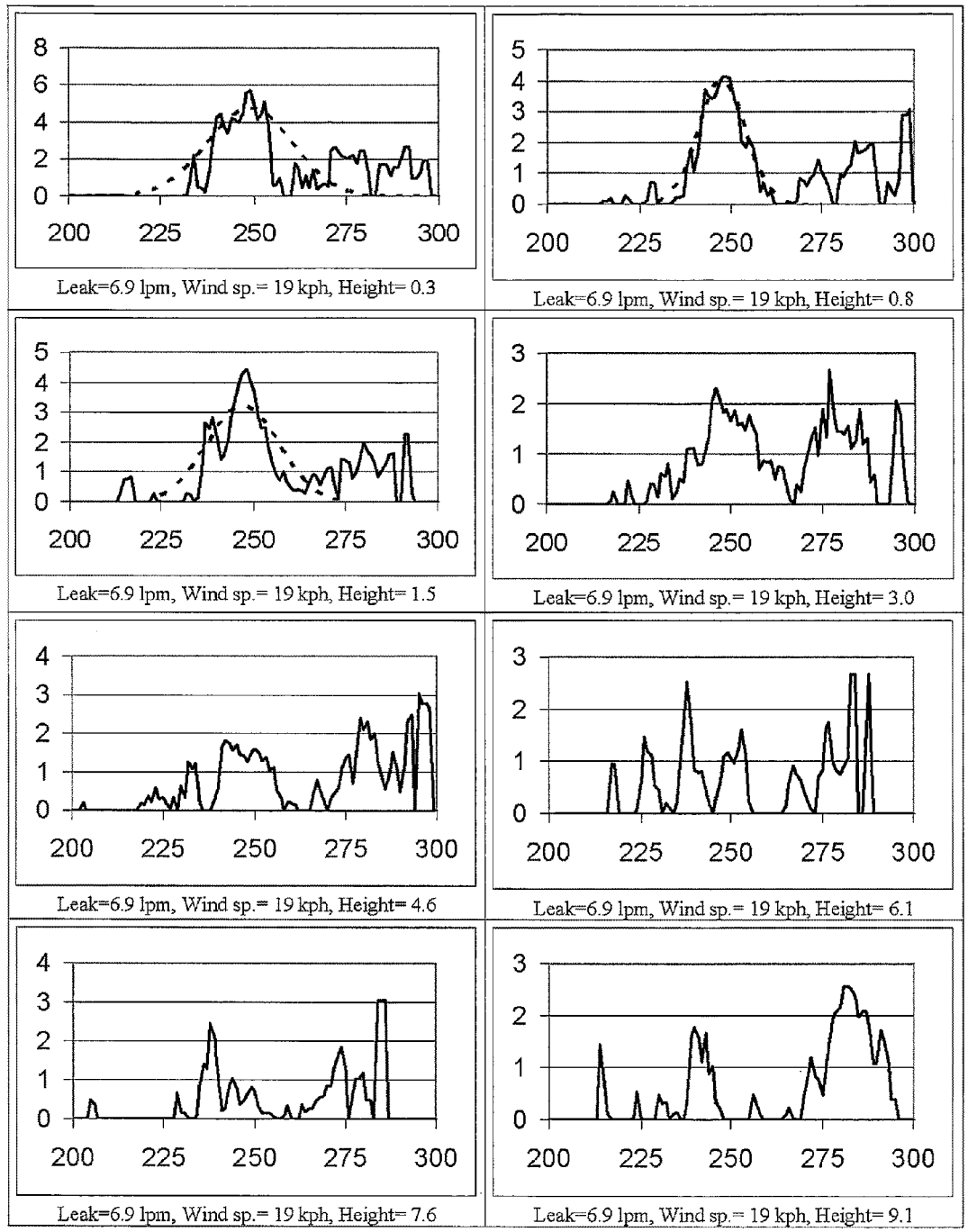
Figure 23A:
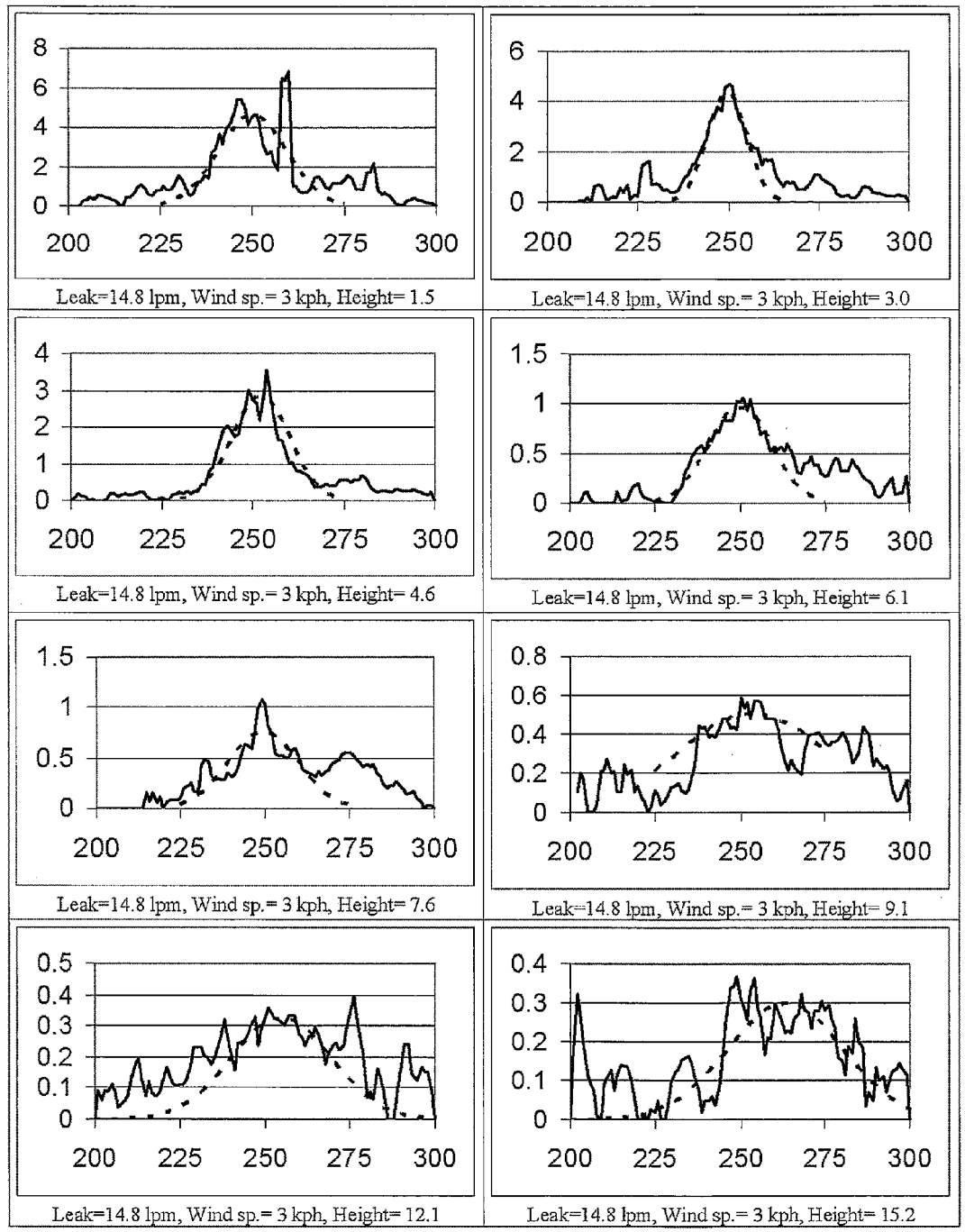
Figure 23B:
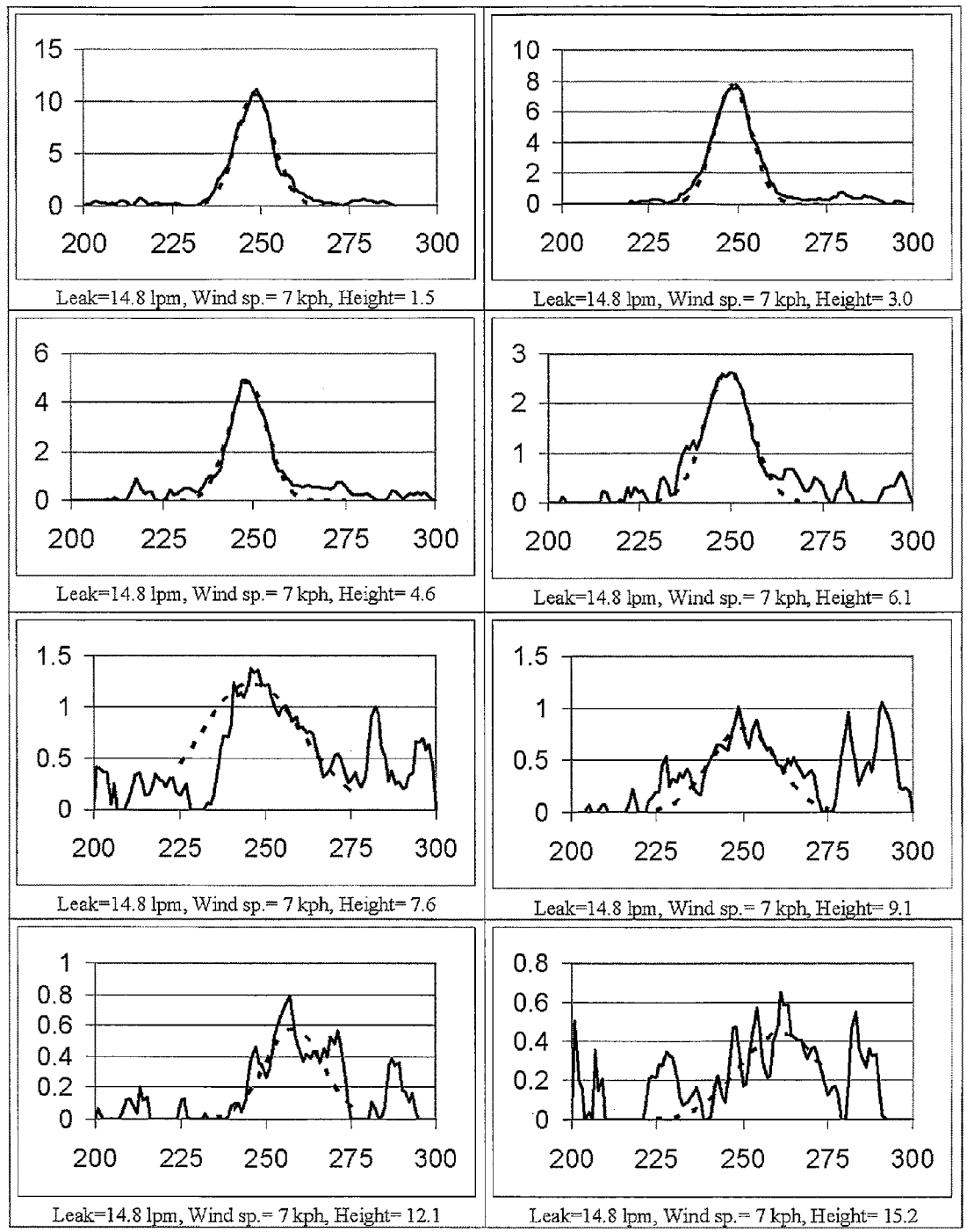
Figure 23C:
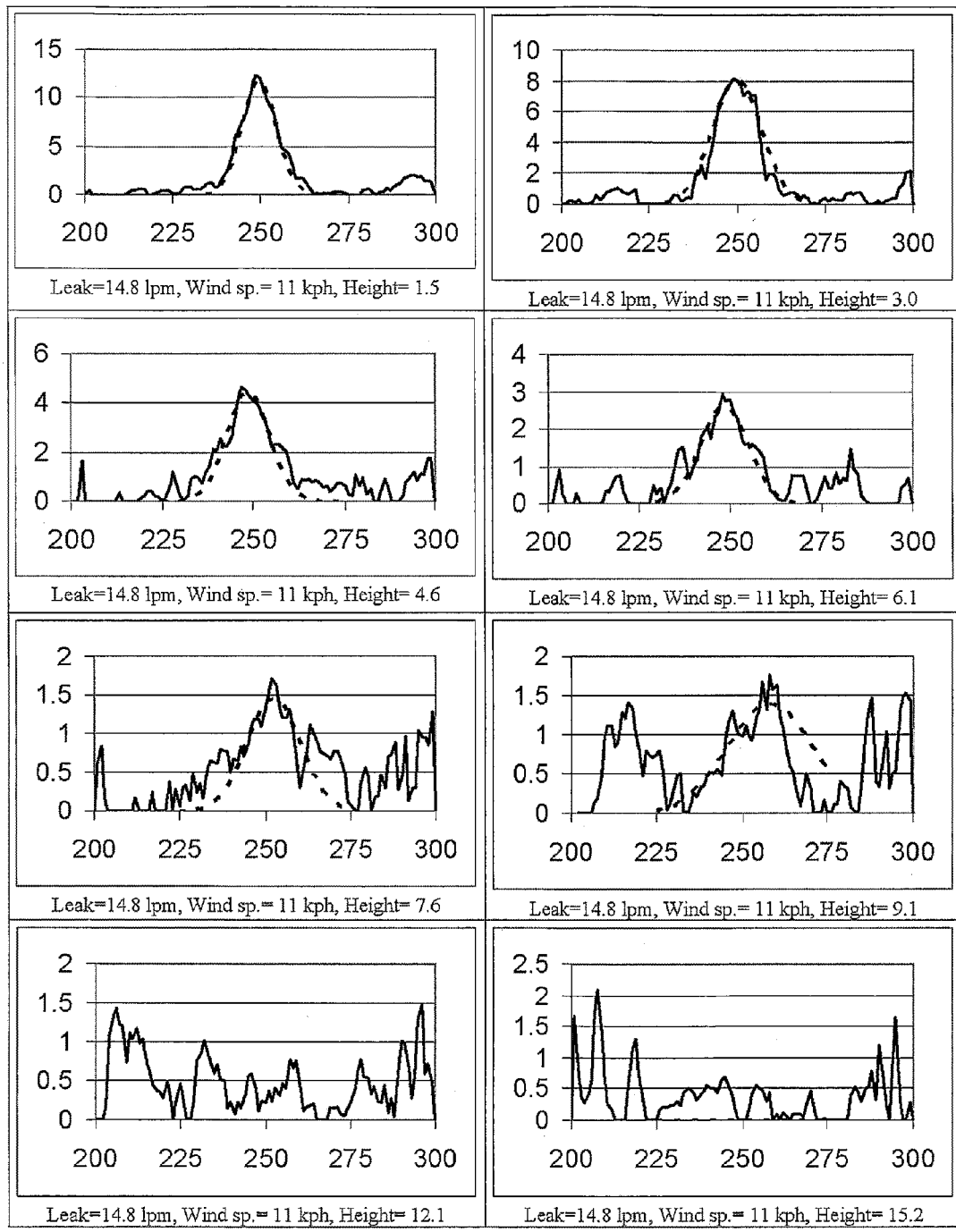
Figure 23D:
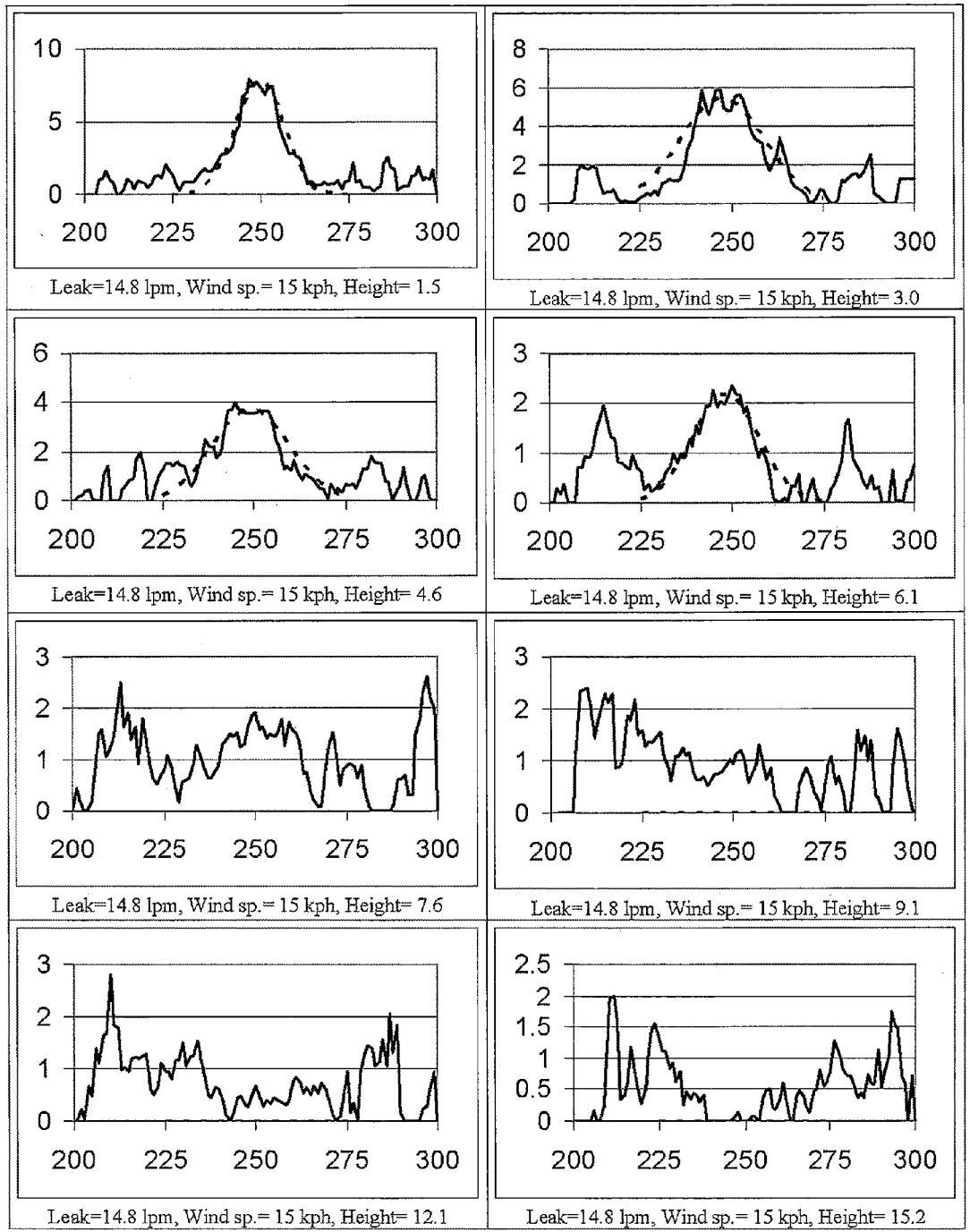
Figure 23E:
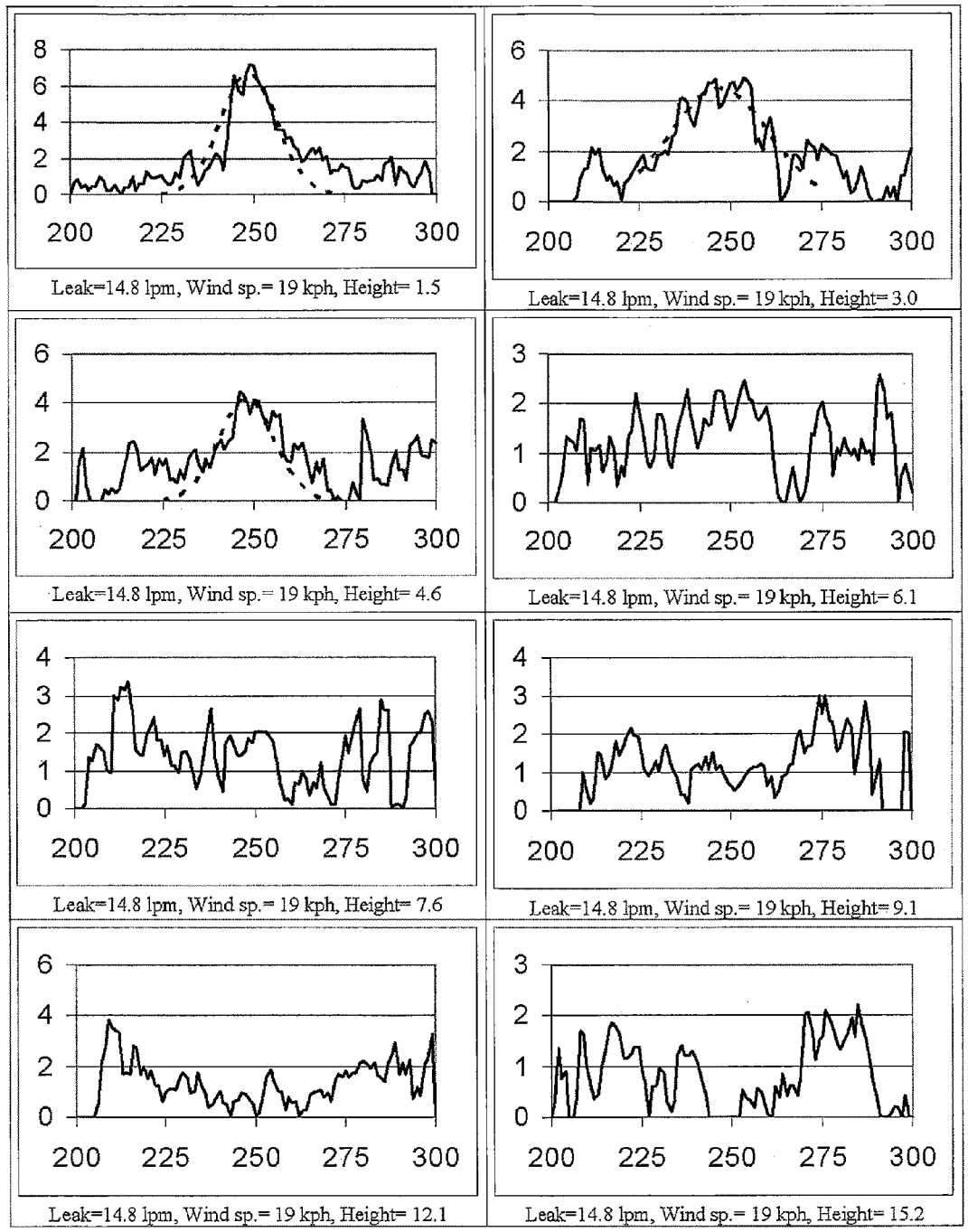
Figure 24A:
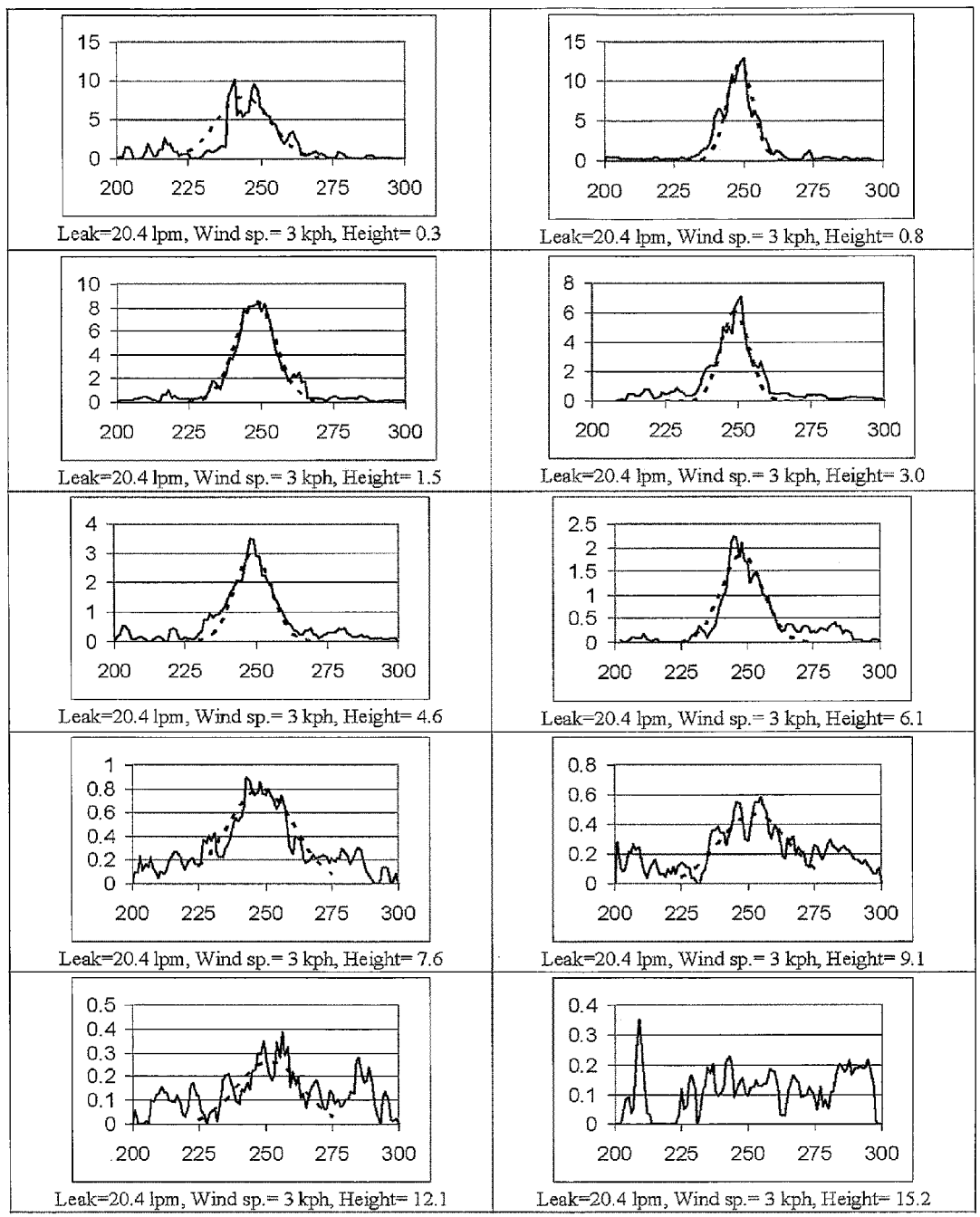
Figure 24B:
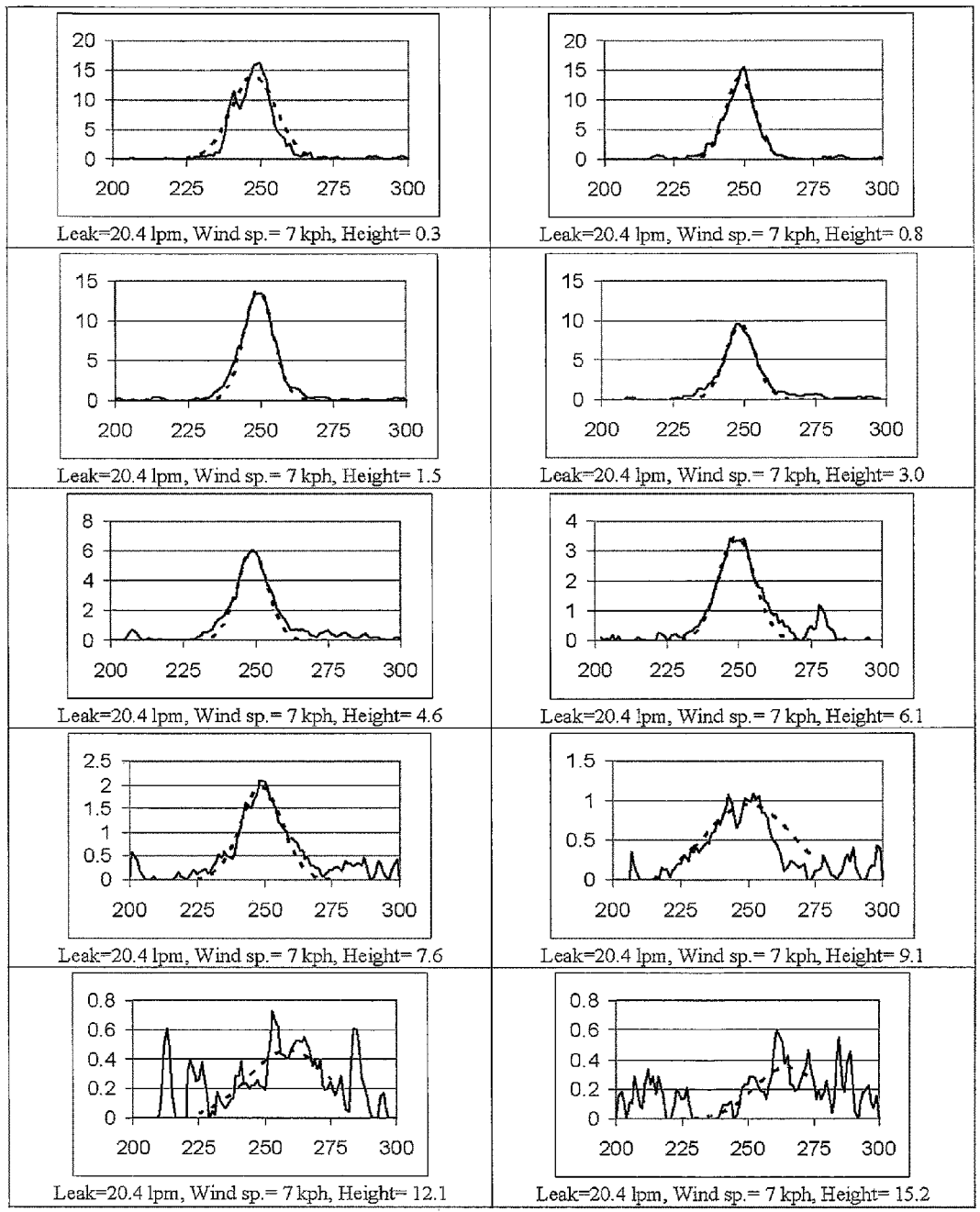
Figure 24C:
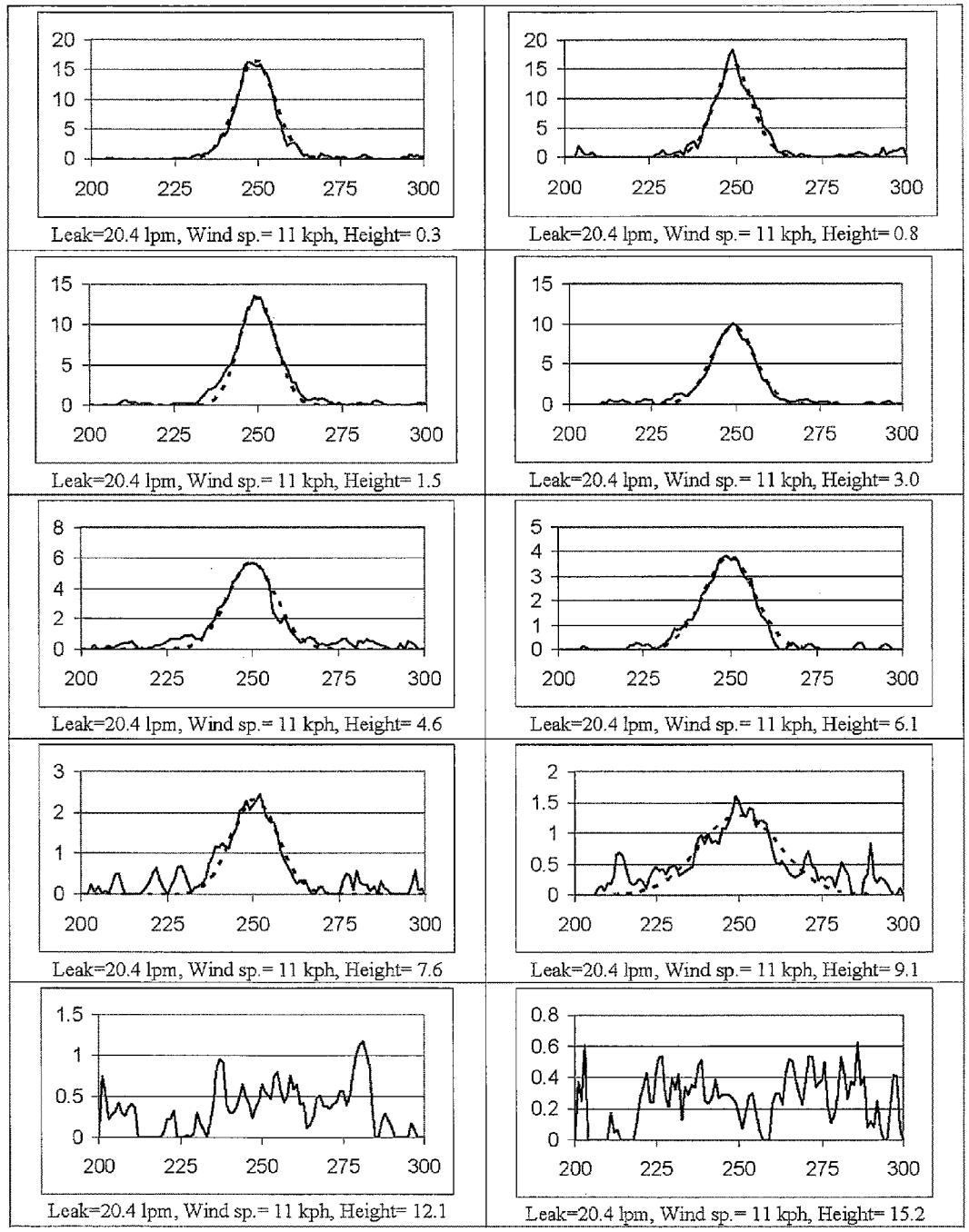
Figure 24D:
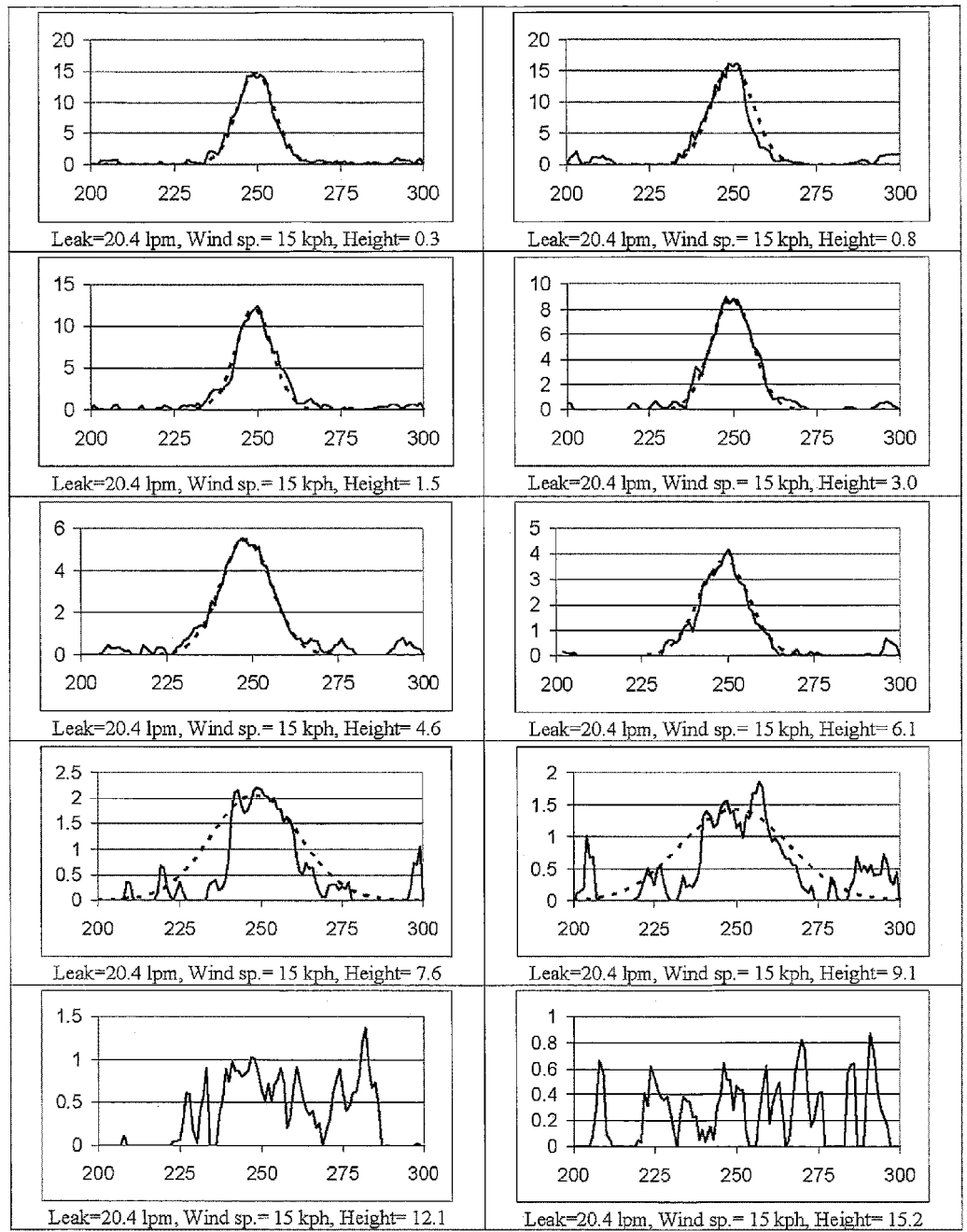
Figure 24E:
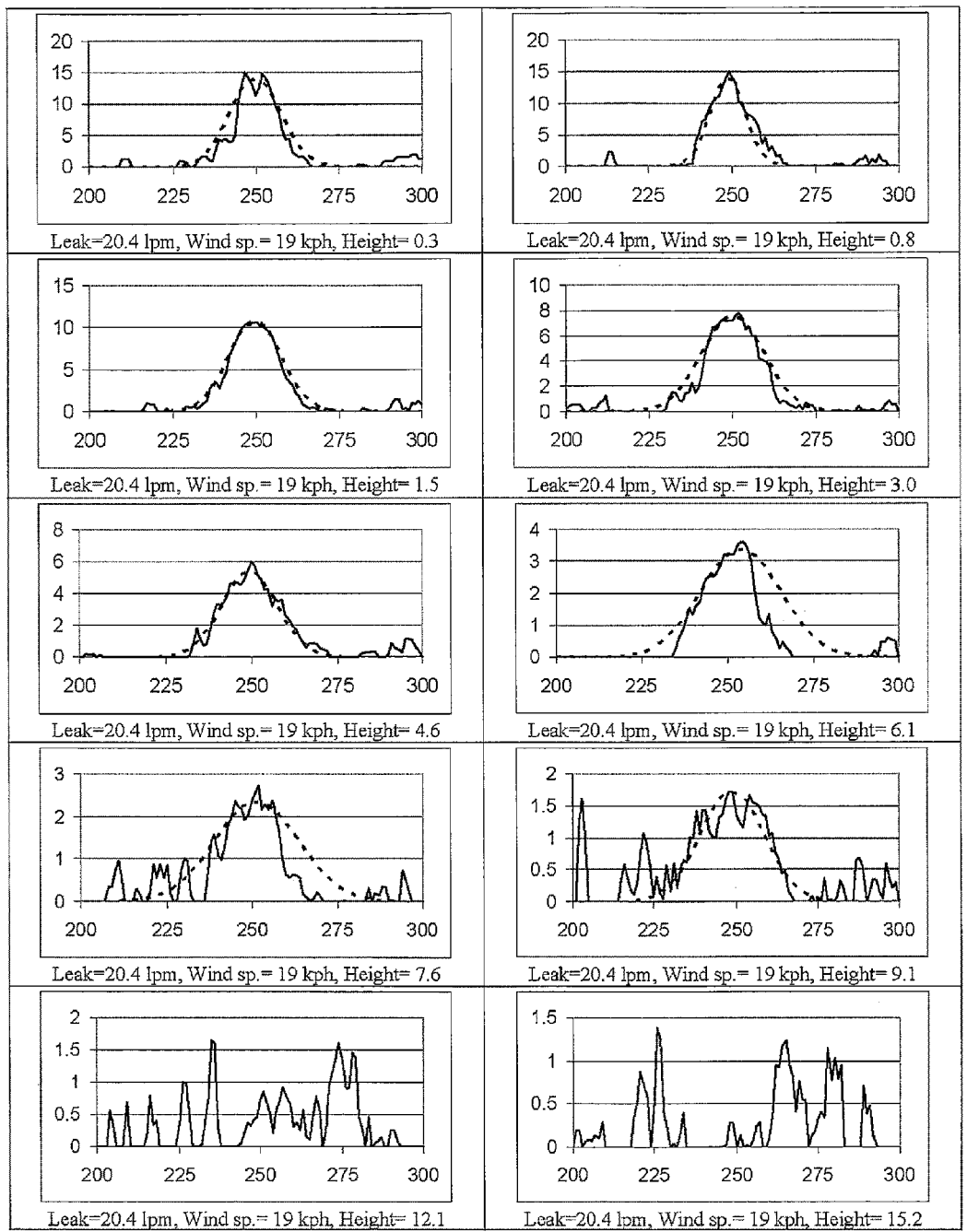

The THC concentrations shown in FIG. 16 were converted to flux values and plotted with wind speed and direction in FIG. 21. The plots show the THC flux of the emission plume for different wind speeds and directions in a time period where there was a single controlled emission rate.

Referring again to FIG. 8, step 230 was performed and the subsections that were within the emission plume boundary were determined for the different wind speeds. The increased THC concentration flux plots like those in FIG. 21 were isolated for some individual wind speeds and plotted against wind direction for the three different controlled emission rates in FIGS. 22 to 24. The modeled emission plume shape in the dashed line is a Gaussian distribution fitted to the upper portion of the emission plume shape by a linear regression of a natural log transformation of the flux values. The boundary of the emission plume was taken to be the point where the modeled flux breaks below some minimum flux level (we are using 0.0067 L/(hr*m2)) on either side of the emission plume peak. This allows the emission plume boundaries that exist within the background noise to be approximated. A model is not fitted and the emission plume is considered not definable when the emission plume shape is not dominant above the background flux values.

Referring again to FIG. 8, step 240 was performed to determine the flowrate of the emission being measured through each of the subsections. The compound flow rate through each subsection was determined by multiplying the rate of flux of increased THC determined for an area by the area of the subsection. Step 245 was then performed and the flow rates throughout the emission plume were totaled to approximate an emission rate of the emission source 250 shown in FIGS. 9 and 10.

Using method 100 shown in FIG. 2 and method 200 shown in FIG. 8, emission flow rates were calculated for the three different emission conditions and the for wind speeds from 1 to 19 kph. The results are presented in FIG. 25 which shows the estimated emission rate versus wind speed for the three controlled emission rates during the study. There are three lines in the plots in FIG. 25 that show the expected controlled emission rates of 6.9, 14.8, and 20.4 lpm. The plots show fairly good agreement between the estimated emission rates and the actual emission rates for wind speeds above 7 kph (note the points for 6.9 lpm are lower at higher wind speeds). The lack of agreement at lower wind speeds may be due to the emission plume not being completely characterized because of the inaccuracy in the directional estimates of the bulk air flow at low wind speeds (i.e. lack of efficiency in capturing the emission plume). The average estimated emission rate between 7 and 15 kph was plotted against the expected controlled emission rate.

Figure 25:
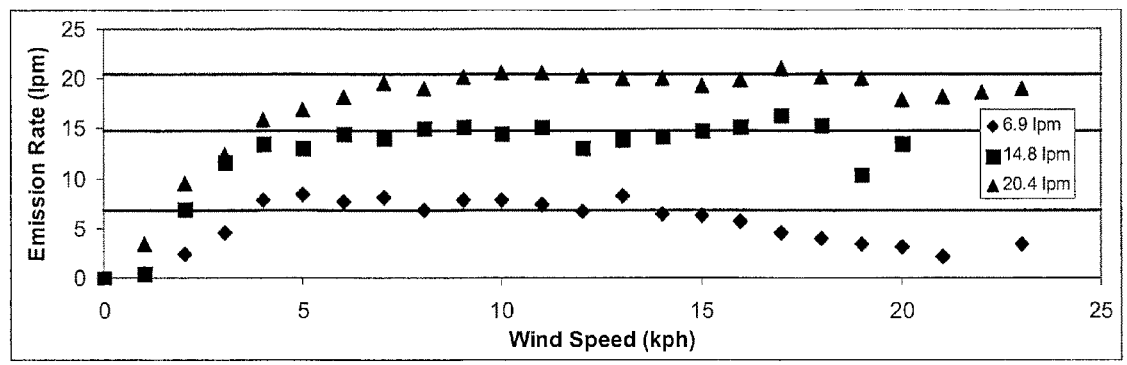
FIG. 25 is a plot of estimated emission rates based on the emission plume characteristic at different wind speeds.

The background noise in the concentration profile across the virtual sampling grid shown in FIGS. 23 to 25 can have an important impact on quantifying the emission rate from the emission plume concentration profile. An important affect is due to the value selected for the background level.

Figure 26:
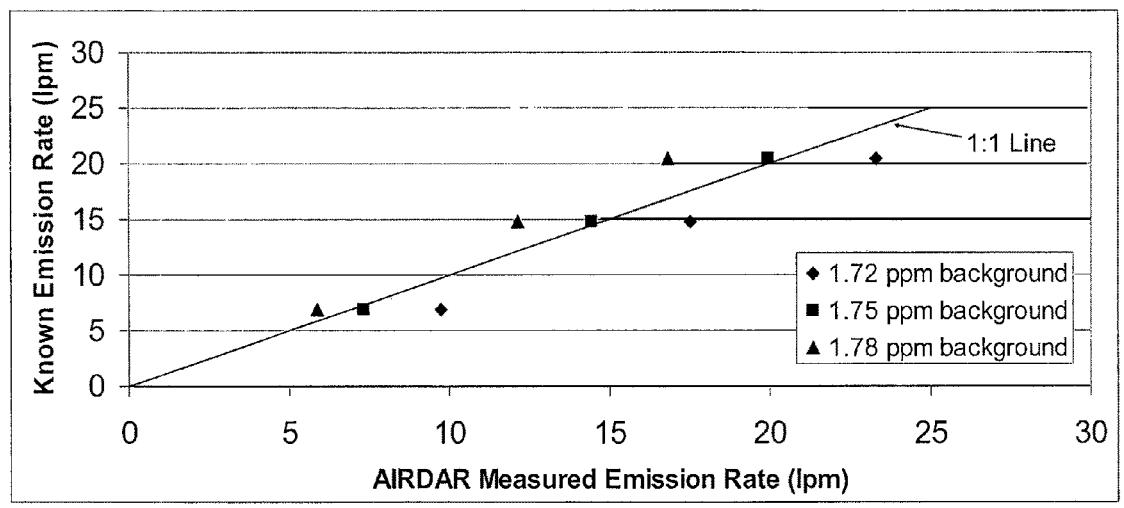
FIG. 26 is a plot of the average emission estimates versus the known emission rate.

The background level of emission has an important impact of the estimates of the emission rate particularly at high wind speeds because it acts across the entire emission plume area. The sensitivity analysis of the background level of THC used levels of 1.72, 1.75, and 1.78 ppm and calculated the resulting estimated emission rates. FIG. 26 shows the results of the analysis and shows that estimated emission rates vary significantly with background levels and the best agreement with expected emission rates uses a background level of 1.75 ppm.

The background levels of THC measured through the project showed some instability. The baseline levels were calculated for the three emission rate periods by averaging the THC readings after removing the reading corresponding to wind directions of 220 to 280 degrees (i.e. the emission source direction) and wind speeds less than 7 kph (to avoid sporadic high reading at low wind speeds). The average reading for the associated time periods are as follows:

October 10 to 30 (14.8 lpm emission rate) was 1.79 ppm
November 1 to December 17 (20.4 lpm emission rate) was 1.76 ppm
December 18 to January 17 (6.9 lpm emission rate) 1.89 ppm.

Figure 27:
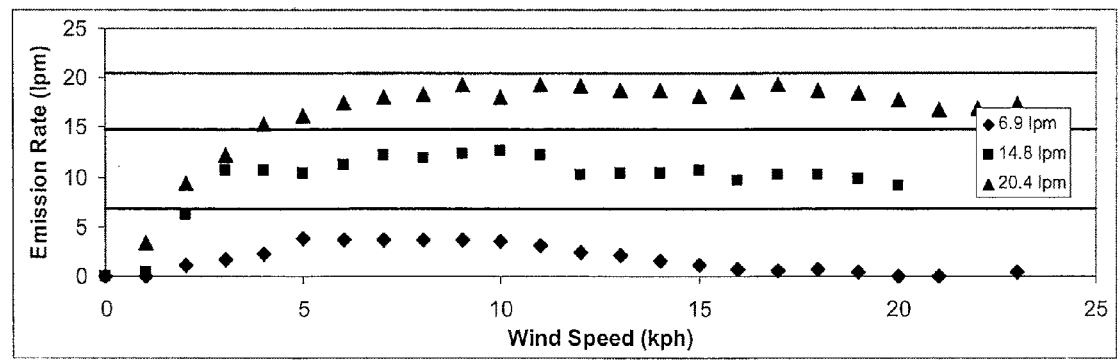
FIG. 27 is a plot of emission rates estimates based on emission plume characteristics at different wind speeds.
Figure 28:
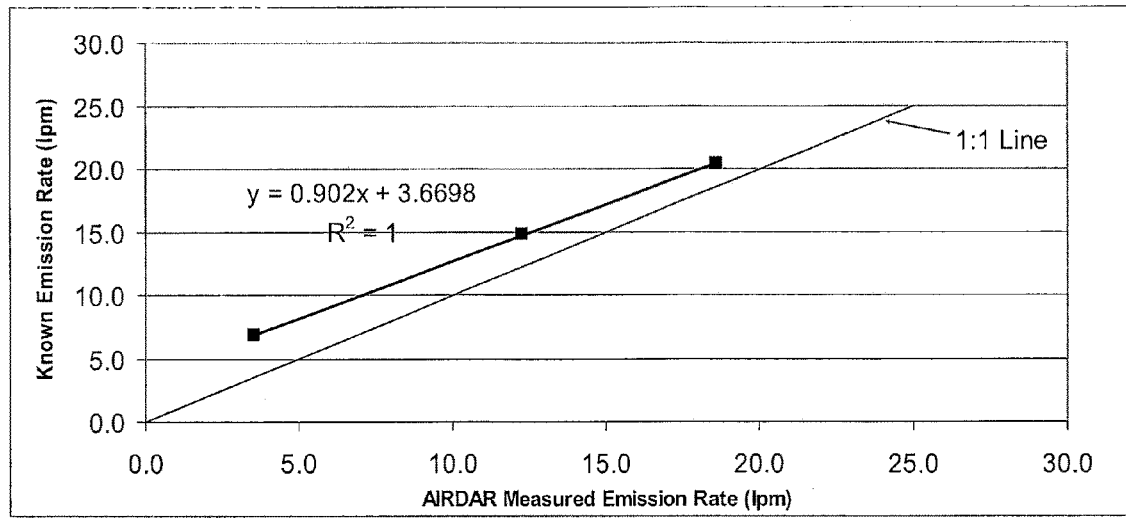
FIG. 28 is a plot of emission rates versus actual emission rates.
Figure 29:
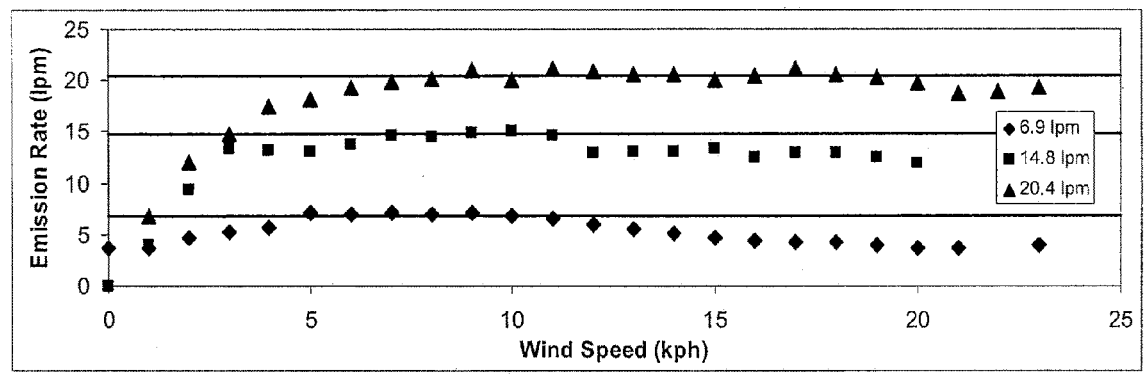
FIG. 29 is a plot of emission rates estimates based on emission plume characteristics at different wind speeds.

The emission rate estimates were calculated using these different baselines for the different time periods and the results are presented in FIG. 27. The average estimated emission rate was calculated for wind speeds between 7 and 11 kph and plotted against the expected emission rate in FIG. 28. There was some lack of agreement that can be corrected by using the equation of the regression line as the correction factors. FIG. 29 shows emission rate estimates with the correction factors applied with good agreement to the expected values.

The reason a correction is needed may be due to the efficiency in isolating the emission plume or due to the background noise in the raw data. Lack of efficiency in isolating the emission plume means that we may only be capturing a portion of the THC molecules leaving the emission source, which likely changes at different wind speeds. This is related to the inaccuracies in predicting the direction of the bulk flow of air. This would explain the underestimation of the emission rate at lower wind speeds. Understanding the efficiencies in capturing emission plumes versus the accuracy of the wind data will allow wind measurements to be taken a great distance from the emission source and correction factors used to estimate the actual emission rate.

This study used many sampling inlets 20 at different heights to characterize the emission plume exactly. In practice, emission rate estimates can be made with far fewer and possible only one measurement position using interpolation and extrapolation of the vertical emission plume shape.

The modeled Gaussian distributions used to determine the plume boundaries (see FIGS. 22 to 24) can also be used to establish the smoothed average plume characteristic over the sampling period. Levels of air concentration of THC (or any compound in question) can be compared to the long term average using the exact wind speed and direction at the time of collection. Changes in source emission rate over time can be tracked by assuming deviations from the long-term average are due to short-term changes in the source emission rate. In this way one can predict changes in source emission rates over time by attributing deviation from long term concentration measures on a virtual sampling grid or virtual sampling arc to changes in source emission rate.

Method 100 in FIG. 2 assumes that a distance to an emission source is known. In some cases, the location of an emission source may not be known and therefore the distance between a measurement position and the emission source may also not be known. Knowing the distance to the emission source allows one to convert the dimensionless emission plume obtained from measured emission concentrations to the appropriate scalar dimension. If the emission source location is known, method 100 shown in FIG. 2 can be used to quantify the emission source. If the emission source locations are not known then method 100 may not be usable and quantifying the emission source(s) may take a number of iterations and comparing predicted locations and emission source sizes from a number of measurement positions and looking for agreement.

Figure 30A:
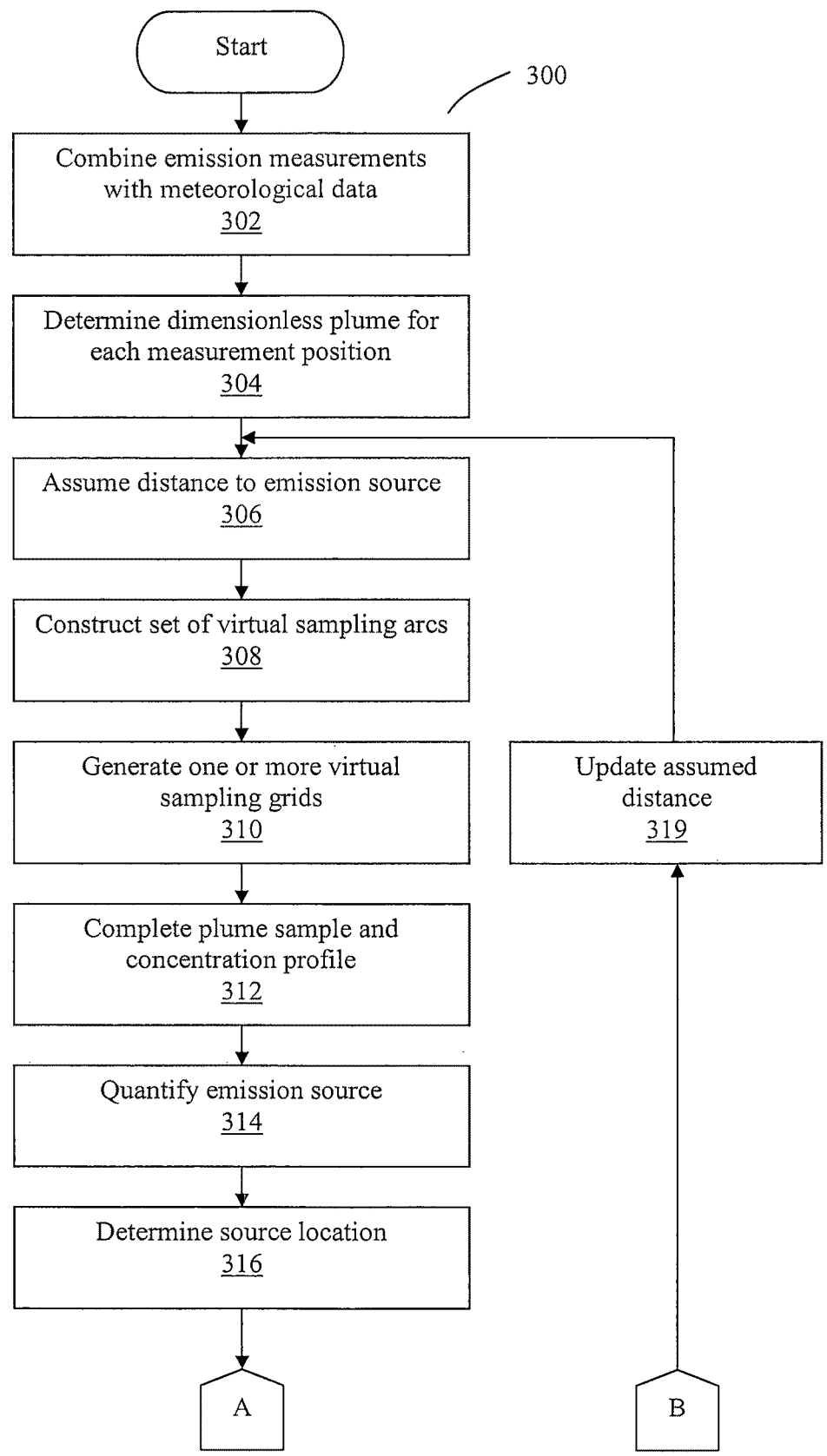
FIG. 30 is a flowchart of a method for quantifying an emission source when the distance between the emission source and the measurement position is not known.
Figure 30B:
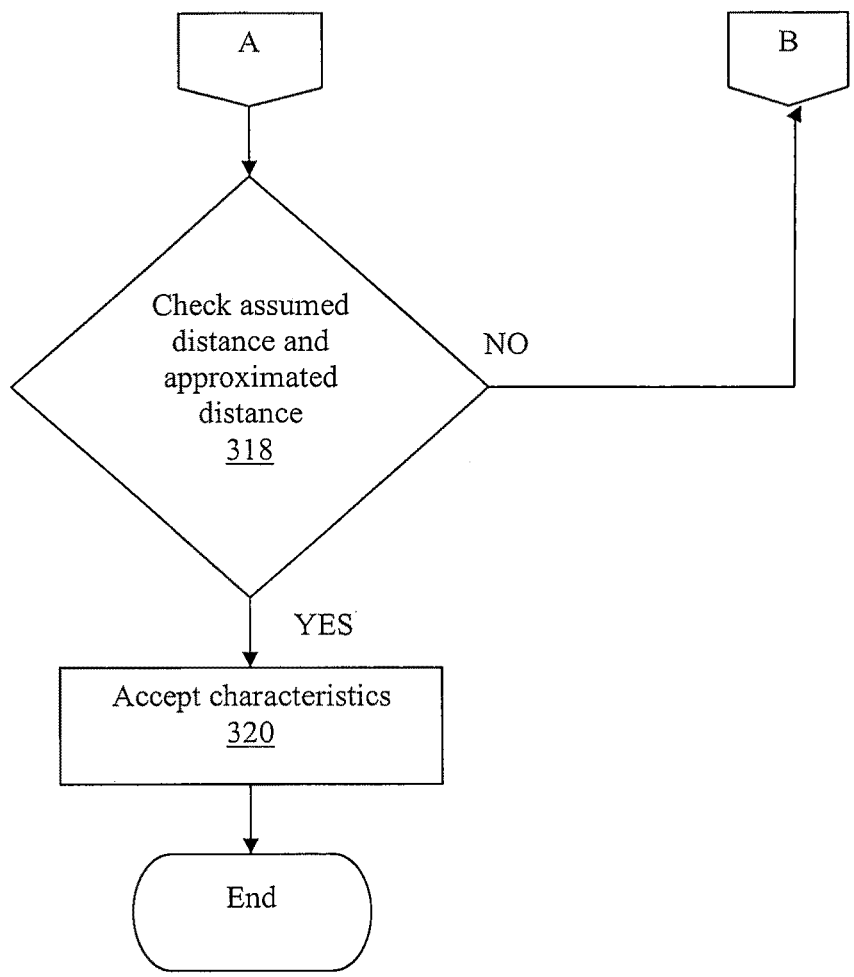

FIG. 30 is a flowchart illustrating a method 300 for quantifying one or more emission sources when the location of the emission source(s) is not known and therefore the distance between a measurement position and the emission source is not known. Method 300 is similar to method 100 shown in FIG. 2 but it includes assuming a distance to the emission source and possible iteration and comparing of predicted locations and sizes from a number of measurement positions to look for agreement.

The method 300 starts and steps 302 and 304 are similar to steps 102 and 104 in the method 100 shown in FIG. 2 wherein measured emission concentration data and wind data are combined to create data about a dimensionless emission plume.

At step 306 a distance to the emission source(s) is assumed and then this assumed distance is used in step 308 to determine a set of virtual sampling arcs. Steps 308, 310, 312 and 314 of method 300 can be performed in a similar manner to steps 108, 110, 112 and 114 of method 100 shown in FIG. 2, with step 314 using the method 200 shown in FIG. 8.

After step 314 is performed and the emission source is quantified based on the distance to the emission source that was assumed at step 306, the method 300 can continue to step 316 and try to determine the emission source location by triangulating the trajectory of identified emission plumes from multiple measurement positions and looking for agreement in source characteristics as described in PCT/CA2008/000080.

The location of an emission source can be approximated by using two or more measurement locations, where each measurement locations is spaced laterally apart from the other measurement locations, to measure emission concentrations and combine them with representative wind speeds and wind directions. The directions or trajectories to the important sources identified by predominant peaks in the plots of measured emission concentrations against the associated representative wind speed and wind direction can be projected outwards from each of the measurement locations. Somewhere along the line of each projected trajectory may be an emission source. These trajectories from the different measurement locations may cross in the vicinity of an emission source. Because multiple trajectories can be projected from each measurement location, some trajectory paths may cross at locations that are not leaks (ghost leaks). When more than two measurement locations are employed, confidence in predicting emission source locations increases if three or four trajectories cross. By computing emission rates for candidate emission sources located at the intersection of these trajectories, the existence of an emission source can be asserted based on a substantial agreement between candidate emission source emission rates by the different measurement locations. The location of this asserted emission source can then be used to approximate a distance to this asserted emission source.

With the emission source location approximated at step 316, the method 300 moves to step 318 and checks whether the assumed distance to the emission source, used at step 306, agrees with the distance to the emission source determined at step 316. If the distance to the emission source assumed at step 306 agrees with the distance to the emission source approximated at step 316, the method 300 can move to step 320 and accept the location and quantification of the emission source. However, if at step 318, the distance to the emission source assumed at step 306 does not agree with the distance to the emission source approximate at step 316, the method 300 can return to step 306 and use the distance to the emission source calculated at step 316 for the assumed distance to the emission source. The method 300 can then perform steps 308, 310, 312, 314 and 316 using the calculated emission source to construct the set of virtual sampling arcs, virtual sampling grids, quantify the emission source, etc. At step 318, the method 300 will once again check the distance to the emission source used at step 306 against an approximated distance to the emission source determined in the subsequent step 316. In this manner, method 300 can iteratively perform the method 300 until the measured distances to the emission source agree with the assumed distance to the emission source to within an acceptable tolerance. When the assumed distance and calculated distance are within an acceptable range, the characteristics of the emission source can be accepted at step 420 and the method 300 can end.

In this manner, method 300 can be used to quantify one or more emission sources when the location(s) of the emission source(s) are not specifically known.

Virtual sampling arcs and virtual sampling grids of measurement positions can be determined by assuming that the emissions source is acting as a point emission source. However, this may not always an accurate assumption. The methods described herein are also applicable to other source configurations like area emission sources or multiple emission sources of similar size. Referring again to FIG. 2, the method 100 could also be used for area emission sources. Steps 102 and 104 are performed with the emission concentration measurements combined with wind data to construct a dimensionless emission plume. Step 108 is then performed and a set of virtual sampling arrays are constructed. Unlike the virtual sampling arcs, these virtual sampling arrays may not follow an arc but rather vary as a result of the area emission course. Because the emission source is not being treated as a point emission source, but rather an area emission source, the virtual sampling arcs must be constructed in a slightly different manner than when a point emission source is being assumed. In one aspect, quantifying area emission sources can be accomplished by envisioning that a measurement position gets a concentration measurement of an emission plume from an area emission source downwind from a "catchment" area of the area emission source.

Figure 31:
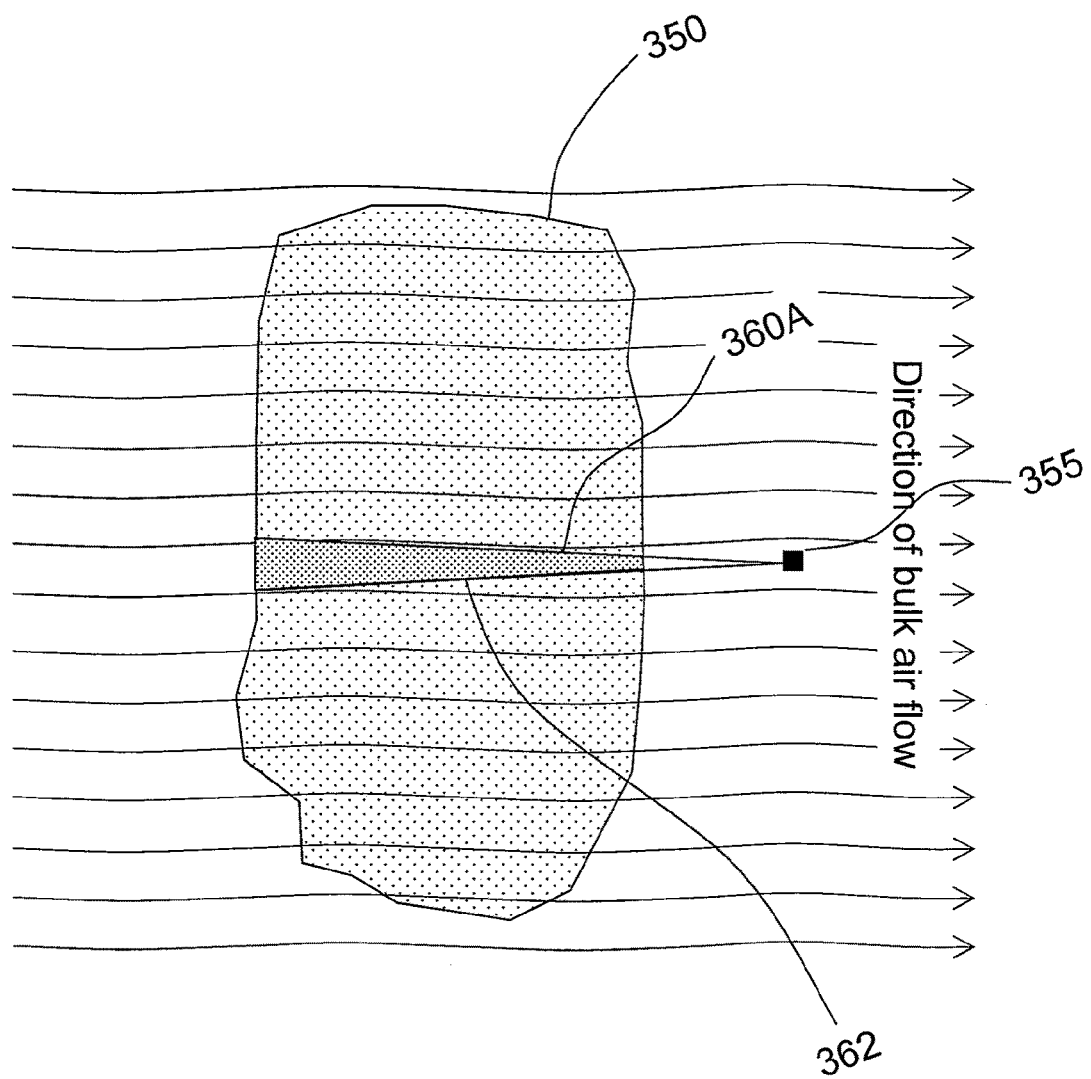
FIG. 31 is a schematic illustration of an area emission source and a catchment area.
Figure 32:
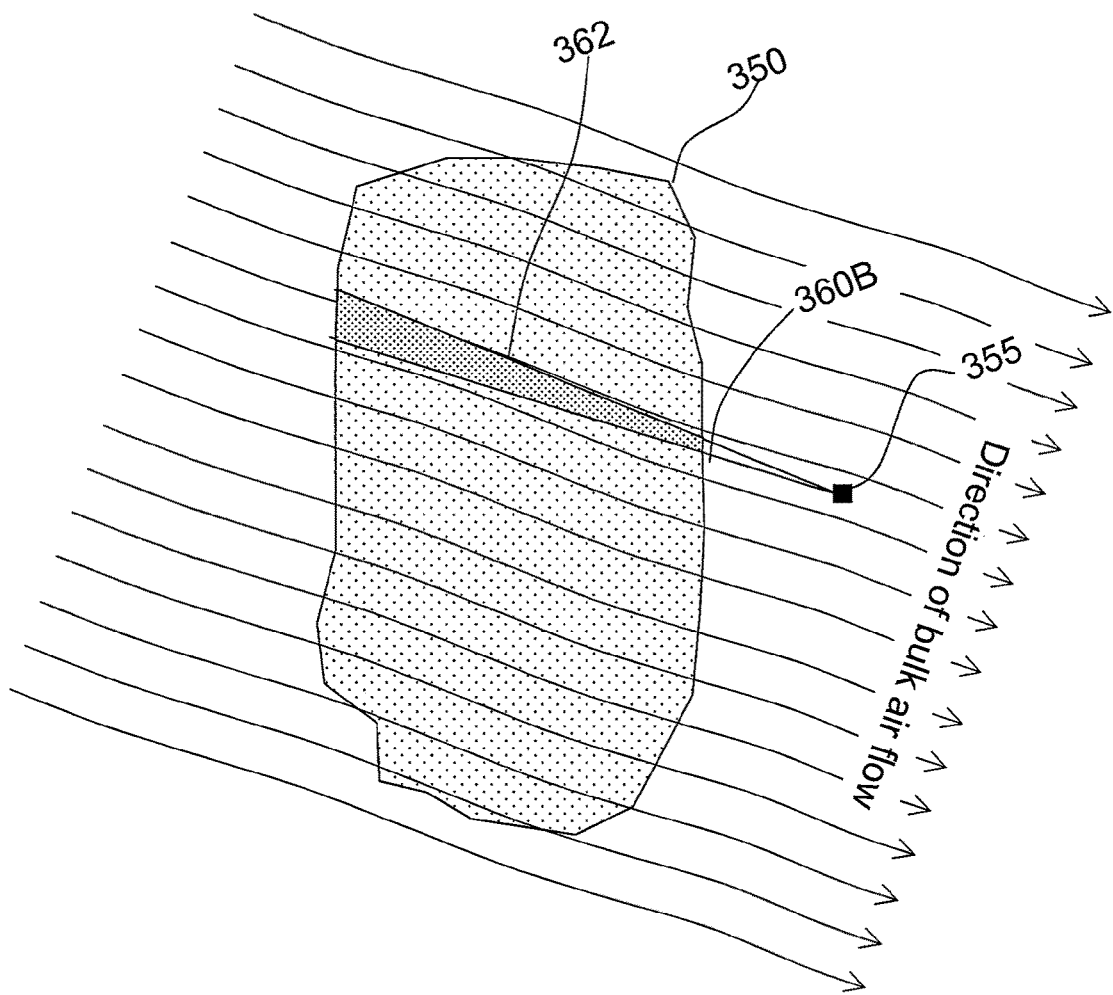
FIG. 32 is a schematic illustration of the area emission source in FIG. 31 and a second catchment area.
Figure 33:
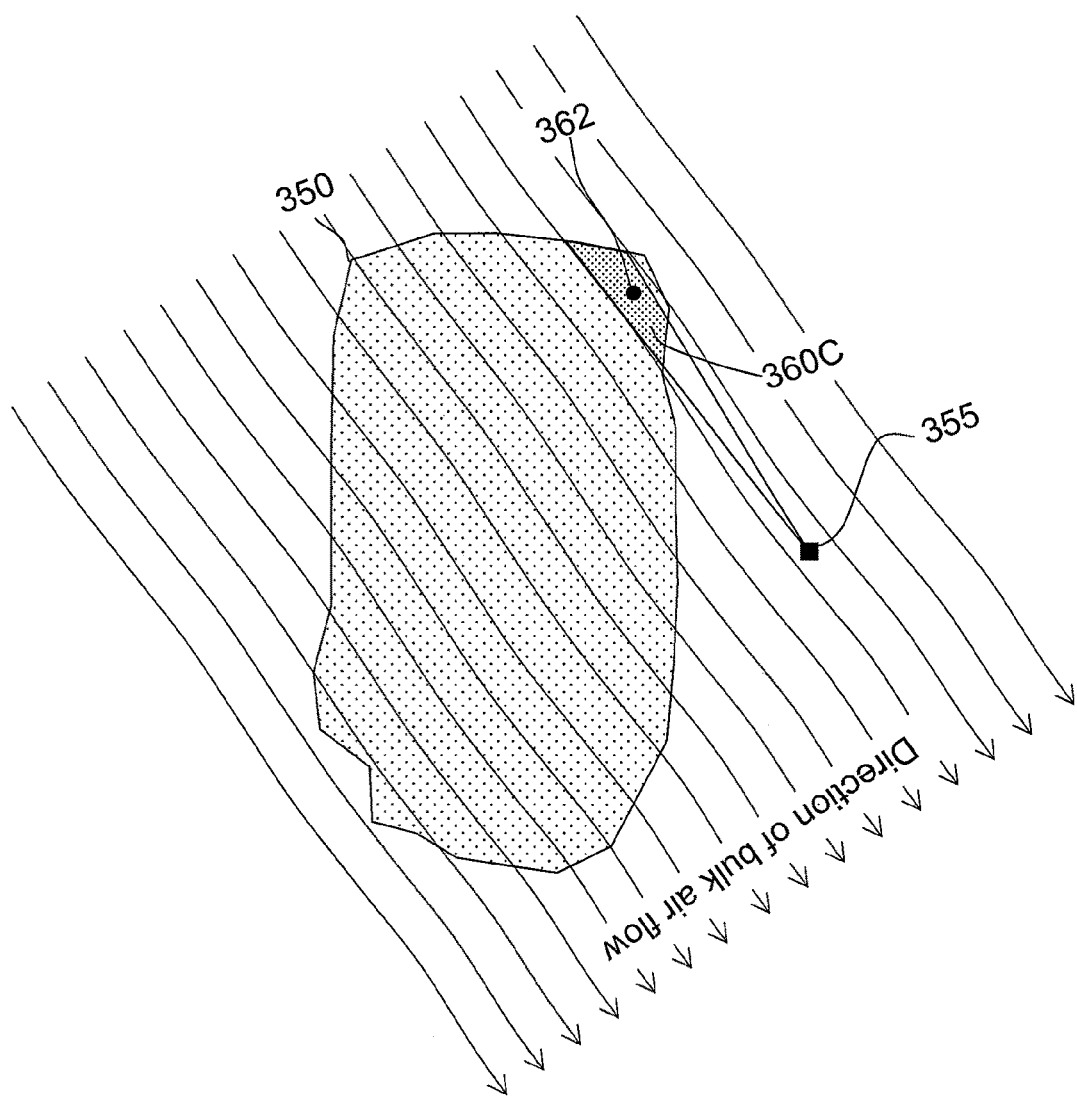
FIG. 33 is a schematic illustration of the area emission source in FIG. 31 and a third catchment area.

FIG. 31 illustrates an area emission source 350 and a measurement position 355 measuring emission concentrations originating from a first catchment area 360A of the area emission source 350. The measurement position 355 could be the sampling tower 12 containing the sampling inlets 20 in the sampling system 10 shown in FIG. 1. Depending on the direction of the wind relative to the area emission source 350 and the measurement position 355, the measurement position 355 obtains measurements of the concentration of emission from a number of catchment areas of the area emission source 350. At different wind directions there will be different catchment areas of the area emission source under surveillance. FIG. 32 illustrates the area emission source 350 and the measurement position 355 where the wind direction differs from FIG. 31 and therefore the measurement position 355 is measuring the emission concentrations from a second catchment area 360B of the area emission source 350. FIG. 33 illustrates the area emission source 350 and the measurement position 355 when the wind has yet another direction and the measurement position 355 is measuring the emission concentrations from a third catchment area 360C of the area emission source 350.

Area emission sources will have a more complex curve that will be centered at a representative center 362 of the catchment areas 360, a representative distance from the measurement position 355. The representative distance is the distance between the measurement position 355 and the representative center 362 of the catchment area 360 of the area emission source 350 being measured. This representative distance may be variable depending on the catchment area 360 being measured by the measurement position 355. This representative center of an area emission source or subsection of an area emission source is the position whose distance to the measurement position will provide the appropriate emission rate when used in the quantification steps of this procedure. In one aspect, the centroid of the catchment area 360 may be used as the representative center. The scalar width of the emission plume for each wind direction will be based on the representative distance to the representative center 362 of the catchment area 360 being measured and can be calculated as follows:

$$ScalarWidth = \frac{AngularWidth}{360} \times \text{Circumference} \quad [5]$$
$$= \frac{AngularWidth}{360} \times 2 \times \pi \times r$$

wherein r is the representative distance to the catchment area slices.

Figure 34:
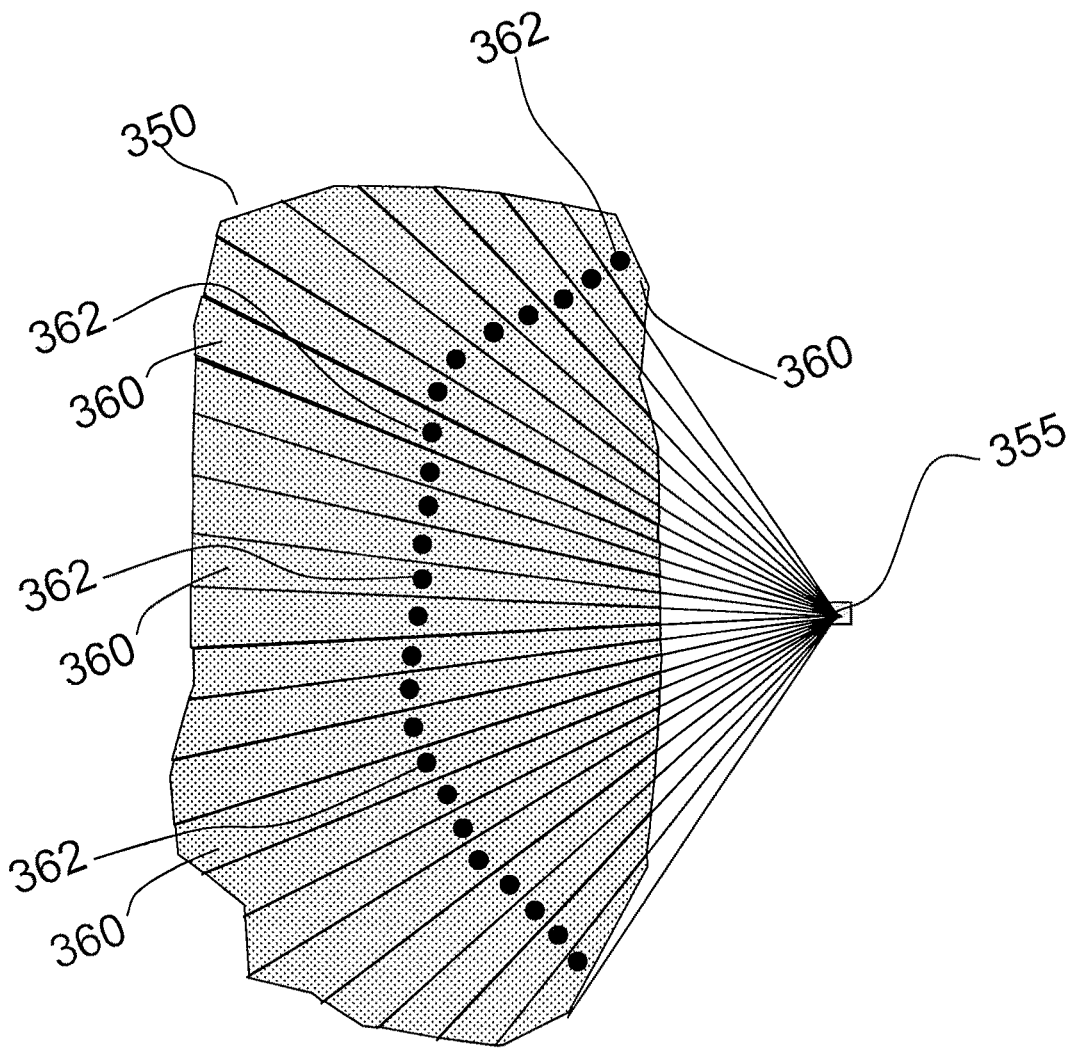
FIG. 34 is a schematic illustration of the area emission source in FIG. 31 divided in catchment area.
Figure 35:
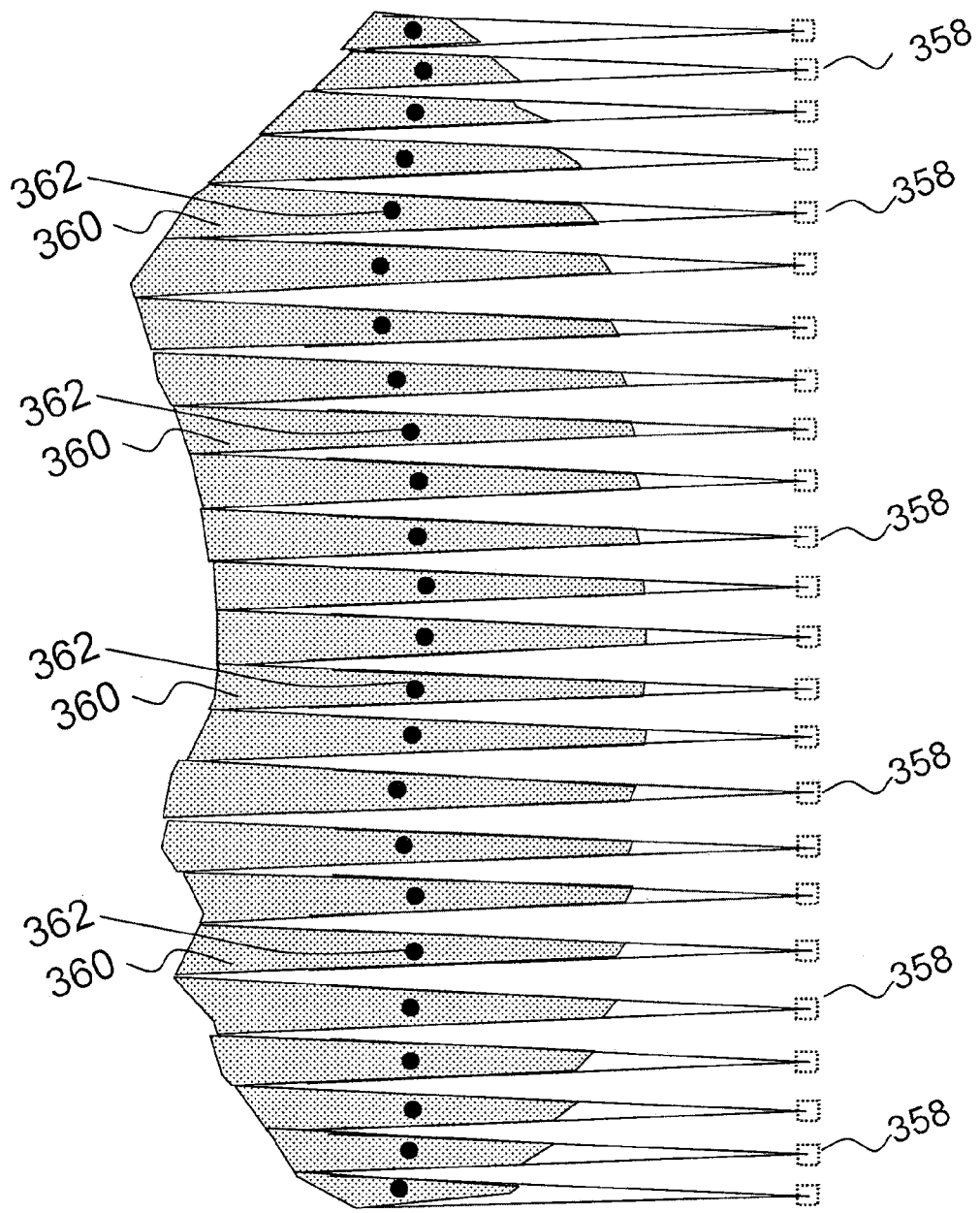
FIG. 35 is a schematic illustration of a distorted area emission source.

FIG. 34 shows the area emission source 350 and the measurement positions 355 wherein the area emission source 350 is divided into measurement catchment areas 360 related to different wind directions. FIG. 35 shows how the single measurement position 355 can be represented as a series of virtual measurement positions 358 related to measurement catchment area 360 slices. The distance between the virtual measurement positions 358 can be determined using Equation [5] to determine the arc length of a circle with the radius equal to distance between measurement position and the representational center. In this way the angular plume horizontal dimension can be converted into a scalar horizontal dimension to construct a virtual sampling array. Unlike the earlier described virtual sampling arcs, the area emission source forms a virtual sampling array that will necessarily follow the curve of an arc but may vary in curvature along its length as shown in FIG. 35. The change of emission plume intensity along the horizontal dimension can also be used to map out the regions of the area emission source that have higher (or lower) emission rates particularly if observed from multiple measurement positions.

Referring again to FIG. 1, with virtual sampling arrays created for measured emission concentrations at the measurement position 355, step 108 has been performed and the method 100 can continue on to step 110 and use the constructed virtual sampling arrays to construct one or more virtual sampling grids before performing steps 112 and 114 and quantifying the area emission source 355.

Figure 36:
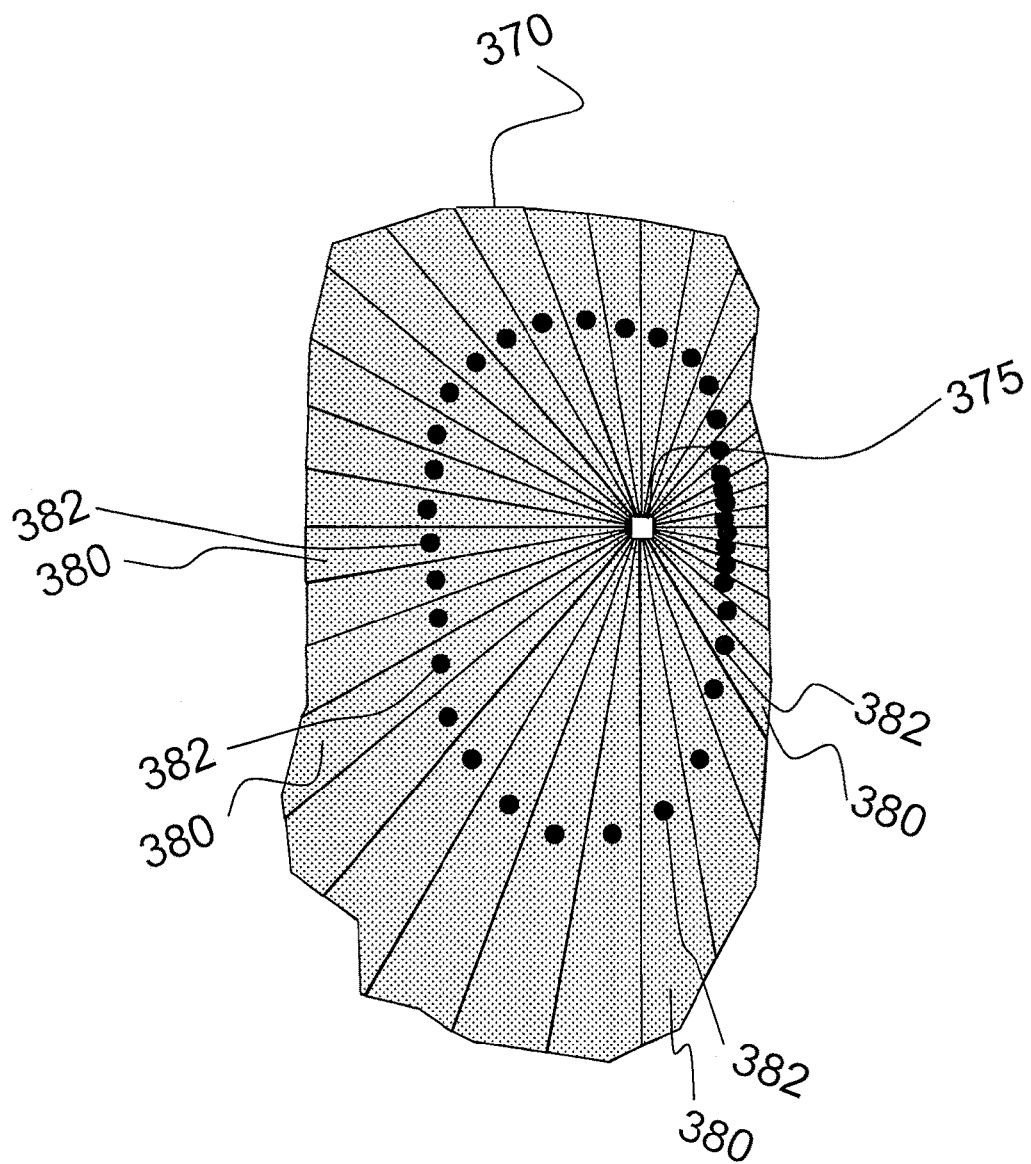
FIG. 36 is a schematic illustration of a measurement position inside an area emissions source.
Figure 37:
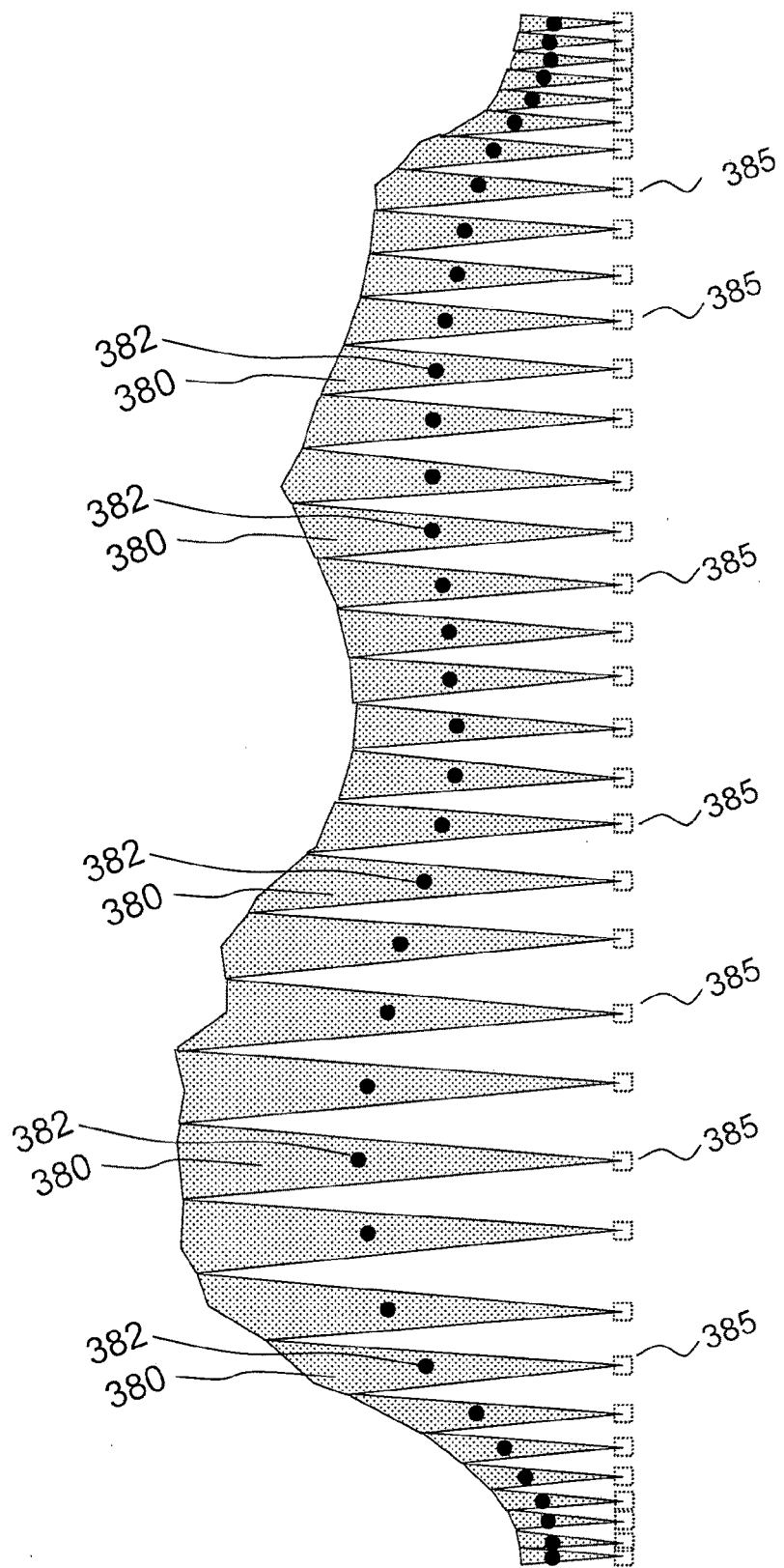
FIG. 37 is a schematic illustration of a distorted area emission source.

The measurement point for an area emission source do not need to necessarily be located outside the area emission source, rather it might be located within the area emission source. FIG. 36 illustrates an aspect where a measurement position 375 is located inside an area emission source 370. As the wind changes direction, the emission plume from a different catchment area 380 will arrive at the measurement position 375. The changing wind direction will expose the measurement position 375 to a different portion of the area source emission 370. The catchment areas 380 will be like pie slices. FIG. 37 shows how the single measurement position 375 can be represented as a series of virtual measurement positions 385 related to measurement catchment area 380 slices. The distance between the virtual measurement positions 385 can be obtained using Equation [5] to determine an arc length of a circle with a radius equal to the distance between the measurement position 375 and the representative center 382 of the measurement catchment area 380 slice. In this way, a measurement position 375 inside an area source emission 370 can be used to stretch out the angular plume dimensions, convert them to scalar dimensions and construct a virtual sampling array to be used to approximate the emission rate of the area emission source 370. Again, areas of higher (or lower) emission rate can be identified particularly if multiple measurement positions are used.

If emission plumes from multiple sources can be differentiated then they can be quantified separately. Observation positions from other locations can help to differentiate the emission plumes. Emission plumes that result from multiple point sources and cannot be differentiated can be quantified as a group (i.e. an area emission source). The distance from the measurement position to the area emission sources can be taken to the centroid of the group of sources or to an imaginary central focus point upwind of the group of emission sources.

An area emission source can be treated as a point source if the observation position is far enough away from the area emission source. Quantifying emission rates from area emission sources can be done by having measurement positions strategically located in and around the area emission source. If there is no evidence of hot spots (sub areas of higher emission rate) then the area emission source can be treated as having a homogenous emission rate and the emission plume generated will reflect the area of the emission source in the upwind fetch. If the plume is not homogenous and higher emission rates are evident from sub-areas of the larger emitting area, then relating emission plume intensities to sub-area emission rates from multiple measurement positions and then quantifying the sub-area emission rates and asserting the locations and pattern of the sub-area emission rates based on agreement from multiple measurement positions. The overall emission rate is then determined by totaling the sub-area emission rates across the entire area emission source.

The scalar width of an emission plume originating from an area emission source can be assumed to be the same width as the area emission source itself. The increased width due to the emission plume dispersing at the edges of the emission plume may be less important than the emission plume width established by the width of the area emission source. The position of the measurement position relative to the area emission source can be used to adjust the plume scalar width for different wind speeds.

In a further aspect, these techniques can be used with data collected from mobile monitoring equipment. With knowledge of the position of the detectors in motion, actual sampling arcs, arrays and grids (for steps 108 and 110 of method 100 shown in FIG. 2 or steps 208 and 210 of method 200 shown in FIG. 8) can be developed to intercept emission plumes, delineate emission plume boundaries and determine emission plume trajectory. Emission plume trajectories from multiple sampling positions can be used to determine the location of the emission sources using triangulation techniques.

Many applications for the systems and methods described herein can be envisioned including: emission from a large area source like a city could be measured this way; emission from a large tailing pond could be measured with these techniques; military applications, measurement from moving vehicles; homeland security, monitoring for releases of nerve agents in a city; etc.

In another aspect, treating the emission source as an area emission source could be useful in situation where the emission plumes are so large that you cannot get far enough away to assume the emission source is a point emission source. For example, this approach could quantify emission of an entire city to find the overall emission rate and the location and timing of emission from sub areas of the city.

In a further aspect, this approach could be useful to provide surveillance of attacks with air borne agents being released in a city.

Emission plumes can be visualized and characterized with measures of air concentrations taken down wind. Knowing the shape, size, and concentration profile of the emission plume at different wind speeds enables a flux calculation to predict the associated emission rate of the source causing the plume.

The previous description of the disclosed embodiments is provided to enable any person skilled in the art to make or use the present invention. Various modifications to those embodiments will be readily apparent to those skilled in the art, and the generic principles defined herein may be applied to other embodiments without departing from the spirit or scope of the invention. Thus, the present invention is not intended to be limited to the embodiments shown herein, but is to be accorded the full scope consistent with the claims, wherein reference to an element in the singular, such as by use of the article "a" or "an" is not intended to mean "one and only one" unless specifically so stated, but rather "one or more". All structural and functional equivalents to the elements of the various embodiments described throughout the disclosure that are known or later come to be known to those of ordinary skill in the art are intended to be encompassed by the elements of the claims. Moreover, nothing disclosed herein is intended to be dedicated to the public regardless of whether such disclosure is explicitly recited in the claims.

The invention claimed is:

1. A system for quantifying an emission source comprising:
   a plurality of sampling points operative to obtain emission concentration measurements;
   at least one emission monitor operative to take emission concentration measurements at the plurality of sampling points;
   a data processing device operatively connected to the at least one emission monitor to obtain emission concentration measurements from the at least one monitor, the data processing device operative to:
      obtain a plurality of emission concentrations measurements from the at least one emission monitor;
      obtain wind speed measurements and wind direction measurements when the plurality of emission concentration measurements were taken;
      for each sampling point, construct a virtual sampling arc made up of a plurality of points, each point based on:
         an emission concentration measurement taken at the sampling point;
         a wind direction measurement when the emission concentration measurement was taken; and
         an approximate distance to the emission source, wherein all of the emission concentration measurements used to construct one of the virtual sampling arcs were taken at substantially the same wind speed;
      group virtual sampling arcs made of emission concentrations measurements at substantially the same wind speed into a virtual sampling grid; and
      approximate the amount of emissions passing through the virtual sampling grid.

2. The system of claim 1 wherein the sampling points are provided vertically spaced on a tower.

3. The system of claim 1 wherein the at least one emission monitor is an open-path gas detector.

4. The system of claim 1 wherein an open-path gas detector is placed at each sampling point to obtain an emission concentration measurement at the sampling point.

5. The system of claim 1 wherein the sampling points are vertically spaced.

6. The system of claim 5 wherein the sampling points are vertically aligned.

7. The system of claim 1 wherein the wind speed measurements and the wind direction measurements are taken at the plurality of sampling points.

8. The system of claim 1 wherein the approximate distance to the emission source from the sampling point is an estimated distance.

9. The system of claim 1 wherein the data processing device is further operative to:
obtain an emission concentrations measurements taken at an additional sampling point spaced laterally apart from the plurality of sampling points;
use the emission concentration measurements taken at the additional sampling point to determine a first trajectory of emissions from the emission source;
determine a second trajectory of emissions from the emission source using emission concentration measurements taken at the plurality of sampling points; and
use the first trajectory and second trajectory to approximate the distance to the emission source.

10. The system of claim 9 wherein the amount of emissions passing through the virtual sampling grid and the distance to the emission source are iteratively approximated.

11. The system of claim 1 wherein the amount of emissions passing through the virtual sampling grid is determined by dividing the virtual sampling grid into sections; approximating the flowrate of emissions through each section; and determining an approximate total flowrate of an emissions plume through the virtual sampling grid.

12. The system of claim 11 further comprising determining whether each section falls within an emission plume originating from the emission source.

13. The system of claim 1 further comprising approximating a shape of an emission plume originating from the emission source.

14. The system of claim 13 further comprising interpolating additional points in the virtual sampling grid where no points are present.

15. The system of claim 13 further comprising extrapolating additional points beyond the virtual sampling grid.

16. A system for quantifying an area emission source, the system comprising:
a plurality of sampling points operative to obtain a plurality of emission concentrations measurements;
at least one at least one emission monitor operative take emission concentration measurements at the plurality of sampling points;
a data processing device operatively connected to the at least one emission monitor to obtain emission concentration measurements from the at least one monitor, the data processing device operative to:
obtain a plurality of emission concentrations measurements from the at least one emission monitor;
obtain wind speed measurements and wind direction measurements when the plurality of emission concentration measurements are taken;
for each sampling point, construct a virtual sampling array made up of a plurality of points, each point based on:
an emission concentration measurement taken at the sampling point;
a wind direction measurement when the emission concentration measurement was taken; and
a representative distance to a representative center of a catchment area of the area emission source being measured by the emission concentration measurement, wherein all of the emission concentration measurements used to construct one of the virtual sampling arrays were taken at substantially the same wind speed;
grouping virtual sampling arrays made of emission concentrations measurements taken at substantially the same wind speed into a virtual sampling grid; and
approximating the amount of emissions passing through the virtual sampling grid.

17. The system of claim 16 wherein the representative center is the catchment area of the area emission source being measured by the emission concentration measurement.

18. The system of claim 16 wherein the representative distance varies between emission concentration measurements.

19. The system of claim 16 wherein the sampling points are vertically spaced.

20. The system of claim 16 wherein the sampling points are vertically aligned.

21. The system of claim 16 wherein the wind speed measurements and the wind direction measurements are taken at the plurality of sampling points.

22. The system of claim 16 wherein the amount of emissions passing through the virtual sampling grid is determined by dividing the virtual sampling grid into sections; approximating the flowrate of emissions through each section; and determining an approximate total flowrate of an emissions plume through the virtual sampling grid.

* * * * *